(12) United States Patent
Chenoweth et al.

(10) Patent No.: US 10,487,089 B2
(45) Date of Patent: Nov. 26, 2019

(54) IMAGING AGENTS AND METHODS OF IDENTIFYING SAME

(71) Applicant: The Trustees of the University of Pennsylvania, Philadelphia, PA (US)

(72) Inventors: David M. Chenoweth, Philadelphia, PA (US); Robert-Andre F. Rarig, Narberth, PA (US); Mai N. Tran, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 254 days.

(21) Appl. No.: 15/127,305

(22) PCT Filed: Mar. 20, 2015

(86) PCT No.: PCT/US2015/021793
§ 371 (c)(1),
(2) Date: Sep. 19, 2016

(87) PCT Pub. No.: WO2015/143349
PCT Pub. Date: Sep. 24, 2015

(65) Prior Publication Data
US 2017/0183356 A1    Jun. 29, 2017

Related U.S. Application Data

(60) Provisional application No. 61/968,709, filed on Mar. 21, 2014.

(51) Int. Cl.
*A61K 9/00*       (2006.01)
*C07D 491/052*  (2006.01)
*C07D 491/22*    (2006.01)
*A61K 49/00*     (2006.01)

(52) U.S. Cl.
CPC ...... *C07D 491/052* (2013.01); *A61K 49/0052* (2013.01); *C07D 491/22* (2013.01)

(58) Field of Classification Search
CPC .................................................. C07D 491/052
See application file for complete search history.

(56) References Cited

U.S. PATENT DOCUMENTS

| | | |
|---|---|---|
| 3,761,942 A | 9/1973 | Lorenz |
| 5,501,945 A * | 3/1996 | Kanakkanatt ............ A61L 2/28 426/323 |
| 8,476,443 B2 | 7/2013 | Pande et al. |

(Continued)

OTHER PUBLICATIONS

Rarig, Synthesis and Conformational Dynamics of the Reported Structure of Xylopyridine A, J. Am. Chem. Soc., 2013, 135, 9213-9219.*

(Continued)

*Primary Examiner* — Paul W Dickinson
(74) *Attorney, Agent, or Firm* — Riverside Law LLP

(57) ABSTRACT

The present invention includes a novel method capable of identifying a compound as an imaging agent using a DAZAX-based scaffold or derivative thereof. The present invention further includes novel imaging agents. The present invention further includes a method of modifying a DAZAX-based scaffold or derivative thereof. The present invention further includes a method for imaging a sample.

28 Claims, 61 Drawing Sheets

(56) References Cited

U.S. PATENT DOCUMENTS

| | | |
|---|---|---|
| 2008/0220407 A1 | 9/2008 | Tang |
| 2009/0305410 A1 | 12/2009 | Mao et al. |
| 2010/0278745 A1 | 11/2010 | Lange et al. |

OTHER PUBLICATIONS

Lichtman et al., "Fluorescence Microscopy", 2005, Nat. Methods 2:910-919.

Hein et al., "Stimulated Emission Depletion (STED) Nanoscopy ofa Fluorescent Protein-Labeled Organelle Inside a Living Cell", 2008, Proc. Natl. Acad. Sci. USA 105:14271-14276.

Patterson et al., "Superresolution Imaging using Single-Molecule Localization", 2010, Annu. Rev. Phys. Chem. 2010 61:345-367.

Huang et al., "Super-resolution fluorescence microscopy", 2009, Annu. Rev. Biochem. 78:993-1016.

Kobayashi et al., "Highly activatable and environment-insensitive optical highlighters for selective spatiotemporal imaging of target proteins", 2012, J. Am. Chem. Soc. 134:11153-11160.

Lord et al., "A photoactivatable push-pull fluorophore for single-molecule imaging in live cells", 2008, J. Am. Chem. Soc. 130:9204-9205.

Lim et al., "Photoinducable bioorthogonal chemistry: a spatiotemporally controllable tool to visualize and perturb proteins in live cells", 2011, Accounts Chem. Res. 44:828-839.

Ramil et al., "Photoclick chemistry: a fluorogenic light-triggered in vivo ligation reaction", 2014, Curr. Opin. Chem. Biol. 21:89-95.

Faal et al., "4-Hydroxytamoxifen probes for light-dependent spatiotemporal control of Cre-ER mediated reporter gene expression", 2015, Mol. Biosystems 11:783-790.

Chozinski et al., "Twinkle, twinkle little star: Photoswitchable fluorophores for super-resolution imaging", 2014, FEBS letters 588:3603-3612.

Ueno et al., "Rational principles for modulating fluorescence properties of fluorescein", 2004, J. Am. Chem. Soc. 126:14079-14085.

Yu et al., "Rapid, photoactivatable turn-on fluorescent probes based on an intramolecular photoclick reaction", 2011, J. Am. Chem. Soc. 133:11912-11915.

An et al., "Design and synthesis of laser-activatable tetrazoles for a fast and fluorogenic red-emitting 1, 3-dipolar cycloaddition reaction", 2013, Org. Lett. 15:5496-5499.

Vaughan et al., "Ultrabright photoactivatable fluorophores created by reductive caging", 2012, Nat. Methods 9:1181-1184.

Lacivita et al., "Activatable Fluorescent Probes: A New Concept in Optical Molecular Imaging", 2012, Curr. Med. Chem. 19:4731-474.

Mernandez-Suarez et al., "Fluorescent probes for super-resolution imaging in living cells", 2008, Nat. Rev. Mol. Cell Biol. 9:929-943.

Cho et al., "Photoconversion of o-hydroxycinnamates to coumarins and its application to fluorescence imaging", 2009, Tet. Lett. 50:4769-4772.

Gagey et al., "Two-Photon Uncaging with Fluorescence Reporting: Evaluation of the o-Hydroxycinnamic Platform", 2007, J. Am. Chem. Soc. 129:9986-9998.

Ballister et al., "Localized light-induced protein dimerization in living cells using a photocaged dimerizer", 2014, Nat. Comm. 5:5475.

Kamkaew et al., "BODIPY dyes in photodynamic therapy", 2013, Chem. Soc. Rev. 42:77-88.

Yuan et al., "A unique approach to development of near-infrared fluorescent sensors for in vivo imaging", 2012, J. Am. Chem. Soc. 134:13510-13523.

Pansare et al., "Review of long-wavelength optical and NIR imaging materials: contrast agents, fluorophores, and multifunctional nano carriers", 2012, Chem. Mat. 24:812-827.

Zheng et al., "Advances in modifying fluorescein and rhodamine fluorophores as fluorescent chemosensors", 2013, Chem. Comm. 49:429-447.

Rarig et al., "Synthesis and Conformational Dynamics of the Reported Structure of Xylopyridine A", 2013, J. Am. Chem. Soc. 135:9213-9219.

Mallory et al., "Photochemistry of stilbenes. III. Some aspects of the mechanism of photocyclization to phenanthrenes", 1964, J. Am. Chem. Soc. 86:3094-3102.

Villani et al., "Benzopyranopyridine derivatives. 1. Aminoalkyl derivatives of the azaxanthenes as bronchodilating agents", 1975, J. Med. Chem. 18:1-8.

Quanshan et al., "Synthesis and Characterization of Oligofluorene Nanoparticles for Cell Imaging," 2012, Acta Chimica Sinica 70:2137-2143.

\* cited by examiner

IMAGING AGENTS AND METHODS OF IDENTIFYING SAME

CROSS-REFERENCE TO RELATED APPLICATIONS

The present application is a 35 U.S.C. § 371 national stage patent application of International Patent Application No. PCT/US2015/021793, filed on Mar. 20, 2015, and which claims priority to U.S. Provisional Application No. 61/968,709, filed on Mar. 21, 2014, all of which applications are incorporated by reference herein in their entireties.

BACKGROUND OF THE INVENTION

The chemistry-biology interface is experiencing a renaissance with the advent of many fluorescence based techniques for studying cell and tissue level events (Lichtman et al., 2005, Nat. Methods 2: 910-919; Hein et al., 2008, Proc. Natl. Acad. Sci. USA 105: 14271-14276; Patterson et al., 2010, Annu. Rev. Phys. Chem. 2010 61: 345-367; Huang et al., 2009, Annu. Rev. Biochem. 78: 993-1016). Therefore, there is an increasing need for new fluorescent molecules with uniquely tailored properties for biological imaging (Grimm et al., 2013, Prog. Mol. Biol. Transl. 113: 1-34; Ramil and Lin, 2013, Chem. Commun. 49: 11007-11022; Shih et al., 2014 Curr. Opin. Chem. Biol. 21: 103-111). Among them are photoactivatible probes which allow for the possibility of precise spatial and temporal control with minimal physical and chemical intervention. There are many hurdles and requirements for the development of photoactivatable fluorophores and very few irreversible intracellular photoactivation mechanisms have been reported beyond traditional photoswitching and photodecaging strategies (Kobayashi et al., 2012, J. Am. Chem. Soc. 134: 11153-11160; Lord et al., 2008, J. Am. Chem. Soc. 130: 9204-9205; Lim and Lin, 2011, Accounts Chem. Res. 44: 828-839; Ramil and Lin, 2014, Curr. Opin. Chem. Biol. 21: 89-95; Faal et al., 2015, Mol. bioSystems 11: 783-790; Chozinski et al., 2014, FEBS letters 588: 3603-3612; Ueno et al., 2004, J. Am. Chem. Soc. 126: 14079-14085; Yu et al., 2011, J. Am. Chem. Soc. 133: 11912-11915; An et al., 2013, Org. Lett. 15: 5496-5499; Vaughan et al., 2012, Nat. Methods 9: 1181-1184). New photoactivation concepts and mechanisms would expand the fluorescent probe toolbox providing new tools for investigating biological systems.

Photoactivatable fluorescent probes are powerful tools for studying biological system due to the high spatial and temporal control afforded by light. Photoactivatable probes can be genetically encoded proteins (Ludyanov et al., 2005, Rev. Mol. Cell Biol. 6: 885-891; Welman et al., 2010, J. Biol. Chem. 285: 11607-11616; Verkhusha and Sorkin, 2005, Chem. Biol. 12: 279-285; Patterson and Lippincott-Schwartz, 2004, Methods 32: 445-450; Shcherbakova and Verkhusha, 2014, Curr. Opin. Chem. Biol. 20: 60-68; Adam and Berardozzi, 2014, Curr. Opin. Chem. Biol. 20: 92-102) or small molecules (Lacivita et al., 2012, Curr. Med. Chem. 19: 4731-4741; Mernandez-Suarez and Ting, 2008, Nat. Rev. Mol. Cell Biol. 9: 929-943). Each of these technologies comes with its own benefits and limitations and may be thought of as complimentary to one another depending on the application. Kaede represents the first discovery of a photoactivatable fluorescent protein and much progress has been made in recent years with purely genetically encoded approaches (Ando et al., 2002, Proc. Natl. Acad. Sci. USA 99: 12651-12656; Tomura et al., 2008, Proc. Natl. Acad. Sci. USA 105: 10871-10876; Hayashi et al., 2007, J. Mol. Biol. 372: 918-926; Dittrich et al., 2005, Biophys. J. 89: 3446-3455). Small molecule photoactivatable probes have also found widespread use and they generally rely on a small number of photoactivation mechanisms such as photoisomerization (Cho et al., 2009, Tet. Lett. 50: 4769-4772; Gagey et al., 2007, J. Am. Chem. Soc. 129: 9986-9998), photo-uncaging (Faal et al., 2015, Mol. Biosyst. 11: 783-790; Ballister et al., 2014, Nat. Comm. 5: 5475; Kobayashi et al., 2012, J. Am. Chem. Soc. 134: 11153-11160), photo-decomposition of azide (Lord et al., 2008, J. Am. Chem. Soc. 130: 9204-9205), or photoclick reactions (Lim and Lin, 2011, Accounts Chem. Res. 44: 828-839; Yu et al., 2011, J. Am. Chem. Soc. 133: 11912-11915; An et al., 2013, Org. Lett. 15: 5496-5499), to name a few. These strategies primarily depend on the activation from an initial non-fluorescent state to a fluorescent state.

Applications for fluorophores range from medicinal therapies to bioimaging to materials science and beyond (Kamkaew et al., 2013, Chem. Soc. Rev. 42: 77-88; Huang et al., 2012, Org. Lett. 14: 2594-2597; Zhang et al., 2011, Angew. Chem. Int. Ed. Eng. 50: 11654-11657; Yuan et al., 2012, J. Am. Chem. Soc. 134: 13510-13523; Lu et al., 2011, Angew. Chem. Int. Ed. Eng. 50: 11658-11662; Pansare et al., 2012, Chem. Mat. 24: 812-827; Law, 1993, Chem. Rev. 93: 449-486). Manipulation of known scaffolds such as cyanine (Mishra et al., 2000, Chem. Rev. 100: 1973-2011), BODIPY (Kamkaew et al., 2013, Chem. Soc. Rev. 42: 77-88; Lu et al., 2011, Angew. Chem. Int. Ed. Eng. 50: 11658-11662; Zhao and Carreira, 2005, Angew. Chem. Int. Ed. Eng. 44: 1677-1679, Loudet and Burgess, 2007, Chem. Rev. 107: 4891-4932), rhodamine (Zheng et al., 2013, Chem. Comm. 49: 429-447), squaraines (Avirah et al., 2012, Org. Biomol. Chem. 10: 911-920), porphyrins (Wang et al., 2013; Curr. Org. Chem. 17: 3078-3091), and napthylenediimides (Yuan et al., 2013, Chem. Soc. Rev. 42: 622-661) are commonplace in the literature.

Live cellular imaging of is one of the most powerful tools for increasing understanding of biological behavior, and its limitations primarily stem from a need for more effective imaging agents. A good subcellular stain incorporates an effective fluorophore and localizes with specificity. Designing a stain a priori involves the daunting challenge of trying to predict the various properties that are inherently associated with such efficacy, and also involves achieving and improving a multitude of properties:
1) Fluorescence
2) Water solubility and cell permeability
3) Non-toxicity
4) Red-shifted excitation and emission maxima
5) Stokes shift
6) Resistance to photobleaching
7) Compatibility with commonly used laser lines
8) Brightness
9) Site specific localization Moreover, in order to study the dynamics of biological processes, prolonged exposure to exciting light is sometimes unavoidable. Anti-fading agents have been developed to reduce bleaching. However, most are still fluorophore-dependent and mostly used for fixed specimens. As a result, photostability has become one of the most desirable properties of live-cell imaging dyes.

It is extremely difficult to make a compound that meets all of these requirements, and heretofore the ability to accurately predict most of these properties for a given molecule is also lacking. Even if such predictions were straightforward, many of these designs would also be synthetically undemanding to assemble and tune for greater efficacy. As such, it would be of great benefit to the bioimaging field if new imaging agents could be generated and evaluated much more rapidly.

Mitochondria are essential organelles in energy production and also involve in many other cellular activities such as differentiation, proliferation, and apoptosis. Some human neurodegenerative diseases like Alzheimer's and Parkinson's have also been correlated to mitochondrial dysfunction. Mitochondria morphologies can vary from rounded fragments to complex interconnected networks through fission and fusion. Visualizing and monitoring these dynamic organelles will shed light to many important cellular processes.

There is a need in the art for rapid and efficient methods for identifying new imaging agents. The present invention addresses and meets these needs.

SUMMARY OF THE INVENTION

The present invention relates to a composition comprising at least one compound of formula (I):

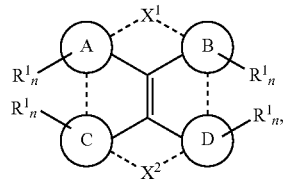

(I)

wherein in formula (I):

rings A, B, C, and D are each independently a monocyclic or bicyclic aryl or a monocyclic or bicyclic heteroaryl ring, and wherein the aryl or heteroaryl rings are each independently optionally substituted with 0-5 $R^1$ groups;

the bond between rings A and C and between rings B and D is each independently optional;

each occurrence of $R^1$ is independently selected from the group consisting of H, —$C_1$-$C_{20}$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)$OR^2$, —C(OH)($R^2$)$_2$, and —C($NH_2$)($R^2$)$_2$, wherein the alkyl group is optionally substituted;

each occurrence of $R^2$ is independently selected from the group consisting of H, $C_1$-$C_6$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$X^1$ and $X^2$ are each optional and each independently selected from the group consisting of O and S; and each occurrence of n is independently an integer from 0 to 4; and a salt, solvate, or N-oxide thereof, and any combinations thereof.

In one embodiment, the compound of formula (I) is at least one compound of formula (II):

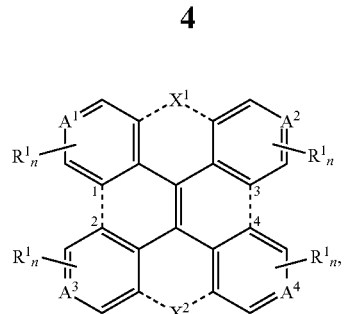

(II)

wherein in formula (II):

the bond between carbons 1 and 2 and between carbons 3 and 4 is each independently optional;

each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)$OR^2$, —C(OH)($R^2$)$_2$, and —C($NH_2$)($R^2$)$_2$;

each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$A^1$, $A^2$, $A^3$, and $A^4$ are each independently selected from the group consisting of $CR^2$, N, and

$X^1$ and $X^2$ are each optional and each independently selected from the group consisting of O and S;

with the proviso that at least one of $X^1$ and $X^2$ is present; and each occurrence of n is independently an integer from 0 to 4; and a salt, solvate, or N-oxide thereof, and any combinations thereof.

In one embodiment, the compound of formula (I) is at least one compound of formula (III):

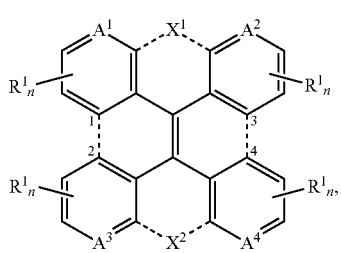

(III)

wherein in formula (III):

the bond between carbons 1 and 2 and between carbons 3 and 4 is each independently optional;

each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(═O)NH(R$^2$), —NHC(═O)R$^2$, —NHC(═O)OR$^2$, —C(OH)(R$^2$)$_2$, and —C(NH$_2$)(R$^2$)$_2$;

each occurrence of R$^2$ is independently selected from the group consisting of H, C$_1$-C$_{20}$ alkyl, aryl, C$_1$-C$_6$ heteroalkyl, and —C$_1$-C$_3$ alkyl-(C$_3$-C$_6$ cycloalkyl), wherein the alkyl, heteroalkyl or cycloalkyl group is optionally substituted;

A$^1$, A$^2$, A$^3$, and A$^4$ are each independently selected from the group consisting of CR$^2$, N, and $$\overset{\oplus}{N}R^2;$$

X$^1$ and X$^2$ are each optional and each independently selected from the group consisting of O and S;

with the proviso that at least one of X$^1$ and X$^2$ is present; and each occurrence of n is independently an integer from 0 to 4; and a salt, solvate, or N-oxide thereof, and any combinations thereof.

In one embodiment, the compound of formula (I) is at least one compound of formula (IV):

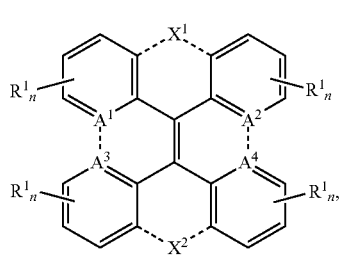

(IV)

wherein in formula (IV):

the bond between A$^1$ and A$^3$ and between A$^2$ and A$^4$ is each independently optional;

each occurrence of R$^1$ is independently selected from the group consisting of H, —C$_1$-C$_6$ alkyl, —C$_1$-C$_6$ fluoroalkyl, —C$_1$-C$_6$ heteroalkyl, F, Cl, Br, I, —CN, —NO$_2$, —OR$^2$, —SR$^2$, —S(═O)R$^2$, —S(═O)$_2$R$^2$, —NHS(═O)$_2$R$^2$, —C(═O)R$^2$, —OC(═O)R$^2$, —CO$_2$R$^2$, —OCO$_2$R$^2$, —CH(R$^2$)$_2$, —N(R$^2$)$_2$, —C(═O)N(R$^2$)$_2$, —OC(═O)N(R$^2$)$_2$, —NHC(═O)NH(R$^2$), —NHC(═O)R$^2$, —NHC(═O)OR$^2$, —C(OH)(R$^2$)$_2$, and —C(NH$_2$)(R$^2$)$_2$;

each occurrence of R$^2$ is independently selected from the group consisting of H, C$_1$-C$_{20}$ alkyl, aryl, C$_1$-C$_6$ heteroalkyl, and —C$_1$-C$_3$ alkyl-(C$_3$-C$_6$ cycloalkyl), wherein the alkyl, heteroalkyl or cycloalkyl group is optionally substituted;

A$^1$, A$^2$, A$^3$, and A$^4$ are each independently selected from the group consisting of CR$^2$, N, and $$\overset{\oplus}{N}R^2;$$

X$^1$ and X$^2$ are each optional and each independently selected from the group consisting of O and S;

with the proviso that at least one of X$^1$ and X$^2$ is present; and each occurrence of n is independently an integer from 0 to 4; and a salt, solvate, or N-oxide thereof, and any combinations thereof.

In one embodiment, the compound of formula (II) is selected from the group consisting of:

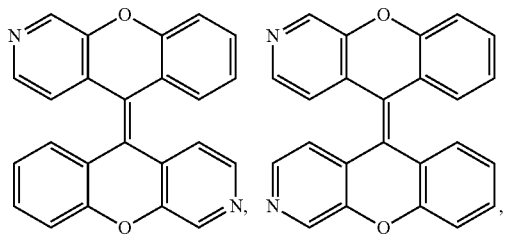

(E)-5,5'-bichromeno[2,3-c] pyridinylidene (Z)-5,5'-bichromeno[2,3-c] pyridinylidene

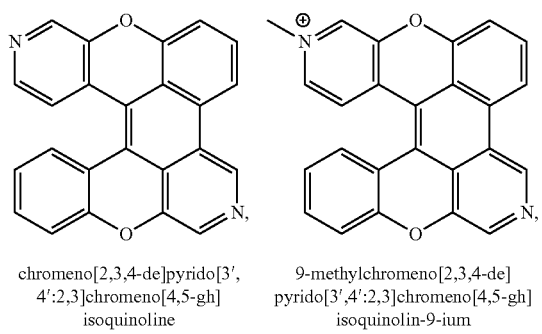

chromeno[2,3,4-de]pyrido[3', 4':2,3]chromeno[4,5-gh] isoquinoline 9-methylchromeno[2,3,4-de] pyrido[3',4':2,3]chromeno[4,5-gh] isoquinolin-9-ium

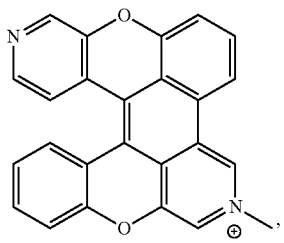

2-methylchromeno[2,3,4-de] pyrido[3',4':2,3]chromeno [4,5-gh]isoquinolin-2-ium

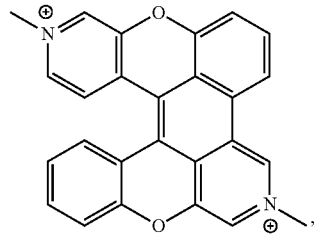

2,9-dimethylchromeno[2,3,4-de] pyrido[3',4':2,3]chromeno[4,5-gh] isoquinolin-2,9-diium

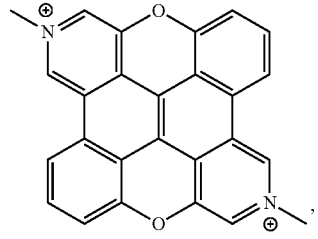

2,9-dimethyl-7,14-dioxa-2,9-diazaphenanthro[1,10,9,8-opqra] perylene-2,9-diium

-continued

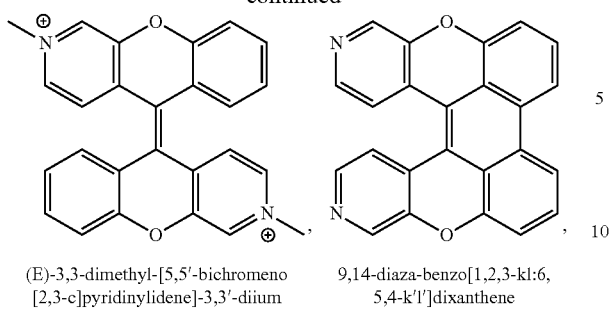

(E)-3,3-dimethyl-[5,5'-bichromeno
[2,3-c]pyridinylidene]-3,3'-diium 9,14-diaza-benzo[1,2,3-kl:6,
5,4-k'l']dixanthene

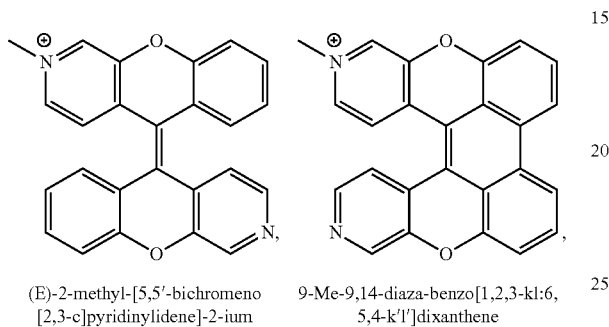

(E)-2-methyl-[5,5'-bichromeno
[2,3-c]pyridinylidene]-2-ium

9-Me-9,14-diaza-benzo[1,2,3-kl:6,
5,4-k'l']dixanthene

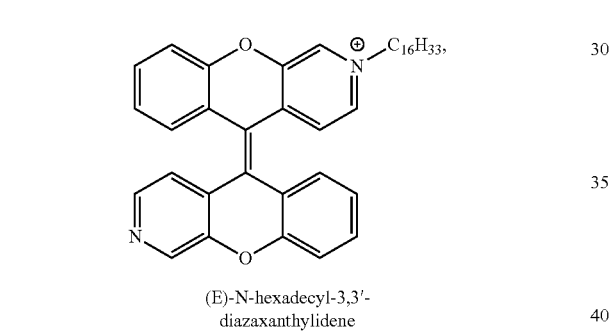

(E)-N-hexadecyl-3,3'-
diazaxanthylidene

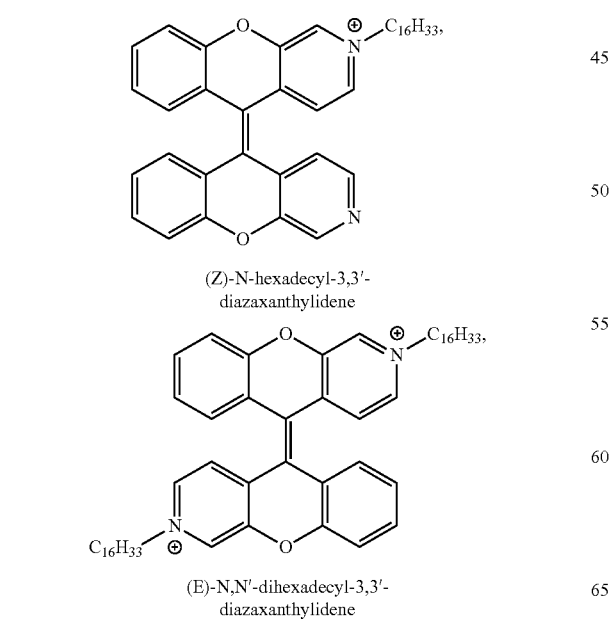

(Z)-N-hexadecyl-3,3'-
diazaxanthylidene (E)-N,N'-dihexadecyl-3,3'-
diazaxanthylidene -continued

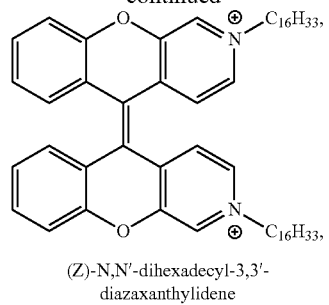

(Z)-N,N'-dihexadecyl-3,3'-
diazaxanthylidene

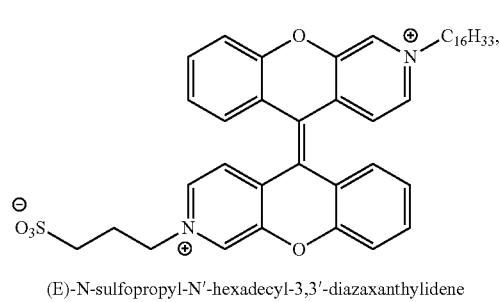

(E)-N-sulfopropyl-N'-hexadecyl-3,3'-diazaxanthylidene

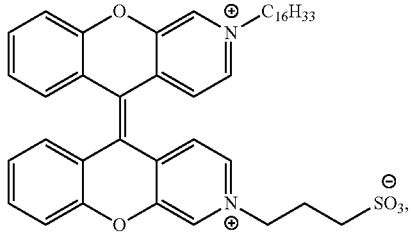

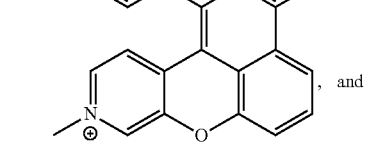

, and

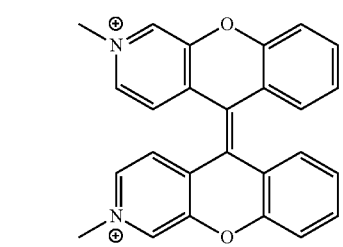

(Z)-N,-sulfopropyl-N'-hexadecyl-
3,3'-diazaxanthylidene mixtures thereof and salts thereof.

In one embodiment, the compound of formula (III) is selected from the group consisting of:

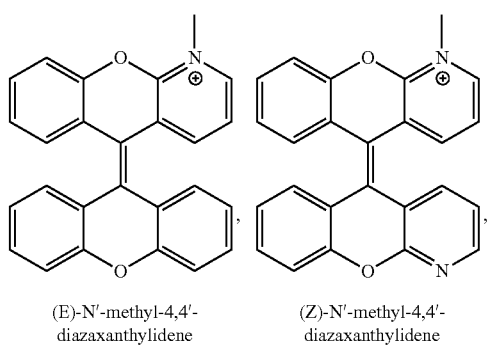

(E)-N'-methyl-4,4'-diazaxanthylidene, (Z)-N'-methyl-4,4'-diazaxanthylidene

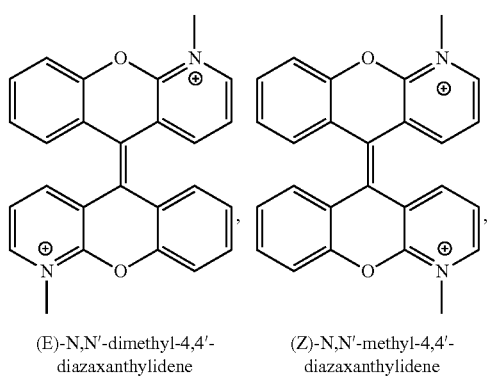

(E)-N,N'-dimethyl-4,4'-diazaxanthylidene, (Z)-N,N'-methyl-4,4'-diazaxanthylidene

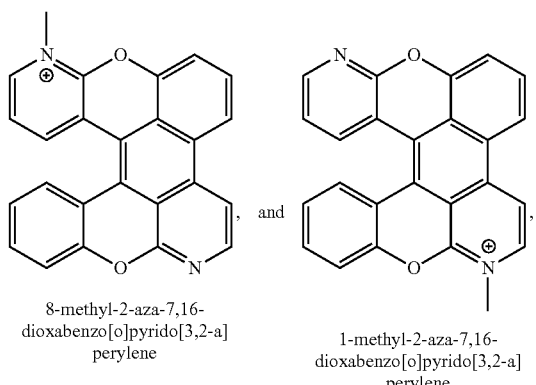

8-methyl-2-aza-7,16-dioxabenzo[o]pyrido[3,2-a]perylene, 1-methyl-2-aza-7,16-dioxabenzo[o]pyrido[3,2-a]perylene mixtures thereof and salts thereof.

In one embodiment, the compound of formula (IV) is selected from the group consisting of:

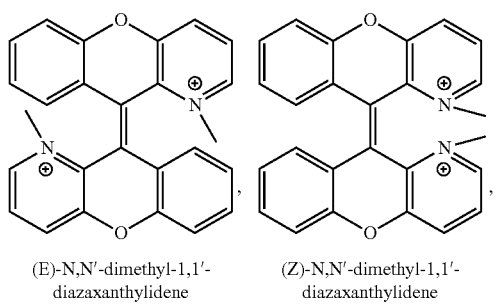

(E)-N,N'-dimethyl-1,1'-diazaxanthylidene, (Z)-N,N'-dimethyl-1,1'-diazaxanthylidene

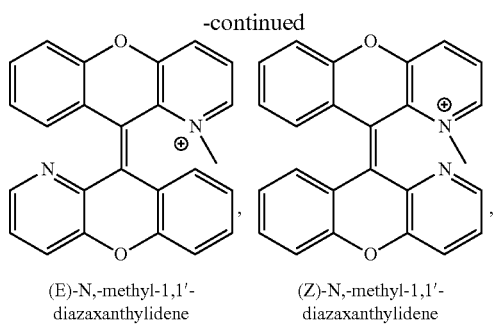

(E)-N,-methyl-1,1'-diazaxanthylidene, (Z)-N,-methyl-1,1'-diazaxanthylidene

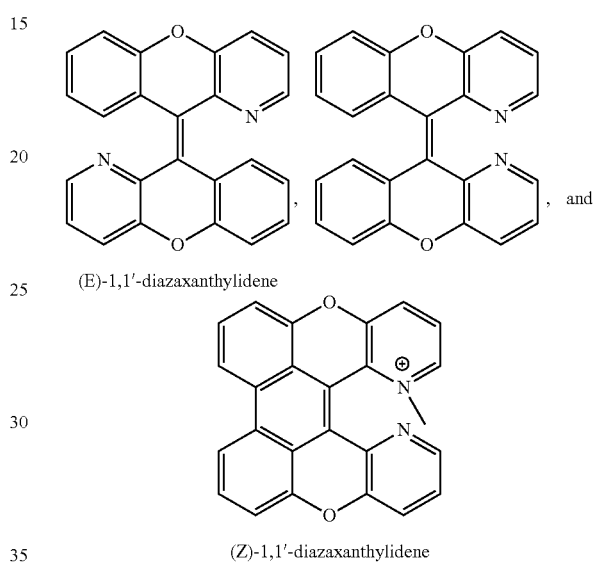

(E)-1,1'-diazaxanthylidene (Z)-1,1'-diazaxanthylidene mixtures thereof and salts thereof.

The present invention also relates to a method for identifying a compound as an imaging agent. The method includes the steps of providing a DAZAX-based scaffold or derivative thereof, modifying the scaffold to create a plurality of compounds, evaluating the plurality of compounds for bioimaging properties, and identifying a compound selected from the plurality of compounds as an imaging agent. In one embodiment, the method further includes the step of identifying selection criteria. In another embodiment, the method further includes the step of selecting a compound for use as an imaging agent in a bioimaging application based on the evaluation of the compound according to the selection criteria. In another embodiment, the step of modifying the scaffold comprises at least one modification selected from the group consisting of E-/Z-interconversion, methylation, photocyclization, electrophillic aromatic substitution, subsequent crosscoupling, nucleophillic aromatic substitution, and combinations thereof. In another embodiment, the selection criteria comprises the group consisting of fluorescence, water solubility, cell permeability, non-toxicity, red-shifted excitation and emission maxima, stokes shift, resistance to photobleaching, compatibility with laser lines, brightness, size specific location, and photoswitching. In another embodiment, the bioimaging application is selected from the group consisting of cell staining, fluorescence imaging, and CT scanning. In another embodiment the DAZAX-based scaffold is comprised of at least one compound selected from the group consisting of:

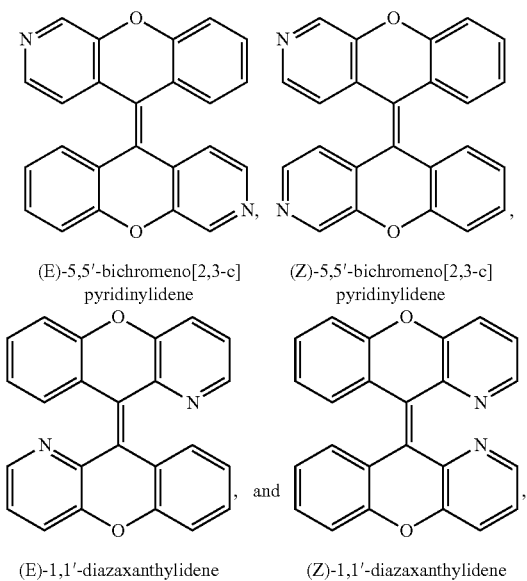

(E)-5,5'-bichromeno[2,3-c]pyridinylidene     (Z)-5,5'-bichromeno[2,3-c]pyridinylidene (E)-1,1'-diazaxanthylidene     (Z)-1,1'-diazaxanthylidene salts thereof, and mixtures thereof.

In one embodiment, the compound is at least one compound of formula (I):

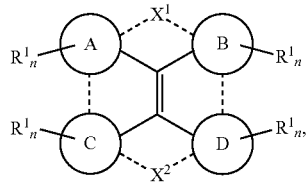

(I)

wherein in formula (I):

rings A, B, C, and D are each independently a monocyclic or bicyclic aryl or a monocyclic or bicyclic heteroaryl ring, and wherein the aryl or heteroaryl rings are each independently optionally substituted with 0-5 $R^1$ groups;

the bond between rings A and C and between rings B and D is each independently optional;

each occurrence of $R^1$ is independently selected from the group consisting of H, —$C_1$-$C_{20}$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$, wherein the alkyl group is optionally substituted;

each occurrence of $R^2$ is independently selected from the group consisting of H, $C_1$-$C_6$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$X^1$ and $X^2$ are each optional and each independently selected from the group consisting of O and S; and each occurrence of n is independently an integer from 0 to 4; and a salt, solvate, or N-oxide thereof, and any combinations thereof.

In one embodiment, the compound of formula (I) is at least one compound of formula (II):

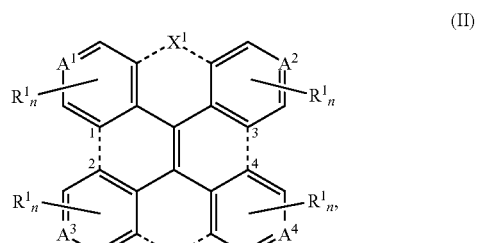

(II)

wherein in formula (II):

the bond between carbons 1 and 2 and between carbons 3 and 4 is each independently optional;

each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$;

each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$A^1$, $A^2$, $A^3$, and $A^4$ are each independently selected from the group consisting of $CR^2$, N, and

$X^1$ and $X^2$ are each optional and each independently selected from the group consisting of O and S;

with the proviso that at least one of $X^1$ and $X^2$ is present; and each occurrence of n is independently an integer from 0 to 4; and a salt, solvate, or N-oxide thereof, and any combinations thereof.

In one embodiment, the compound of formula (I) is at least one compound of formula (III):

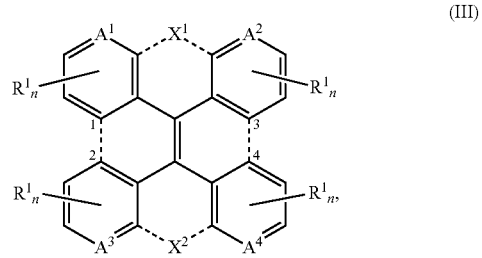

(III)

wherein in formula (III):

the bond between carbons 1 and 2 and between carbons 3 and 4 is each independently optional;

each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH(R$^2$), —NHC(=O)R$^2$, —NHC(=O)OR$^2$, —C(OH)(R$^2$)$_2$, and —C(NH$_2$)(R$^2$)$_2$;

each occurrence of R$^2$ is independently selected from the group consisting of H, C$_1$-C$_{20}$ alkyl, aryl, C$_1$-C$_6$ heteroalkyl, and —C$_1$-C$_3$ alkyl-(C$_3$-C$_6$ cycloalkyl), wherein the alkyl, heteroalkyl or cycloalkyl group is optionally substituted;

A$^1$, A$^2$, A$^3$, and A$^4$ are each independently selected from the group consisting of CR$^2$, N, and $$\overset{\oplus}{\text{NR}^2};$$

X$^1$ and X$^2$ are each optional and each independently selected from the group consisting of O and S;

with the proviso that at least one of X$^1$ and X$^2$ is present; and each occurrence of n is independently an integer from 0 to 4; and a salt, solvate, or N-oxide thereof, and any combinations thereof.

In one embodiment, the compound of formula (I) is at least one compound of formula (IV):

wherein in formula (IV):

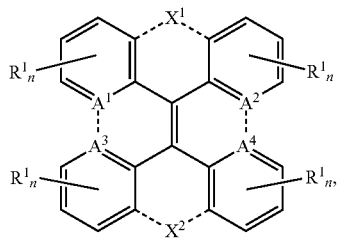

(IV)

the bond between A$^1$ and A$^3$ and between A$^2$ and A$^4$ is each independently optional;

each occurrence of R$^1$ is independently selected from the group consisting of H, —C$_1$-C$_6$ alkyl, —C$_1$-C$_6$ fluoroalkyl, —C$_1$-C$_6$ heteroalkyl, F, Cl, Br, I, —CN, —NO$_2$, —OR$^2$, —SR$^2$, —S(=O)R$^2$, —S(=O)$_2$R$^2$, —NHS(=O)$_2$R$^2$, —C(=O)R$^2$, —OC(=O)R$^2$, —CO$_2$R$^2$, —OCO$_2$R$^2$, —CH(R$^2$)$_2$, —N(R$^2$)$_2$, —C(=O)N(R$^2$)$_2$, —OC(=O)N(R$^2$)$_2$, —NHC(=O)NH(R$^2$), —NHC(=O)R$^2$, —NHC(=O)OR$^2$, —C(OH)(R$^2$)$_2$, and —C(NH$_2$)(R$^2$)$_2$;

each occurrence of R$^2$ is independently selected from the group consisting of H, C$_1$-C$_{20}$ alkyl, aryl, C$_1$-C$_6$ heteroalkyl, and —C$_1$-C$_3$ alkyl-(C$_3$-C$_6$ cycloalkyl), wherein the alkyl, heteroalkyl or cycloalkyl group is optionally substituted;

A$^1$, A$^2$, A$^3$, and A$^4$ are each independently selected from the group consisting of CR$^2$, N, and $$\overset{\oplus}{\text{NR}^2};$$

X$^1$ and X$^2$ are each optional and each independently selected from the group consisting of O and S;

with the proviso that at least one of X$^1$ and X$^2$ is present; and each occurrence of n is independently an integer from 0 to 4; and a salt, solvate, or N-oxide thereof, and any combinations thereof.

In one embodiment, the compound of formula (II) is selected from the group consisting of:

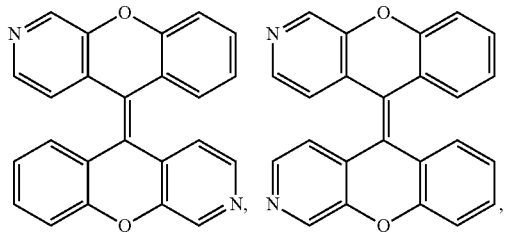

(E)-5,5'-bichromeno[2,3-c] pyridinylidene (Z)-5,5'-bichromeno[2,3-c] pyridinylidene

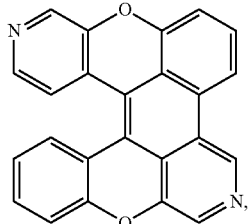

chromeno[2,3,4-de]pyrido[3', 4':2,3]chromeno[4,5-gh] isoquinoline 9-methylchromeno[2,3,4-de] pyrido[3',4':2,3]chromeno[4,5-gh] isoquinolin-9-ium

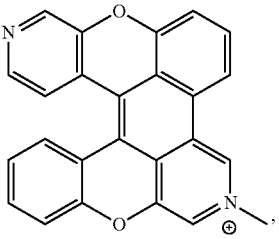

2-methylchromeno[2,3,4-de] pyrido[3',4':2,3]chromeno [4,5-gh]isoquinolin-2-ium

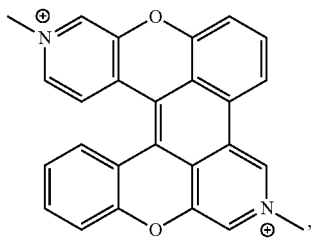

2,9-dimethylchromeno[2,3,4-de] pyrido[3',4':2,3]chromeno[4,5-gh] isoquinolin-2,9-diium

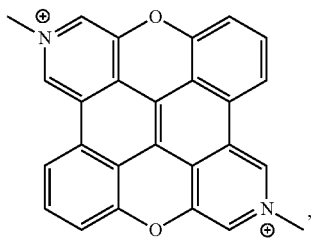

2,9-dimethyl-7,14-dioxa-2,9- diazaphenanthro[1,10,9,8-opqra] perylene-2,9-diium

-continued

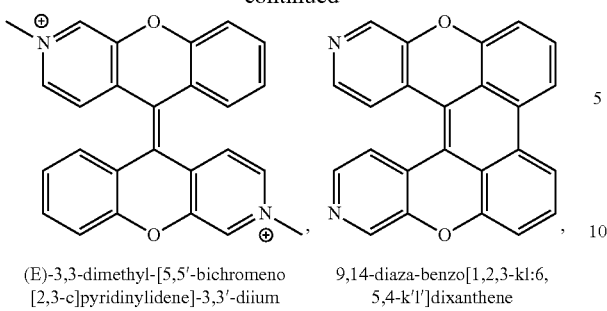

(E)-3,3-dimethyl-[5,5'-bichromeno
[2,3-c]pyridinylidene]-3,3'-diium 9,14-diaza-benzo[1,2,3-kl:6,
5,4-k'l']dixanthene

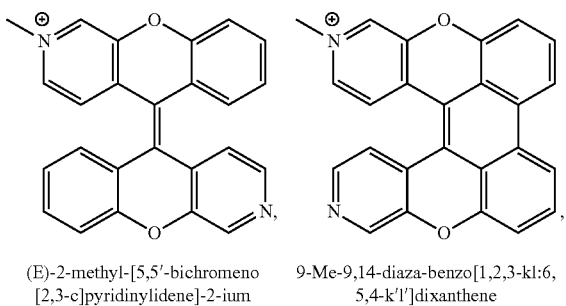

(E)-2-methyl-[5,5'-bichromeno
[2,3-c]pyridinylidene]-2-ium

9-Me-9,14-diaza-benzo[1,2,3-kl:6,
5,4-k'l']dixanthene

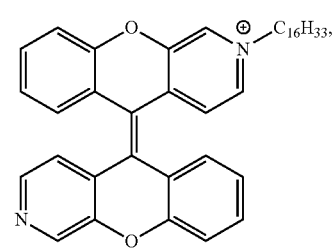

(E)-N-hexadecyl-3,3'-
diazaxanthylidene

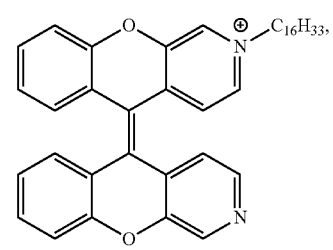

(Z)-N-hexadecyl-3,3'-
diazaxanthylidene

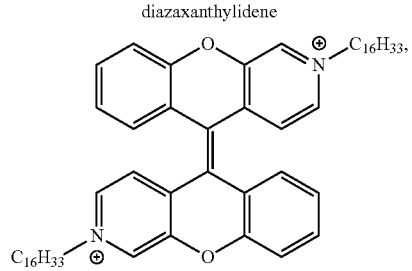

(E)-N,N'-dihexadecyl-3,3'-
diazaxanthylidene

-continued

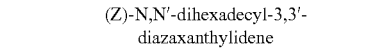

(Z)-N,N'-dihexadecyl-3,3'-
diazaxanthylidene

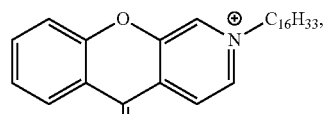

(E)-N-sulfopropyl-N'-hexadecyl-3,3'-diazaxanthylidene

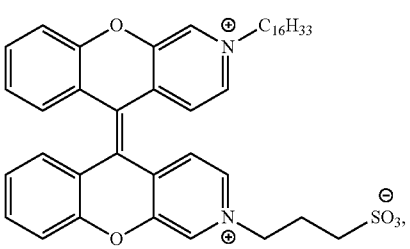

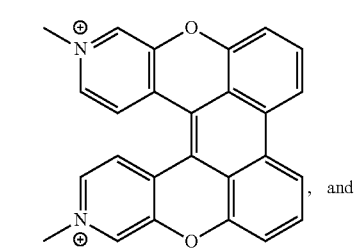

, and

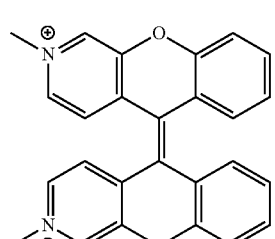

(Z)-N,-sulfopropyl-N'-hexadecyl-
3,3'-diazaxanthylidene mixtures thereof and salts thereof.

In one embodiment, the compound of formula (III) is selected from the group consisting of:

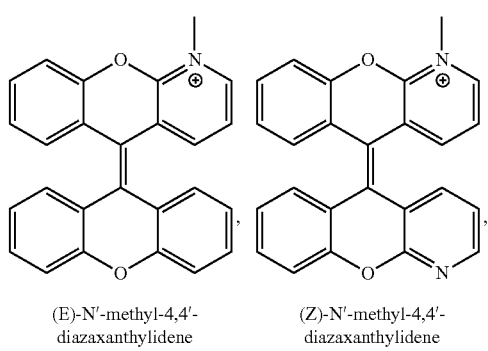

(E)-N'-methyl-4,4'-diazaxanthylidene (Z)-N'-methyl-4,4'-diazaxanthylidene

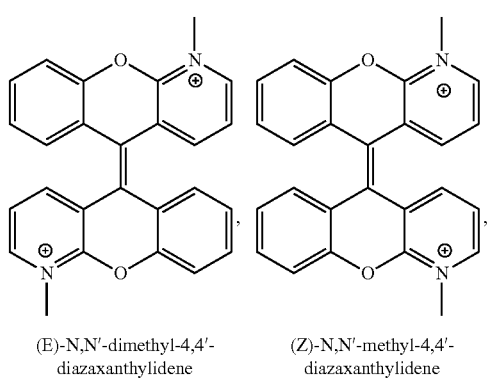

(E)-N,N'-dimethyl-4,4'-diazaxanthylidene (Z)-N,N'-methyl-4,4'-diazaxanthylidene

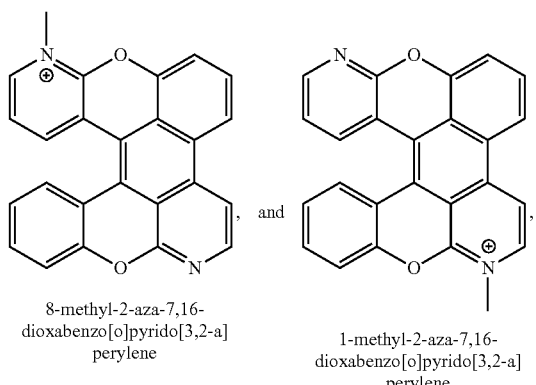

8-methyl-2-aza-7,16-dioxabenzo[o]pyrido[3,2-a]perylene 1-methyl-2-aza-7,16-dioxabenzo[o]pyrido[3,2-a]perylene mixtures thereof and salts thereof.

In one embodiment, the compound of formula (IV) is selected from the group consisting of:

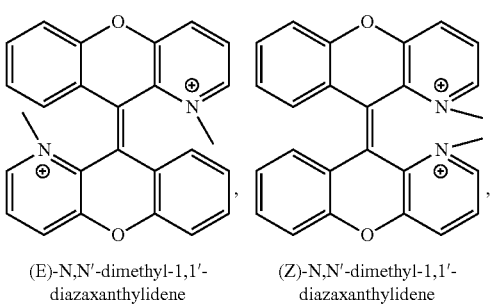

(E)-N,N'-dimethyl-1,1'-diazaxanthylidene (Z)-N,N'-dimethyl-1,1'-diazaxanthylidene

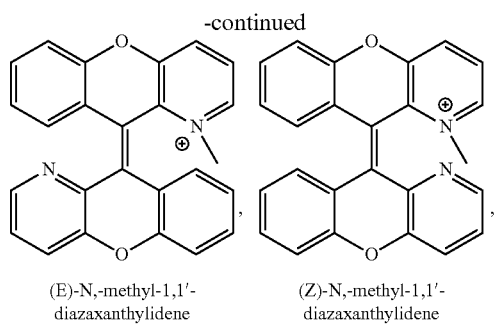

(E)-N,-methyl-1,1'-diazaxanthylidene (Z)-N,-methyl-1,1'-diazaxanthylidene

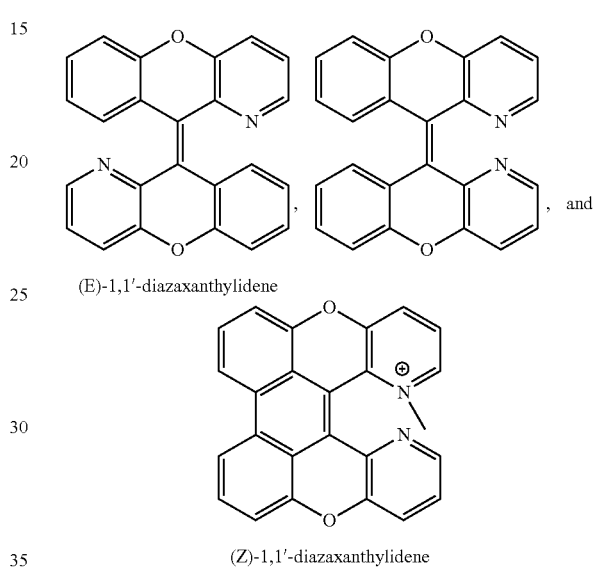

(E)-1,1'-diazaxanthylidene

, and (Z)-1,1'-diazaxanthylidene mixtures thereof and salts thereof.

The present invention also provides a method of modifying a DAZAX-based scaffold or derivatives thereof. The method includes the step of irradiating the scaffold. In one embodiment, the scaffold is irradiated using a wavelength of about 365 nm. In one embodiment, the method further includes the step of alkylating the scaffold. In another embodiment, the step of alkylating the scaffold occurs prior to the step of irradiating the scaffold. In another embodiment, the step of alkylating the scaffold occurs after the step of irradiating the scaffold. In another embodiment, the step of alkylating the scaffold is methylation of the scaffold. In another embodiment, the DAZAX-based scaffold is comprised of at least one compound selected from the group consisting of:

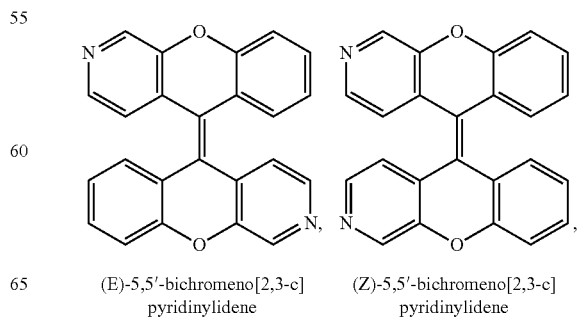

(E)-5,5'-bichromeno[2,3-c]pyridinylidene (Z)-5,5'-bichromeno[2,3-c]pyridinylidene

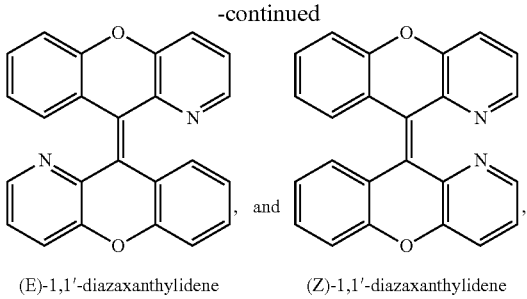

(E)-1,1'-diazaxanthylidene                (Z)-1,1'-diazaxanthylidene salts thereof, and mixtures thereof.

The present invention also includes a method for imaging a sample. The method includes providing a sample, contacting the sample with an imaging agent, irradiating the sample with an excitation wavelength range, and detecting fluorescence of the sample, thereby imaging the sample. In one embodiment, at least a portion of the sample exhibits increased fluorescence after the contacting step compared to before the contacting step. In another embodiment, the irradiation has an excitation wavelength range of about 375 nm to about 450 nm. In another embodiment, only a portion of the sample is irradiated. In another embodiment, the imaging agent is selected from the group consisting of

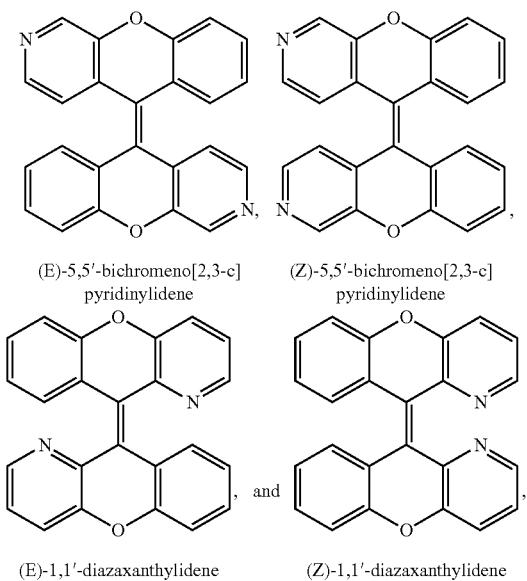

(E)-5,5'-bichromeno[2,3-c]pyridinylidene    (Z)-5,5'-bichromeno[2,3-c]pyridinylidene (E)-1,1'-diazaxanthylidene                (Z)-1,1'-diazaxanthylidene salts thereof, and mixtures thereof. In another embodiment, the sample is a cell. In another embodiment, the cell is a live cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 3A-3C, is an illustration of compounds 1 (both E and Z configurations), 2, and 3. FIG. 3A is a scheme depicting the synthesis of compounds 2 and 3 by irradiation of a THF solution of 3,3'-diazaxanthylidene (3,3'-DAZAX) (compound 1) with 365 nm light for 26 hours in the presence of propylene oxide and iodine. FIG. 3B is an illustration of the crystal structure of compound E-1. FIG. 3C is an illustration of the crystal structure of compound 2.

FIGS. 6A-6B, depicts a comparison between the HPLC trace of products produced using photolysis followed by methylation versus methylation followed by photolysis. FIG. 6A is a HPLC trace of products produced using photolysis followed by methylation. FIG. 6B is a HPLC trace of products produced using methylation followed by photolysis.

FIGS. 30A-30C, depicts the structure (FIG. 30A), absorption spectrum (Abs) and emission spectrum (Em) (FIG. 30B), and cell staining images (FIG. 30C) of (E)-N-hexadecyl-3,3'-diazaxanthylidene or (Z)—N-hexadecyl-3,3'-diazaxanthylidene, compounds useful in the invention.

FIGS. 31A-31C, depicts the structure (FIG. 31A), absorption spectrum (Abs) and emission spectrum (Em) (FIG. 31B), and cell staining images (FIG. 31C) of (E)-N,N'-dihexadecyl-3,3'-diazaxanthylidene or (Z)—N,N'-dihexadecyl-3,3'-diazaxanthylidene, compounds useful in the invention.

FIGS. 32A-32C, depicts the structure (FIG. 32A), absorption spectrum (Abs) and emission spectrum (Em) (FIG. 32B), and cell staining images (FIG. 32C) of (E)-N-sulfopropyl-V-hexadecyl-3,3'-diazaxanthylidene or (Z)—N-sulfopropyl-N'-hexadecyl-3,3'-diazaxanthylidene, compounds useful in the invention.

FIGS. 33A-33C, depicts the structure (FIG. 33A), absorption spectrum (Abs) and emission spectrum (Em) (FIG. 33B), and cell staining images (FIG. 33C) of (E)-N'-methyl-4,4'-diazaxanthylidene or (Z)—N'-methyl-4,4'-diazaxanthylidene, compounds useful in the invention.

FIGS. 34A-34C, depicts the structure (FIG. 34A), absorption spectrum (Abs) and emission spectrum (Em) (FIG. 34B), and cell staining images (FIG. 34C) of (E)-N,N'-dimethyl-4,4'-diazaxanthylidene or (Z)—N,N'-dimethyl-4,4'-diazaxanthylidene, compounds useful in the invention.

FIGS. 35A-35C, depicts the structure (FIG. 35A), absorption spectrum (Abs) and emission spectrum (Em) (FIG. 35B), and cell staining images (FIG. 35C) of 8-methyl-2-aza-7,16-dioxabenzo[o]pyrido[3,2-a]perylene or 1-methyl-2-aza-7,16-dioxabenzo[o]pyrido[3,2-a]perylene, compounds useful in the invention.

FIGS. 36A-36C, depicts the structure (FIG. 36A), absorption spectrum (Abs) and emission spectrum (Em) (FIG. 36B), and cell staining images (FIG. 36C) of (E)-N,N'-dihexadecyl-3,3'-diazaxanthylidene or (Z)—N,N'-dihexadecyl-3,3'-diazaxanthylidene, compounds useful in the invention.

FIGS. 37A-37C, depicts the structure (FIG. 37A), excitation spectrum (Ex) and emission spectrum (Em) (FIG. 37B), and cell staining images (FIG. 37C) of (E)-N,N'-dimethyl-1,1'-diazaxanthylidene or (Z)—N,N'-dimethyl-1,1'-diazaxanthylidene, compounds useful in the invention.

FIGS. 38A-38C, depicts the structure (FIG. 38A), excitation spectrum (Ex) and emission spectrum (Em) (FIG. 38B), and cell staining images (FIG. 38C) of (E)-N-methyl-1,1'-diazaxanthylidene or (Z)—N-methyl-1,1'-diazaxanthylidene, compounds useful in the invention.

FIG. 39A is an exemplary synthetic scheme demonstrating The Mallory reaction of E/Z-1 to provide compounds DiMe-3 (from E-1) and DiMe-2 (from Z-1). FIG. 39B is an image of the antifolded crystal structure of E-1.

FIG. 40A is a graph depicting the absorption spectra of fluorophores E/Z-1, 2, 3, DiMe-3, DiMe-2, DiMe-Z-1, and DiMe-E-1.

FIGS. 41A-41E, depicts confocal microscopy images of live cell imaging with exemplary compounds. FIG. 41A is an image of compound 3 staining mitochondria. FIG. 41B is an image of compound 2 staining mitochondria. FIG. 41C is an image of compound DiMe-3 staining lysosomes.

FIG. 44A is a scheme depicting the E-Z interconversion and photocyclization/oxidation reaction of 11-E/Z. FIG. 44B is an illustration of the idealized and calculated LUMO of 11-Z (method: TD-DFT B3LYP, basis set=6–311+G(2d,p)). The orbitals were preorganized for photochemically favored conrotatory cyclization. FIG. 44C is a graph depicting the absorbance and emission spectra of 11-E/11-Z (Abs$\lambda_{max}$=408 nm, Em $\lambda_{max}$=543 nm, ε=11040 M$^{-1}$cm$^{-1}$, (Φ=0.021) and 12 (Abs$\lambda_{max}$=504 nm, Em $\lambda_{max}$=612 nm, ε=11496 M$^{-1}$cm$^{-1}$, Φ=0.100) in water.

FIG. 45A is a series of confocal images of mito-GFP cells (right panel), HeLa cells stained with 11-E/11-Z (middle panel), and mito-GFP cells stained with 11-E/11-Z (left panel). Compound 11-E/11-Z was observed at 405/635 while GFP was observed at 488/525. No bleed-through was detected. All images were kept at the same contrast/brightness. Scale bar=10 μm. FIG. 45B is a line plot of fluorescence intensity across multiple cells showing high colocalization and signal to noise ratio for both GFP and 11-E/11-Z. "n" was used to indicate the area of the nucleus. Pearson's colocolzation coefficient was 0.87±0.01. Manders' overlap coefficients were 0.98±0.01 and 1.00±0.00. FIG. 45C is an HPLC chromatogram of 11-E/11-Z (1 mM solution in water) after 10 days under ambient light (top chromatogram) and HPLC chromatogram of 12 (bottom chromatogram). No decomposition or photoproduct of 11-E/11-Z was detected. FIG. 45D is a graph depicting experimental data of a cell viability test in HeLa cells of 11-E/11-Z and MitoTracker Red FM at working concentration for imaging (5 μM for 11-E/11-Z and 1 μM for MitoTracker Red FM).

FIG. 46A is a series of confocal microscopy images of HeLa cells stained with 11-E/11-Z, observed at 444/525 and 488/632 over 30 seconds with 200 alternating 150 ms pulses. FIG. 46B is a graph of average intensity of channels 444/525 and 488/632 after 200 alternating pulses. The data from each of the two channels were fitted to a one phase exponential curve and the obtained rate constant and half-life were 0.060 s$^{-1}$ and 11.61 s for the 444/525 channel and 0.030 s$^{-1}$ and 23.05 s for the 488/632 channel. FIG. 46C is a graph of average intensity of cells 1 and 2 before and after activation. FIG. 46D is a series of images of selective sequential photoactivation of two cells (7 and 19) among a field of view containing 20 confluent cells. Each cell was activated by 50 20-second pulses of a normal 405 nm FRAP laser. Dashed lines indicate cells boundary, determined by differential interference contrast images. Scale bar=10 μm.

FIG. 47A is a synthetic scheme of an exemplary photocyclization/oxidation reaction of E-1/Z-1 to provide photoproducts 2 and 3. FIG. 47B is an image of the crystal structures of E-1. FIG. 47C is an image of the crystal structure of 2.

FIG. 48A is an image of an optimized structure of E-1. FIG. 48B is an image of the calculated HOMO of E-1. Out-of-phase interaction leads to thermally disallowed electrocyclization. FIG. 48C is an image of the calculated HOMO* (or LUMO) of E-1. In-phase interaction leads to photochemically allowed electrocyclization.

FIG. 49A is an absorption spectra of E-1/Z-1, 2, and 3 in chloroform. FIG. 49B is an emission spectra of E-1/Z-1, 2, and 3 in chloroform. FIG. 49C is a table of experimentally measured photophysical properties of E-1/Z-1, 2, and 3.

FIG. 50A is a series of confocal microscopy images of HELA cells stained with compound 3 and Hoechst 33342. FIG. 50B is a series of confocal microscopy images of HELA cells stained with compound 2 and Hoechst 33342.

FIG. 52 is an exemplary synthetic scheme for the preparation of compounds 11-E and 11-Z.

FIG. 54A is a confocal image of the cells using channel 405/635 to detect 11-E/11-Z. FIG. 54B is a confocal image of the cells using channel 488/525 to detect GFP. FIG. 54C is a merged image of FIGS. 54A and 54B. FIG. 54D is a colocalized pixel map, white: colocalized, red: 11-E/11-Z only, green: GFP only. Scale bar=10 μm.

FIG. 55A is a series of confocal images of mito-GFP cells (right panel), HeLa cells stained with MitoTracker Red FM (middle panel), and mito-GFP cells and non-GFP cells stained with MitoTracker Red FM (left panel). MitoTracker Red FM was observed at 638/675 while GFP was observed at 488/525. No bleed-through was detected. All images were kept at the same contrast/brightness. Scale bar=10 μm. FIG. 55B is a graph of the line plot of fluorescence intensity across multiple cells. "n" was used to indicate the area of the nucleus. Pearson's colocolzation coefficient was 0.92±0.02. Manders' overlap coefficients were 0.99±0.01 and 1.00±0.00.

FIG. 59A is a $^1$H NMR spectrum of S4. FIG. 59B is a $^{13}$C NMR spectrum of S4.

FIG. 60A is a $^1$H NMR spectrum of thioketone 1. FIG. 60B is a $^{13}$C NMR spectrum of thioketone 1.

FIG. 61A is a $^1$H NMR spectrum of 10-E/10-Z. FIG. 61B is a $^{13}$C NMR spectrum of 10-E/10-Z.

FIG. 62A is a $^1$H NMR spectrum of 11-E/11-Z. FIG. 62B is a $^{13}$C NMR spectrum of 11-E/11-Z.

FIG. 63A is a $^1$H NMR spectrum of 12. FIG. 63B is a $^{13}$C NMR spectrum of 12.

DETAILED DESCRIPTION OF THE INVENTION

Figure 1:
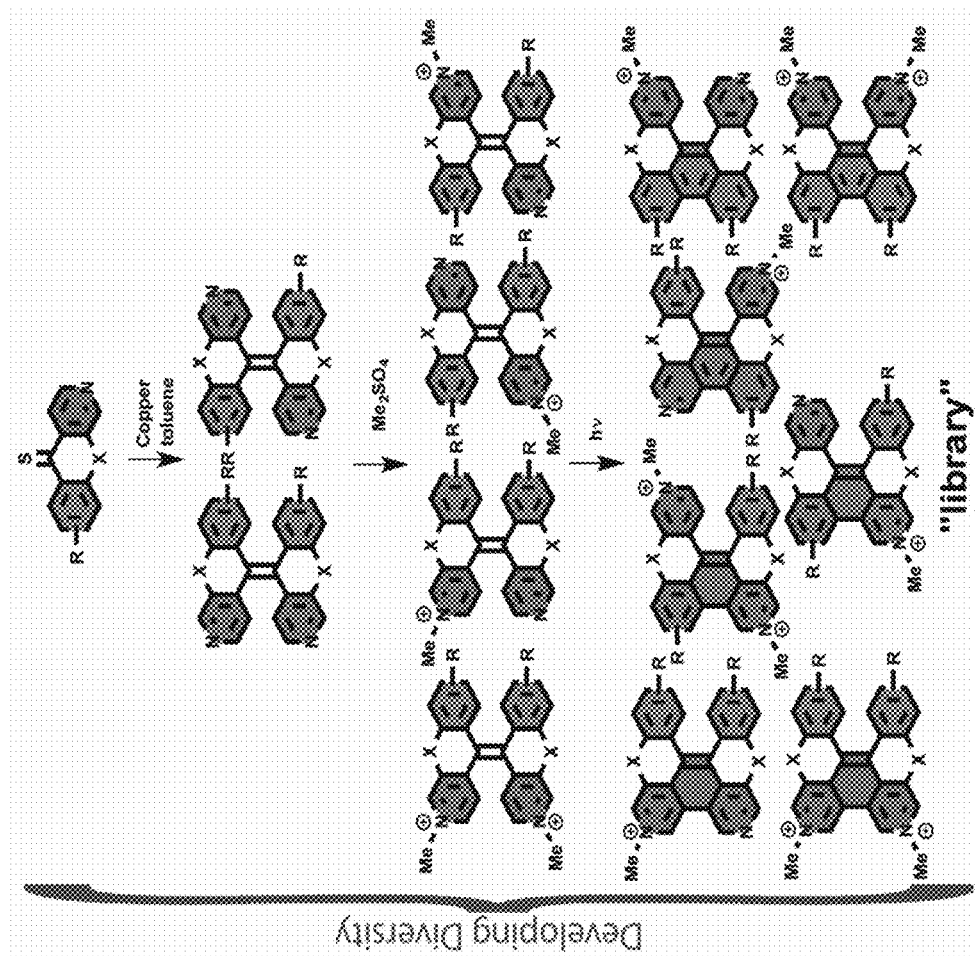
FIG. 1 is an illustration of the development of a diverse library of compounds following dimerization, methylation, and photolysis.

It is to be understood that the figures and descriptions of the present invention have been simplified to illustrate elements that are relevant for a clear understanding of the present invention, while eliminating, for the purpose of clarity, many other elements found in the art related to organic chemistry, fluorescent compounds, bioimaging, imaging agents, and the like. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Although any methods, materials and components similar or equivalent to those described herein can be used in the practice or testing of the present invention, the preferred methods and materials are described.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

As used herein, a "solvate" of a molecule refers to a complex between the molecule and a finite number of solvent molecules. In one embodiment, the solvate is a solid isolated from solution by precipitation or crystallization. In another embodiment, the solvate is a hydrate.

As used herein, a "subject" may be a human or non-human mammal or a bird. Non-human mammals include, for example, livestock and pets, such as ovine, bovine, porcine, canine, feline and murine mammals. Preferably, the subject is human.

By the term "specifically bind" or "specifically binds," as used herein, is meant that a first molecule preferentially binds to a second molecule (e.g., a particular receptor or enzyme), but does not necessarily bind only to that second molecule. The terms "inhibit" and "antagonize", as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

In one embodiment, the substituents are independently selected from the group consisting of oxo, halogen, —CN, —$NH_2$, —OH, —NH($CH_3$), —N($CH_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —SO$_3$H, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions of fluorescent reagents, methods for producing such reagents, and methods for screening compounds useful as imaging agents. The compositions of the present invention are based on the diazaxanthylidene (DAZAX) scaffold. These DAZAX-derived compounds exhibit desirable photostability and cell permeability properties useful for biological imaging applications.

In one embodiment, the method of the present invention is a high-throughput screening method for identifying compounds that are useful as imaging agents By combining a modular synthetic approach with a subsequent high throughput evaluation process, a method of discovering photostable compounds displaying desirable characteristics has been developed. In one aspect, the methods of the invention allow for the discovery and development of new imaging agents by focusing on identifying or selecting for desirable properties required for any application.

The present invention further includes compounds identified as imaging agents using the screening methods of the invention. Using the method of the present invention, several cell-permeable, fluorescent compounds useful for cell staining have been identified, including compounds useful as stains specific for certain cell organelles. In a non-limiting example, monomethylated 3,3'-diazaxanthylidene (3,3'-DAZAX, Me-2) was identified as a selective lysosomal stain in HeLa cells. The photostability of Me-2 was found to be superior to the current technology available in the marketplace.

Compositions

The compositions of the present invention are generally compounds derived from DAZAX. In one embodiment, the DAZAX scaffold is a 3,3'-diazaxanthylidene (3,3'-DAZAX) scaffold. In another embodiment, the DAZAX scaffold is a 1,1'-diazaxanthylidene (1,1'-DAZAX) scaffold. In another embodiment, the DAZAX scaffold is a 2,2'-diazaxanthylidene (2,2'-DAZAX) scaffold. In another embodiment, the DAZAX scaffold is a 4,4'-diazaxanthylidene (4,4'-DAZAX) scaffold. The compounds include compounds identified using the methods described herein. In one embodiment, the compound of the present invention is useful as an imaging agent. In another embodiment, the compound is a fluorescent compound. In yet another embodiment, the compound of the present invention is a small molecule. However, the compounds of the present invention are not limited to those recited specifically herein.

Small Molecules

When the compound identified by the method of the present invention is a small molecule, the small molecule may be obtained using standard methods known to the skilled artisan. Such methods include chemical organic synthesis or biological means. Biological means include purification from a biological source, recombinant synthesis and in vitro translation systems, using methods well known in the art.

In one aspect, the compound of the invention is a compound of formula (I), or a salt, solvate, or N-oxide thereof:

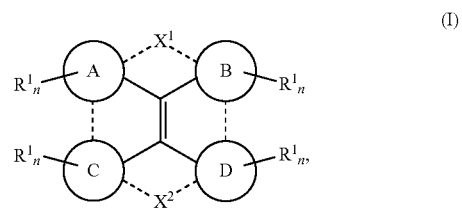

wherein in formula (I):
rings A, B, C, and D are each independently a monocyclic or bicyclic aryl or a monocyclic or bicyclic heteroaryl ring, and wherein the aryl or heteroaryl rings are each independently optionally substituted with 0-5 R$^1$ groups;
the bond between rings A and C and between rings B and D is each independently optional;
each occurrence of R$^1$ is independently selected from the group consisting of H, —C$_1$-C$_{20}$ alkyl, —C$_1$-C$_6$ fluoroalkyl, —C$_1$-C$_6$ heteroalkyl, F, Cl, Br, I, —CN, —NO$_2$, —OR$^2$, —SR$^2$, —S(=O)R$^2$, —S(=O)$_2$R$^2$, —NHS(=O)$_2$R$^2$, —C(=O)R$^2$, —OC(=O)R$^2$, —CO$_2$R$^2$, —OCO$_2$R$^2$, —CH(R$^2$)$_2$, —N(R$^2$)$_2$, —C(=O)N(R$^2$)$_2$, —OC(=O)N(R$^2$)$_2$, —NHC(=O)NH(R$^2$), —NHC(=O)R$^2$, —NHC(=O)OR$^2$, —C(OH)(R$^2$)$_2$, and —C(NH$_2$)(R$^2$)$_2$, wherein the alkyl group is optionally substituted;
each occurrence of R$^2$ is independently selected from the group consisting of H, C$_1$-C$_6$ alkyl, aryl, C$_1$-C$_6$ heteroalkyl, and —C$_1$-C$_3$ alkyl-(C$_3$-C$_6$ cycloalkyl), wherein the alkyl, heteroalkyl or cycloalkyl group is optionally substituted;

$X^1$ and $X^2$ are each optional and each independently selected from the group consisting of O and S; and each occurrence of n is independently an integer from 0 to 4.

In one embodiment, rings A and D are pyridinyl, rings B and C are phenyl, and $X^1$ and $X^2$ are each O.

In another embodiment, rings A and C are pyridinyl, rings B and D are phenyl, and $X^1$ and $X^2$ are each O.

In another embodiment, rings A and D are pyridinyl, rings B and C are phenyl, $X^1$ and $X^2$ are each O, and the bond between rings B and D is present.

In another embodiment, rings A and D are pyridinyl, rings B and C are phenyl, $X^1$ and $X^2$ are each O, and the bonds between rings A and C and rings B and D are present.

In another embodiment, at least one of rings A, B, C, and D is pyridinyl, wherein the nitrogen atom of at least one pyridinyl group is substituted with a $C_1$-$C_{20}$ alkyl group, forming a quaternary nitrogen atom.

In another aspect, the compound of the invention is a compound of formula (II), or a salt, solvate, or N-oxide thereof:

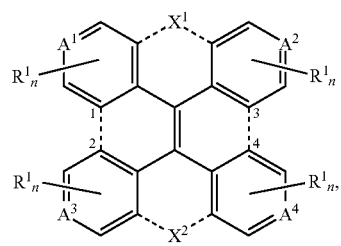

(II)

wherein in formula (II):
the bond between carbons 1 and 2 and between carbons 3 and 4 is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$;
each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;
$A^1$, $A^2$, $A^3$, and $A^4$ are each independently selected from the group consisting of $CR^2$, N, and $$\overset{\oplus}{N}R^2;$$

$X^1$ and $X^2$ are each optional and each independently selected from the group consisting of O and S;
with the proviso that at least one of $X^1$ and $X^2$ is present; and
each occurrence of n is independently an integer from 0 to 4.

In another aspect, the compound of the invention is a compound of formula (III), or a salt, solvate, or N-oxide thereof:

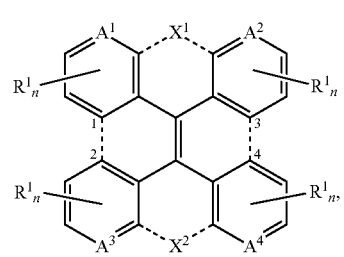

(III)

wherein in formula (III):
the bond between carbons 1 and 2 and between carbons 3 and 4 is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$;
each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;
$A^1$, $A^2$, $A^3$, and $A^4$ are each independently selected from the group consisting of $CR^2$, N, and $$\overset{\oplus}{N}R^2;$$

$X^1$ and $X^2$ are each optional and each independently selected from the group consisting of O and S;
with the proviso that at least one of $X^1$ and $X^2$ is present; and
each occurrence of n is independently an integer from 0 to 4.

In another aspect, the compound of the invention is a compound of formula (IV), or a salt, solvate, or N-oxide thereof:

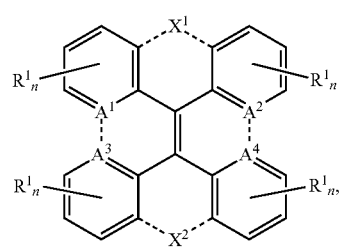

(IV)

wherein in formula (IV):
the bond between $A^1$ and $A^3$ and between $A^2$ and $A^4$ is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, Cl, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —OCO$_2$R$^2$, —CH(R$^2$)$_2$, —N(R$^2$)$_2$, —C(=O)N(R$^2$)$_2$, —OC(=O)N(R$^2$)$_2$, —NHC(=O)NH(R$^2$), —NHC(=O)R$^2$, —NHC(=O)OR$^2$, —C(OH)(R$^2$)$_2$, and —C(NH$_2$)(R$^2$)$_2$;

each occurrence of R$^2$ is independently selected from the group consisting of H, C$_1$-C$_{20}$ alkyl, aryl, C$_1$-C$_6$ heteroalkyl, and —C$_1$-C$_3$ alkyl-(C$_3$-C$_6$ cycloalkyl), wherein the alkyl, heteroalkyl or cycloalkyl group is optionally substituted;

A$^1$, A$^2$, A$^3$, and A$^4$ are each independently selected from the group consisting of CR$^2$, N, and $$\overset{\oplus}{N}R^2;$$

X$^1$ and X$^2$ are each optional and each independently selected from the group consisting of O and S;

with the proviso that at least one of X$^1$ and X$^2$ is present; and each occurrence of n is independently an integer from 0 to 4.

In one embodiment, the compound of formula (II) is selected from the group consisting of:

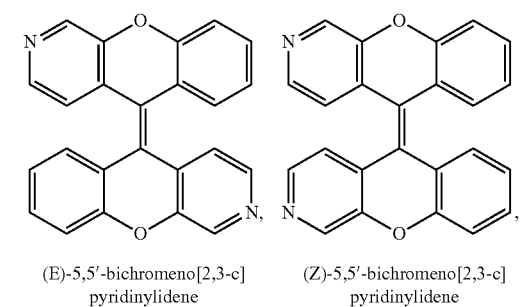

(E)-5,5'-bichromeno[2,3-c]pyridinylidene (Z)-5,5'-bichromeno[2,3-c]pyridinylidene

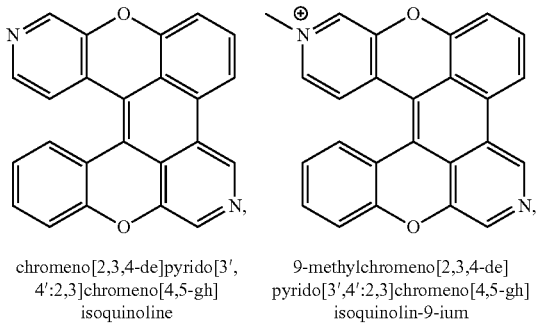

chromeno[2,3,4-de]pyrido[3',4':2,3]chromeno[4,5-gh]isoquinoline 9-methylchromeno[2,3,4-de]pyrido[3',4':2,3]chromeno[4,5-gh]isoquinolin-9-ium

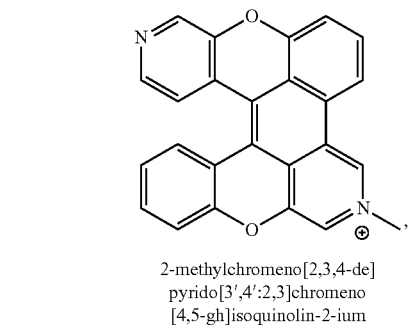

2-methylchromeno[2,3,4-de]pyrido[3',4':2,3]chromeno[4,5-gh]isoquinolin-2-ium

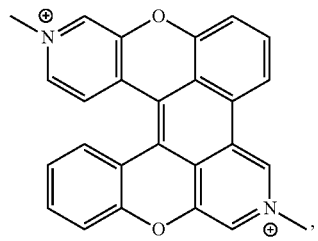

2,9-dimethylchromeno[2,3,4-de]pyrido[3',4':2,3]chromeno[4,5-gh]isoquinolin-2,9-diium

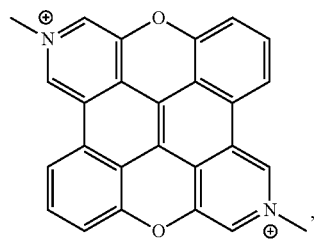

2,9-dimethyl-7,14-dioxa-2,9-diazaphenanthro[1,10,9,8-opqra]perylene-2,9-diium

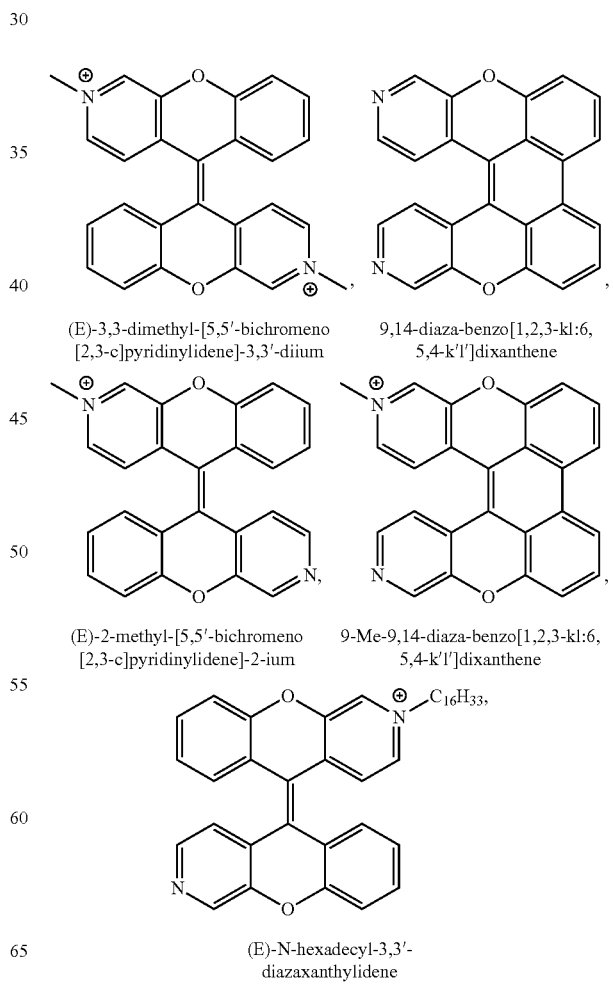

(E)-3,3-dimethyl-[5,5'-bichromeno[2,3-c]pyridinylidene]-3,3'-diium 9,14-diaza-benzo[1,2,3-kl:6,5,4-k'l']dixanthene (E)-2-methyl-[5,5'-bichromeno[2,3-c]pyridinylidene]-2-ium 9-Me-9,14-diaza-benzo[1,2,3-kl:6,5,4-k'l']dixanthene (E)-N-hexadecyl-3,3'-diazaxanthylidene -continued

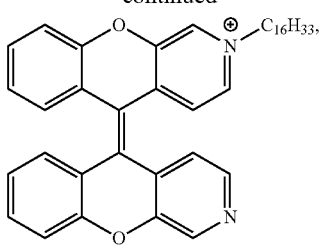

(Z)-N-hexadecyl-3,3'-
diazaxanthylidene

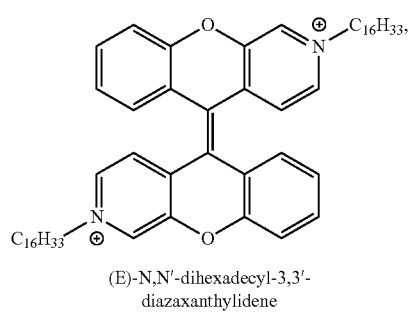

(E)-N,N'-dihexadecyl-3,3'-
diazaxanthylidene

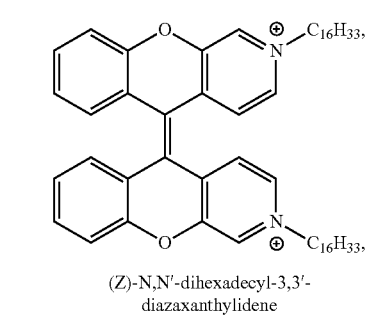

(Z)-N,N'-dihexadecyl-3,3'-
diazaxanthylidene

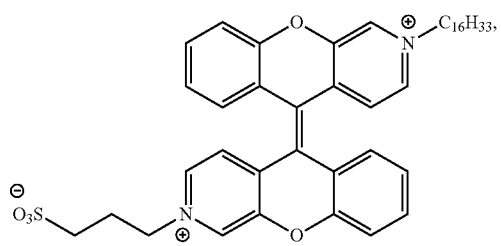

(E)-N-sulfopropyl-N'-hexadecyl-3,3'-diazaxanthylidene

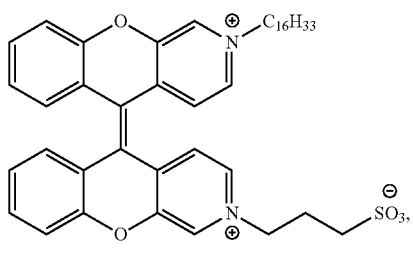

(Z)-N-sulfopropyl-N'-hexadecyl-3,3'-diazaxanthylidene

-continued

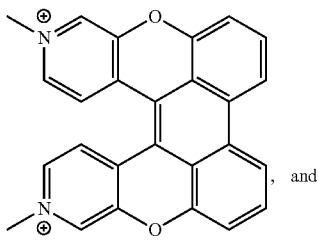, and 9,14-Dimethyl-9,14-diaza-benzo[1,2,3-kl:6,5,4-k'l']dixanthene

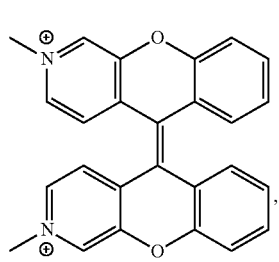, (Z)-N,-sulfopropyl-N'-hexadecyl-
3,3'-diazaxanthylidene mixtures thereof and salts thereof.

In one embodiment, the compound of formula (III) is selected from the group consisting of:

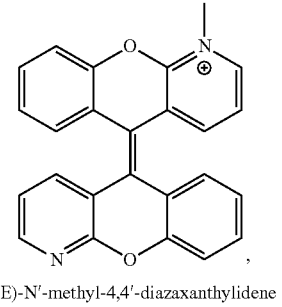, (E)-N'-methyl-4,4'-diazaxanthylidene

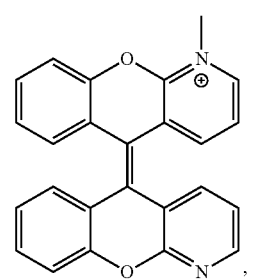, (Z)-N'-methyl-4,4'-diazaxanthylidene

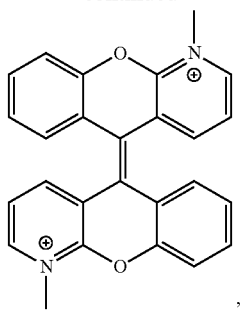

(E)-N,N'-dimethyl-4,4'-diazaxanthylidene

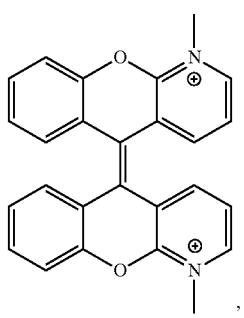

(Z)-N,N'-dimethyl-4,4'-diazaxanthylidene

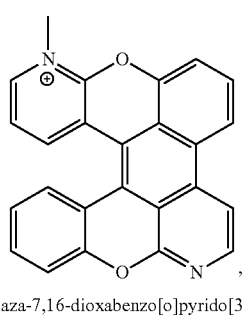

8-methyl-2-aza-7,16-dioxabenzo[o]pyrido[3,2-a]perylene

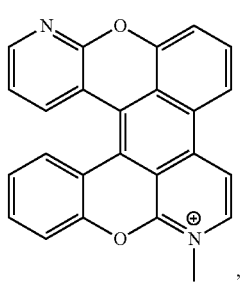

1-methyl-2-aza-7,16-dioxabenzo[o]pyrido[3,2-a]perylene mixtures thereof and salts thereof.

In one embodiment, the compound of formula (IV) is selected from the group consisting of:

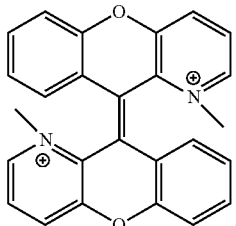

(E)-N,N'-dimethyl-1,1'-diazaxanthylidene

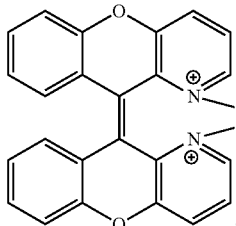

(Z)-N,N'-dimethyl-1,1'-diazaxanthylidene

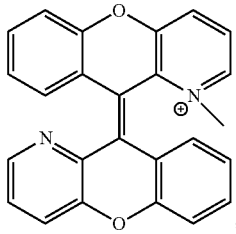

(E)-N-methyl-1,1'-diazaxanthylidene

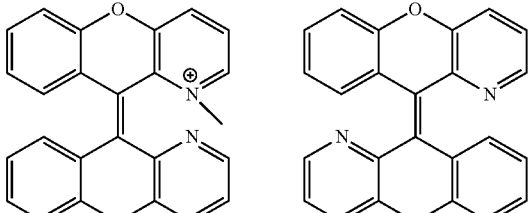

(Z)-N-methyl-1,1'-diazaxanthylidene        (E)-1,1'-diazaxanthylidene

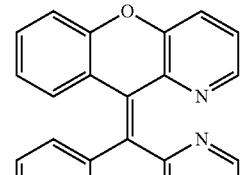

(Z)-1,1'-diazaxanthylidene

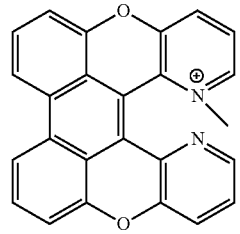

mixtures thereof and salts thereof.

Preparation of the Compounds of the Invention

Compounds of formula (I)-(IV) may be prepared by the general schemes described herein, using the synthetic method known by those skilled in the art. The following examples illustrate non-limiting embodiments of the invention.

In one aspect, compounds useful in the invention are synthesized using combinatorial chemistry methods to produce a large library of compounds. In a non-limiting embodiment, the synthesis of a library of 3,3-diazaxanthylidenes (3,3'-DAZAX) is accomplished by treating a mixture of biarylthiones with copper powder to form a statistical mixture of E- and Z- homo- and hetero- reductively coupled alkenes, followed by methylation of the mixture and subsequent irradiation of the mixture to induce photoelectrocyclization (FIG. 1). In one embodiment, the compounds are irradiated using a wavelength of about 365 nm. In another embodiment, the compounds are irradiated using visible light. In one embodiment, the water solubility of the compounds of the mixture is evaluated by performing an aqueous extraction on the resulting mixture, wherein compounds which are found in the aqueous layer are identified as being water soluble. In another embodiment, the irradiation step is performed prior to the methylation step. In one embodiment, the methylation reaction includes treatment with excess dimethylsulfate in chloroform, wherein the reaction is heated to a temperature of 55° C. In one embodiment, the coupling reaction takes place at an elevated temperature ranging from 80° C. to 250° C. Non-limiting examples of coupling methods include heating in toluene at reflux, and heating the mixture in a microwave.

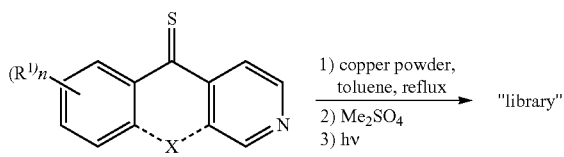

Figure 4:
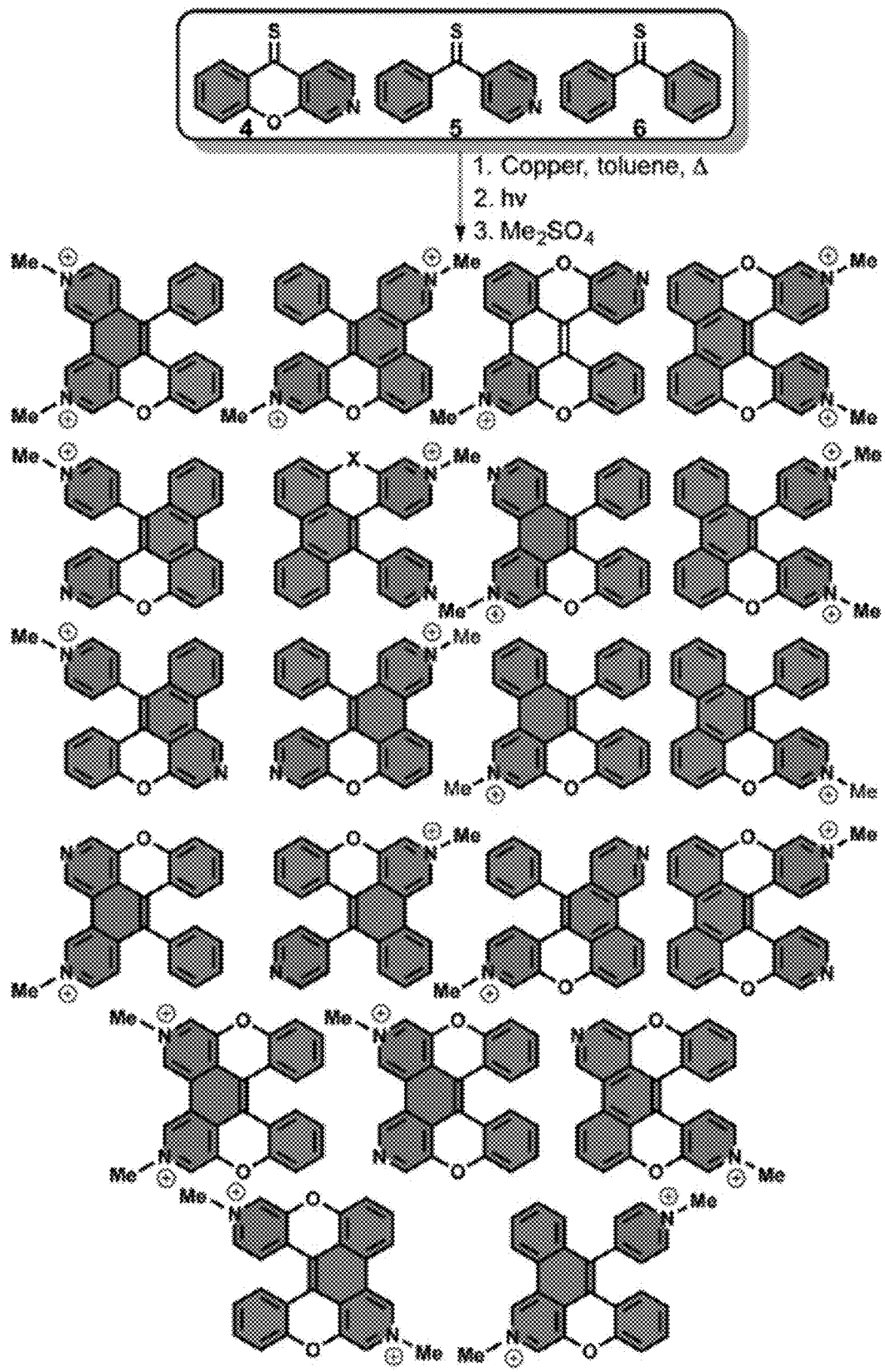
FIG. 4 is an illustration of the synthesis of an exemplary compound library beginning with 2-azaxanthione 4, phenylpyridinethione 5, and diphenylthione 6.

In another non-limiting embodiment, the synthesis of a library of compounds useful in the invention is accomplished by treating a mixture of 2-azaxanthione 4, phenylpyridinethione 5, and diphenylthione 6 with copper powder to form a statistical mixture of E- and Z- homo- and hetero- reductively coupled alkenes, followed by irradiation to induce photoelectrocyclization and subsequent methylation of the mixture (FIG. 4).

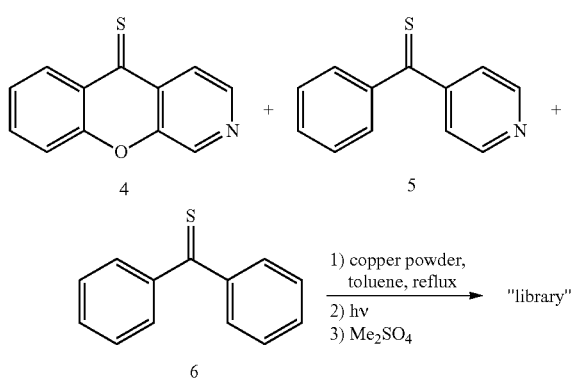

Figure 5:
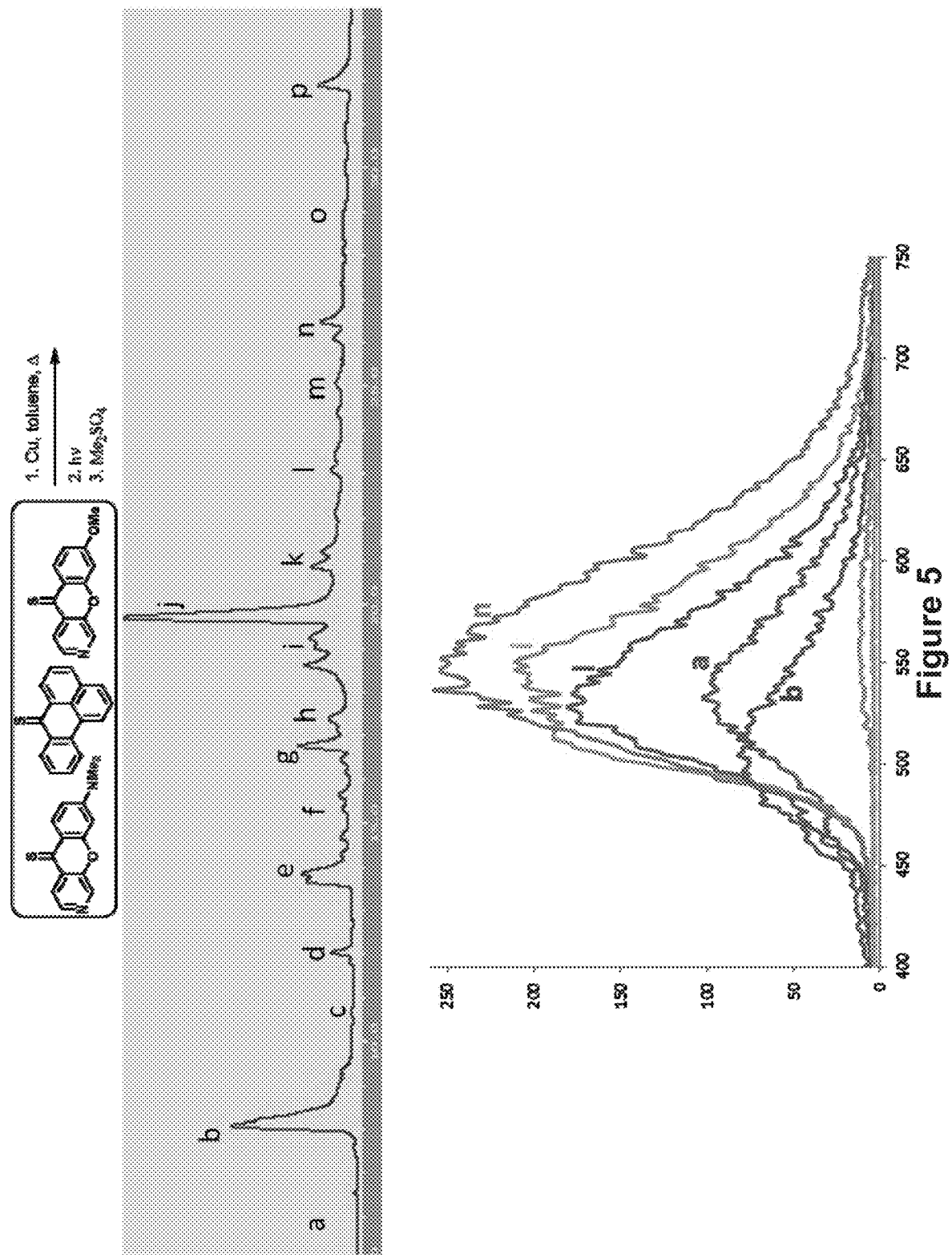
FIG. 5 is a HPLC trace of the products resulting from the reaction of 2-azaxanthione 4, phenylpyridinethione 5, and diphenylthione 6. The starting materials were refluxed in dry toluene for 48 h, photolyzed at 365 nm in a Rayonet for 24 h, then treated with excess dimethylsulfate in 55° C. chloroform.

In another non-limiting embodiment, the synthesis of a library of compounds useful in the invention is accomplished by treating a mixture of 2-azaxanthione 7, compound 8, and 2-azaxanthione 9 with copper powder to form a statistical mixture of E- and Z- homo- and hetero- reductively coupled alkenes, followed by irradiation to induce photoelectrocyclization and subsequent methylation of the mixture (FIG. 5).

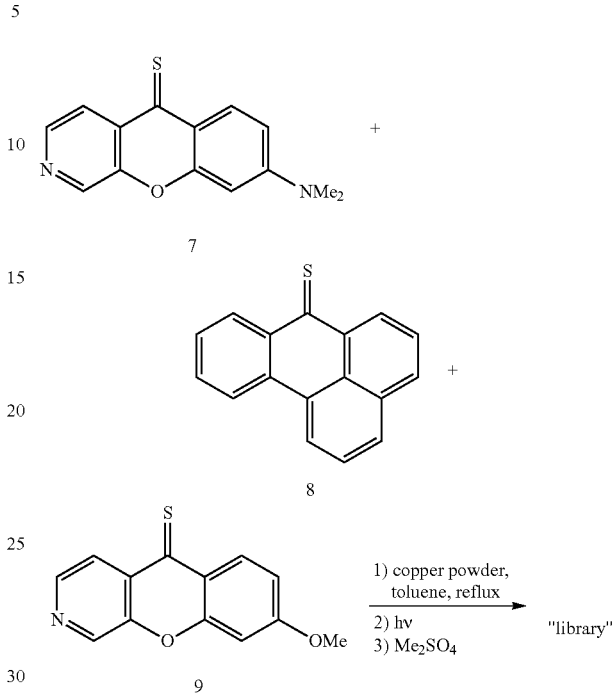

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water and ethanol. In another embodiment, the compounds described herein exist in unsolvated form.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

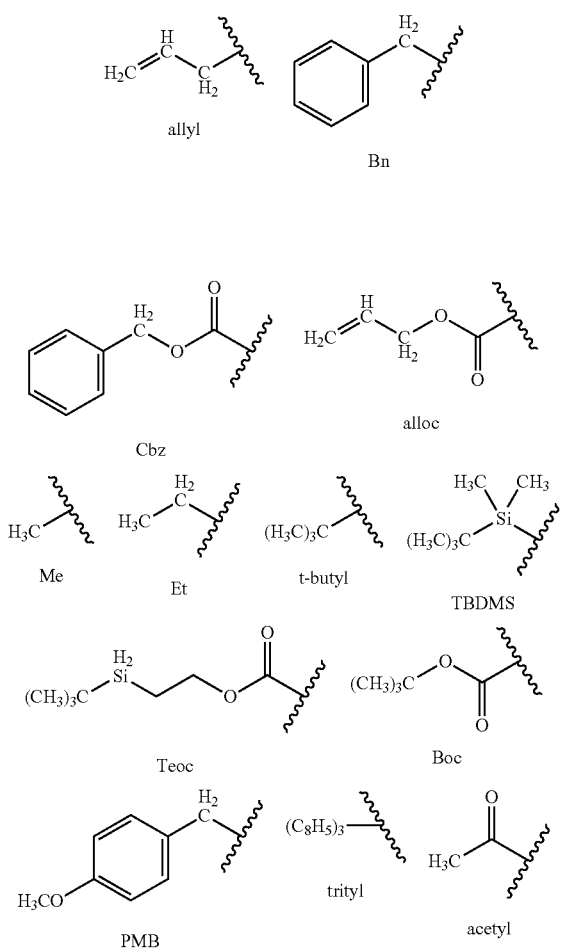

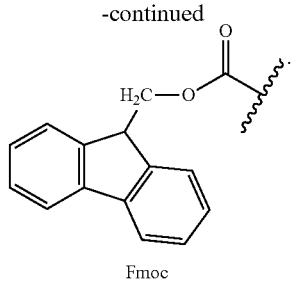

Fmoc

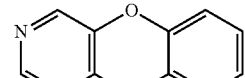

(E)-5,5'-bichromeno[2,3-c]pyridinylidene

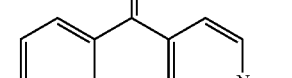

and

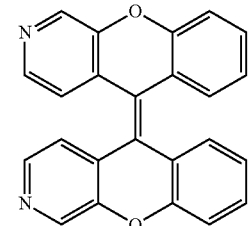

(Z)-5,5'-bichromeno[2,3-c]pyridinylidene,

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Screening

The present invention relates to the discovery of a new class of chromophore that lends itself to rapid synthesis, diversification, and evaluation through a modular synthetic approach. It is contemplated herein that a single compound may not be ideal as a universal imaging agent for a wide variety of bioimaging applications. Accordingly, the present invention includes a high-throughput method of identifying a compound useful as an imaging agent for a given application.

Any scaffold that can be modified to create a plurality of compounds is useful in the present invention, as would be understood by one skilled in the art. In one embodiment, the method comprises the steps of providing a DAZAX-based scaffold or derivative thereof; modifying the scaffold to create a plurality of compounds, i.e., synthesizing a library of compounds; and evaluating the compounds for bioimaging properties. In one embodiment, the DAZAX scaffold is a 3,3'-diazaxanthylidene (3,3'-DAZAX) scaffold. In another embodiment, the DAZAX scaffold is a 1,1'-diazaxanthylidene (1,1'-DAZAX) scaffold. In another embodiment, the DAZAX scaffold is a 2,2'-diazaxanthylidene (2,2'-DAZAX) scaffold. In another embodiment, the DAZAX scaffold is a 4,4'-diazaxanthylidene (4,4'-DAZAX) scaffold. In one embodiment, the method can further comprise the steps of identifying the most important properties for a bioimaging application, i.e., selection criteria, and selecting a compound for use as an imaging agent in the bioimaging application based on the evaluation of the candidate compound against the selection criteria.

As described herein, the DAZAX-based scaffold or derivatives thereof can be easily modified to create a library of compounds, as would be understood by one skilled in the art. Methods or techniques for modifying the scaffold can include, but are not limited to: E-/Z-interconversion, methylation, photocyclization, electrophillic aromatic substitution, subsequent crosscoupling and nucleophillic aromatic substitution. In one embodiment, the DAZAX-based scaffold is comprised of at least one compound selected from the group consisting of:

salts thereof, and mixtures thereof.

In one aspect, the present invention provides methods of modifying a DAZAX-based scaffold or derivatives thereof. In one embodiment, the method comprises the step of irradiating the scaffold. For example, irradiation of the scaffold induces photoelectrocyclization of the DAZAX compounds. In one embodiment, the scaffold is irradiated using a wavelength of about 375 nm to about 450 nm. In one embodiment, the scaffold is irradiated using a wavelength of about 365 nm. In another embodiment, the scaffold is irradiated using a wavelength of about 405 nm. The length of time of irradiation can generally be any length of time suitable for modification of the DAZAX-based scaffold. Examples of lengths of time include about 1 hour, about 2 hours, about 12 hours, about 24 hours, about 48 hours, and about 96 hours, and ranges between any two of these values. In one embodiment, the length of time of irradiation is about 24 hours. The method may also comprise a step of alkylating the scaffold. In one embodiment, the step of alkylating the scaffold occurs prior to the step of irradiating the scaffold. In an alternative embodiment, the step of alkylating the scaffold occurs after the step of irradiating the scaffold. In one embodiment, the step of alkylating the scaffold is methylation of the scaffold.

Once the compounds are generated, they can be evaluated for desired bioimaging properties, included, but not limited to: fluorescence, water solubility and cell permeability, non-toxicity, red-shifted excitation and emission maxima, stokes shift, resistance to photobleaching, compatibility with laser lines, brightness, size specific location, and photoswitching.

The desired bioimaging properties can vary based on the specific application. Accordingly, a compound with properties useful for a specific bioimaging application can be selected based on the bioimaging properties deemed most important for that specific application. For example, in one embodiment, a compound useful as an imaging agent in an application can be selected based primarily on the compound's fluorescence and resisting to photobleaching. However, the compound can be chosen based on any selection criteria, as would be understood by a person skilled in the art, and the evaluation and selection of a compound as an imaging agent is not limited to any specific property listed herein. In one embodiment, a compound displaying water solubility is selected. In another embodiment, a compound displaying emission from excitation at a specific wavelength is selected. In one embodiment, the wavelength is about 488 nm. In another embodiment, the wavelength is about 561 nm. In another embodiment, the wavelength is about 444 nm. The excitation energy can be applied to the compound using any method known in the art, such as hand-held ultraviolet lamps, fluorimeters, HPLC plate readers, mercury arc lamps, xenon lamps, lasers (such as argon and YAG lasers), and laser diodes. These illumination sources are typically optically integrated into laser scanners, fluorescence microplate readers or standard or microfluorimeters.

Upon selecting a compound as an imaging agent, the compound may be isolated from the compound library using any method known in the art, such as HPLC, 2 dimensional (2D) thin layer chromatography (TLC), preparatory TLC, crystallization, silica gel chromatography, and any other standard separation technology. In one embodiment, a compound is isolated from a compound library using HPLC. In another embodiment, a compound is isolated from a compound library using 2D TLC. Alternatively, a compound may be isolated prior to being selected as an imaging agent.

The compounds of the present invention may be useful for a variety of bioimaging applications, for example, but not limited to cell staining, fluorescence imaging, CT scanning, high content screening, metabolic profiling, enzyme inhibition, specific biomolecular targeting, flow cytometry, PCR-based technologies, fluorometric and colorimetric technologies, coating technologies, security technologies. The compounds of the present invention may also be incorporated into various matrices and composites for coating applications such as polymeric and resin-based coating applications. Accordingly, the selection criteria of the method of the present invention can vary based on the specific needs of a given bioimaging application.

In one aspect, the present invention provides a method for imaging a sample. The method comprises providing a sample, contacting the sample with a compound of the present invention, irradiating the sample with an excitation wavelength range, and detecting fluorescence of the sample, thereby imaging the sample. In one embodiment, at least a portion of the sample exhibits increased fluorescence after the contacting step compared to before the contacting step. In one embodiment, the sample is a cell. In another embodiment, the cell is a live cell. In one embodiment, the sample may be excited and the emission may be monitored at the compound's neutral or acidic wavelength range, allowing for the mapping of acidic versus neutral of basic cellular environments.

In one aspect, the compounds of the invention are useful in methods to detect the presence or absence of an organelle in a sample. In one embodiment, the organelle is a lysosome. In another embodiment, the organelle is a nucleus. In another embodiment, the organelle is mitochondria. In a non-limiting example, a compound of the present invention localizes to the mitochondria in a cell, while excluding the nucleus, allowing imaging of the mitochondria. The method can comprise providing a sample suspected of containing the organelle, contacting the sample with at least one compound of the invention to prepare a test sample, and illuminating the test sample with energy. The method can further comprise detecting emission of energy from the test sample after the illuminating step. In one embodiment, the illuminating step comprises irradiating the sample with an excitation wavelength range. The detecting step can be qualitative or quantitative. In some embodiments, the compound of the present invention can be used in combination with other imaging compounds, such as common dyes or fluorescent proteins.

The presence of an emitted fluorescent energy (or an increase in emitted fluorescent energy relative to a control) is indicative of the presence of the organelle, while the absence of emitted fluorescent energy (or no increase or no change relative to a control) is indicative of the absence of the organelle in the sample.

In some embodiments, irradiating the test sample results in intracellular photoactivation of the compound. In one embodiment, the entire test sample is irradiated. In another embodiment, a portion of the test sample is irradiated. For example, when a portion of the test sample is irradiated, only compounds that are present in the area of the test sample that is irradiated will undergo photoactivation, and will emit fluorescent energy. Accordingly, compounds that are not present in the area of the test sample that is illuminated would remain inert and would not emit fluorescent energy. This method allows for the selective photoactivation of a specific area of the sample. In a non-limiting example, a sample comprised of multiple cells where the cells are confluent can be administered a compound of the invention, and a single cell from within the sample can be selectively photoactivated, and therefore can be easily identified from among neighboring cells. In another non-limiting example, a specific area of a sample comprised of a single cell can be selectively photoactivated, permitting the imaging of a specific organelle. As would be understood by one skilled in the art, any method of photoactivating a compound may be used, such as a laser.

The sample can generally be any type of sample. For example, the sample can be a cell or group of cells, an organism, cell lysates, a cell culture medium, a bioreactor sample, and so on. In one embodiment, the sample is a cell. In one embodiment, the cell is a HeLa cell. In one embodiment, the cells are live cells. Alternatively, the sample can be a non-biological sample. The cells can be any type of cell, such as bacterial cells, fungal cells, insect cells, and mammalian cells. The sample can be a solid, a liquid, or a suspension. The sample can be a biological fluid such as blood, plasma, or urine. The sample can be a material immobilized in a gel, on a membrane, bound to a bead or beads, arranged in an array, and so on. The sample can be a partially or fully purified preparation in a buffer or in water.

The contacting step can be performed at any suitable temperature, and for any suitable length of time. Typically, the temperature will be ambient or room temperature, or at an elevated temperature such as 37° C. Examples of temperatures include about 20° C., about 25° C., about 30° C., about 35° C., about 37° C., about 40° C., about 42° C., and ranges between any two of these values. Temperatures higher than about 42° C., and temperatures lower than about 20° C. are also possible, depending on the sample tested. The length of time can generally be any length of time suitable for detection of a change in fluorescence. Examples of lengths of time include about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 180 minutes, about 240 minutes, about 300 minutes, about 360 minutes, about 420 minutes, about 480 minutes, about 540 minutes, about 600 minutes, and ranges between any two of these values. Further extended lengths of time are also possible, depending on the sample tested.

The compound or compounds can be used at generally any concentration suitable to produce a detectable emitted fluorescent energy signal in the presence of an organelle. Example concentration ranges include about 10 nM to about 10 mM. Examples of concentrations include about 10 nM, about 100 nM, about 1 µM, about 2 µM, about 3 µM, about 4 µM, about 5 µM, about 6 µM, about 7 µM, about 8 µM, about 9 µM, about 10 µM, about 100 µM, about 1 mM, about 10 mM, and ranges between any two of these values. In one embodiment, the concentration is 2 mM.

The excitation energy can be applied to the test sample in a variety of ways during the illuminating step. Suitable equipment includes hand-held ultraviolet lamps, mercury arc lamps, xenon lamps, lasers (such as argon and YAG lasers), and laser diodes. These illumination sources are typically optically integrated into laser scanners, fluorescence microplate readers or standard or microfluorometers.

In one embodiment, the excitation wavelength range is between about 375 nm to about 450 nm. In one embodiment, the excitation wavelength is about 365 nm. In another embodiment, the excitation wavelength is about about 405 nm.

The detecting step can be performed by visual inspection, or by the use of a variety of instruments. Examples of such instruments include CCD cameras, video cameras, photographic film, laser scanning devices, fluorometers, photodiodes, quantum counters, epifluorescence microscopes, scanning microscopes, flow cytometers, fluorescence microplate readers, or by amplification devices such as photomultiplier tubes.

The detecting step can be performed at a single point in time, can be performed at multiple points in time, or can be performed continuously.

The methods can be used in conjunction with experimental systems such as flow cytometry, fluorescence microscopy, and so on.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

A High Throughput Approach to Rapidly Discovering New Imaging Agents

Figure 2:
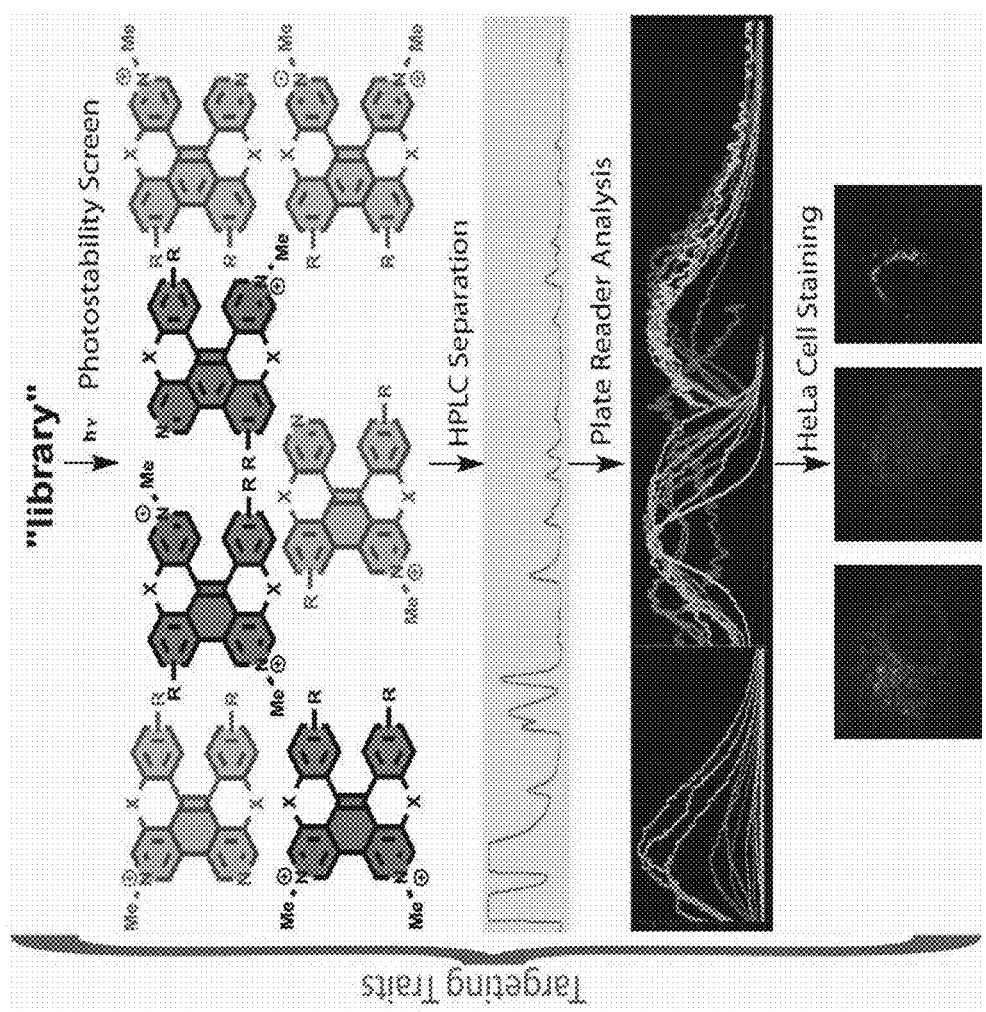
FIG. 2 is an illustration of the identification of photostable compounds from the generated library. The compounds can be isolated via HPLC separation, and their cell staining properties evaluated in HeLa cells.

Described herein is the discovery of a new class of chromophore that lends itself to rapid synthesis, diversification, and evaluation through a modular synthetic approach and subsequent high throughput evaluation process, using either high tech (HPLC & plate reader) or low tech (2D TLC & fluorimeter) methods. Libraries of novel diazaxanthylidene (DAZAX)-derived chromophores were conveniently 1) synthesized in a modular fashion from arylpyridylthiones (FIG. 1), 2) diversified via E-/Z-interconversion, pyridinium formation, and photo-6π-electrocyclizations (FIG. 1), and 3) evaluated for desired properties via HPLC (or TLC), plate reader (or fluorimeter), and microscopy (FIG. 2). This approach provides rapid means of discovering water-soluble, photo-bleach-resistant, red-shifted-emitting chromophores with convenient excitation bands at 488 and 561 nm. A library derived from only three thiones has generated eight such dyes, three of which display some specificity for lysosomal, mitochondrial, and nuclear staining. This approach demonstrates how to quickly adjust a DAZAX scaffold to obtain optimal imaging agents.

Table 1 below identifies compounds of the present invention which are discussed in Example 1 and throughout the specification.

TABLE 1

Compounds of the present invention

| Structure | Name | Compound Name |
|---|---|---|
| 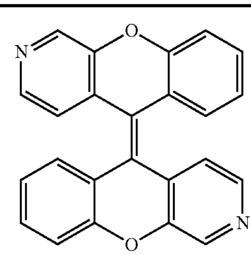 | (E)-5,5'-bichromeno[2,3-c]pyridinylidene | E-1 |

TABLE 1-continued

Compounds of the present invention

| Structure | Name | Compound Name |
|---|---|---|
| 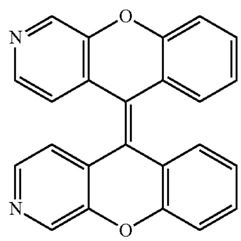 [SMILES: c1ccc2c(c1)Oc1cnccc1/C2=C1/c2ccccc2Oc2cnccc21] | (Z)-5,5'-bichromeno[2,3-c]pyridinylidene, | Z-1 |
| 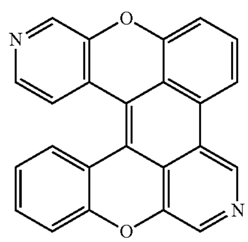 [SMILES: c1ccc2c(c1)oc1cncc3c4cccc5oc6cnccc6c(c54)c2c13] | chromeno[2,3,4-de]pyrido[3',4':2,3]chromeno[4,5-gh]isoquinoline;2,9-diaza-benzo[1,2,3-kl:6,5,4-k'l']dixanthene | 2 |
| 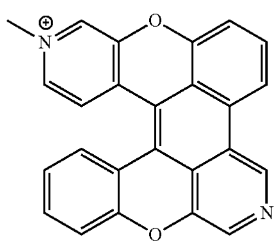 [SMILES: C[n+]1ccc2c(c1)oc1cccc3c4cncc5oc6ccccc6c(c54)c2c13] | 9-methylchromeno[2,3,4-de]pyrido[3',4':2,3]chromeno[4,5-gh]isoquinolin-9-ium | Me-2 |
| 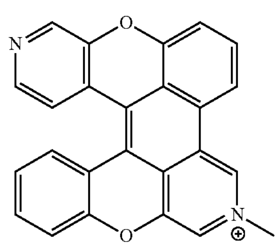 [SMILES: C[n+]1cc2oc3ccccc3c3c2c(c1)c1cccc2oc4cnccc4c3c21] | 2-methylchromeno[2,3,4-de]pyrido[3',4':2,3]chromeno[4,5-gh]isoquinolin-2-ium | Me-2 |
| 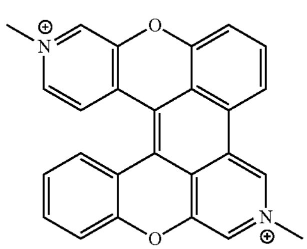 | 2,9-dimethylchromeno[2,3,4-de]pyrido[3',4':2,3]chromeno[4,5-gh]isoquinoline-2,9-diium | DiMe-2 |
| 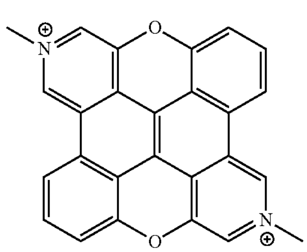 | 2,9-dimethyl-7,14-dioxa-2,9-diazaphenanthro[1,10,9,8-opqra]perylene-2,9-diium | 10 |

TABLE 1-continued

Compounds of the present invention

| Structure | Name | Compound Name |
|---|---|---|
| 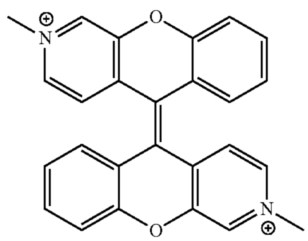 | (E)-3,3'-dimethyl-[5,5'-bichromeno[2,3-c]pyridinylidene]-3,3'-diium | DiMe-E-1 |
| 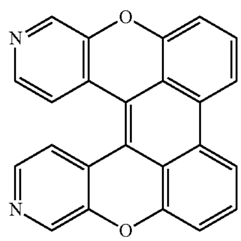 [SMILES: c1cc2oc3cnccc3c3c2c(c1)c1cccc2oc4cnccc4c3c21] | 9,14-diaza-benzo[1,2,3-kl:6,5,4-k'l']dixanthene | 3 |
| 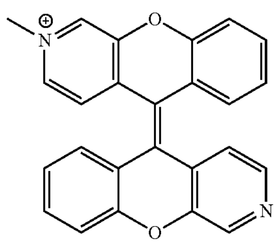 [SMILES: C[n+]1ccc2c(c1)Oc1ccccc1/C2=C1/c2ccccc2Oc2cnccc21] | (E)-2-methyl-[5,5'-bichromeno[2,3-c]pyridinylidene]-2-ium | Me-E-1 |
| 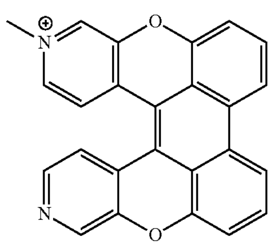 [SMILES: C[n+]1ccc2c(c1)oc1cccc3c4cccc5oc6cnccc6c(c54)c2c13] | 9-Me-9,14-diaza-benzo[1,2,3-kl:6,5,4-k'l']dixanthene | Me-E-3 |
| 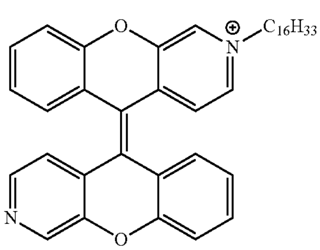 | (E)-N-hexadecyl-3,3'-diazaxanthylidene | |
| 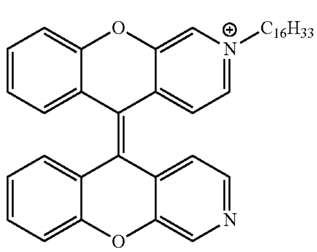 | (Z)-N-hexadecyl-3,3'-diazaxanthylidene | |

TABLE 1-continued

Compounds of the present invention

| Structure | Name | Compound Name |
|---|---|---|
| 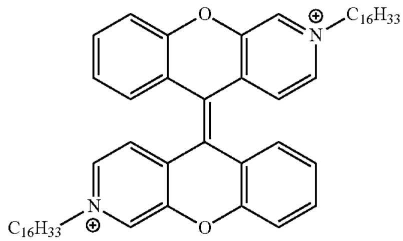 | (E)-N,N'-dihexadecyl-3,3'-diazaxanthylidene | |
| 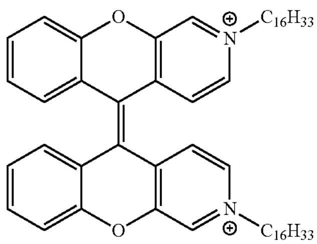 | (Z)-N,N'-dihexadecyl-3,3'-diazaxanthylidene | |
| 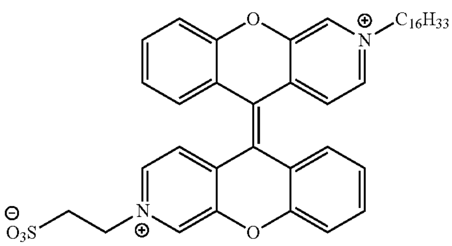 | (E)-N-sulfopropyl-N'-hexadecyl-3,3'-diazaxanthylidene | |
| 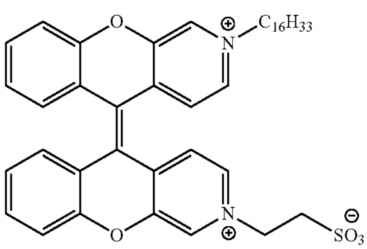 | (Z)-N-sulfopropyl-N'-hexadecyl-3,3'-diazaxanthylidene | |
| 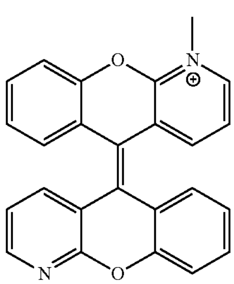 [SMILES: C[n+]1cccc2c1Oc1ccccc1/C2=C1/c2ccccc2Oc2ncccc21] | (E)-N'-methyl-4,4'-diazaxanthylidene | |
| 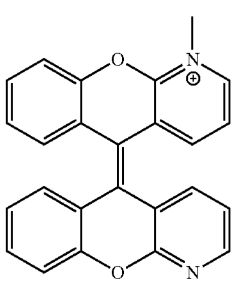 [SMILES: C[n+]1cccc2c1Oc1ccccc1/C2=C1\c2ccccc2Oc2ncccc21] | (Z)-N'-methyl-4,4'-diazaxanthylidene | |

TABLE 1-continued

| Compounds of the present invention | | |
|---|---|---|
| Structure | Name | Compound Name |
| | (E)-N,N'-dimethyl-4,4'-diazaxanthylidene | |
| | (Z)-N,N'-dimethyl-4,4'-diazaxanthylidene | |
| | 8-methyl-2-aza-7,16-dioxabenzo[o]pyrido[3,2-a]perylene | |
| | 1-methyl-2-aza-7,16-dioxabenzo[o]pyrido[3,2-a]perylene | |
| | (E)-N,N'-dimethyl-1,1'-diazaxanthylidene | |

TABLE 1-continued

| Compounds of the present invention | | |
|---|---|---|
| Structure | Name | Compound Name |
| | (Z)-N,N'-dimethyl-1,1' diazaxanthylidene | |
| | (E)-N-methyl-1,1'-diazaxanthylidene | 11-E |
| | (Z)-N-methyl-1,1'-diazaxanthylidene | 11-Z |
| | 9,14-dimethyl-9,14-diaza-benzo[1,2,3-kl:6,5,4-k'l']dixanthene | DiMe-3 |
| | (Z)-N, N'-dimethyl-3,3'-diazaxanthylidene | DiMe-Z-1 |
| | (E)-1,1'-diazaxanthylidene | 10-E |

TABLE 1-continued

Compounds of the present invention

| Structure | Name | Compound Name |
|---|---|---|
| 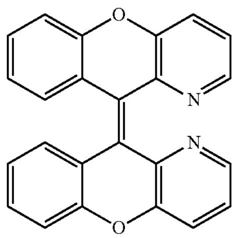 [SMILES: c1ccc2c(c1)Oc1cccnc1/C2=C1/c2ccccc2Oc2cccnc21] | (Z)-1,1'-diazaxanthylidene | 10-Z |
| | | 12 |

The opportunity for a high throughput approach to generate new imaging agents was recognized upon discovering four significant properties of 3,3'-diazaxanthylidene (3,3'-DAZAX) 1. First, the alkene interconverts between E- and Z-isomers at room temperature (Rarig et al., 2013, J. Am. Chem. Soc. 135: 9213-9219, which is incorporated by reference in its entirety for all purposes). Second, the E-/Z-mixture is emissive in solution, powdered, and crystalline states. Third, both the E- and Z-isomer undergo intramolecular oxidative couplings under photolytic conditions to cause a red shift in excitation and emission maxima. Finally, the mono- and bis-methylation of the two aza functionalities provides both water solubility and red shifts in the scaffold's excitation and emission maxima. The E-/Z-interconversion, mono- vs. bis-methylation of the diaza scaffold, and intramolecular photochemical ring closure provide easy diversification of a scaffold that can be formed by reductively coupling arylpyridylthiones. The red-shifting and water-solubilizing effects are advantageous and crucial, respectively.

The investigation of the nucleic acid-binding ability of diazaxanthylidene 1, which is synthesized by reductive dimerization of 2-azaxanthione 4, led to the observation of diazaxanthylidene 1's E-/Z-interconversion at rt, as well as the red-shifting and water solubilizing effects of methylating one of its pyridine moieties (Rarig et al., 2013, J. Am. Chem. Soc. 135: 9213-9219, which is incorporated by reference in its entirety for all purposes). The discovery that E-/Z-diazaxanthylidene 1 undergoes Mallory reactions to generate red-shifted species was a result of reusing a TLC plate. Exposure to a UV hand lamp converted diazaxanthylidene 1 from blue-emissive to green-emissive. Upon eluting the green spot up the silica plate in 2:1 EtOAc:CHCl$_3$, it separated into three spots: a blue-emissive spot (unreacted diazaxanthylidene 1) and two yellow/orange-emissive spots, one above and one below diazaxanthylidene 1 on the TLC plate. Irradiating a THF solution of diazaxanthylidene 1, propylene oxide, and iodine with 365 nm light for 26 h provided crystals for x-ray analysis that confirmed the top photoproduct, 3,3'-DAXAZ-T (2) was the result of Z-diazaxanthylidene 1 undergoing a single Mallory reaction. Comparing the crystal structures of diazaxanthylidene 1 and compound 2, it is clear that the red shift caused by photolytic oxidative coupling is the result of increased planarity within the scaffold, allowing for greater electron delocalization (FIG. 1). $^1$H NMR spectroscopy confirmed that the bottom photoproduct, 3,3'-DAZAX-B (3) was the product of the two phenyl moieties of Z-1 undergoing oxidative coupling. No evidence was found for the two pyridyl moieties undergoing oxidative coupling (Mallory et al., 1964, J. Am. Chem. Soc. 86: 3094).

Figure 3:
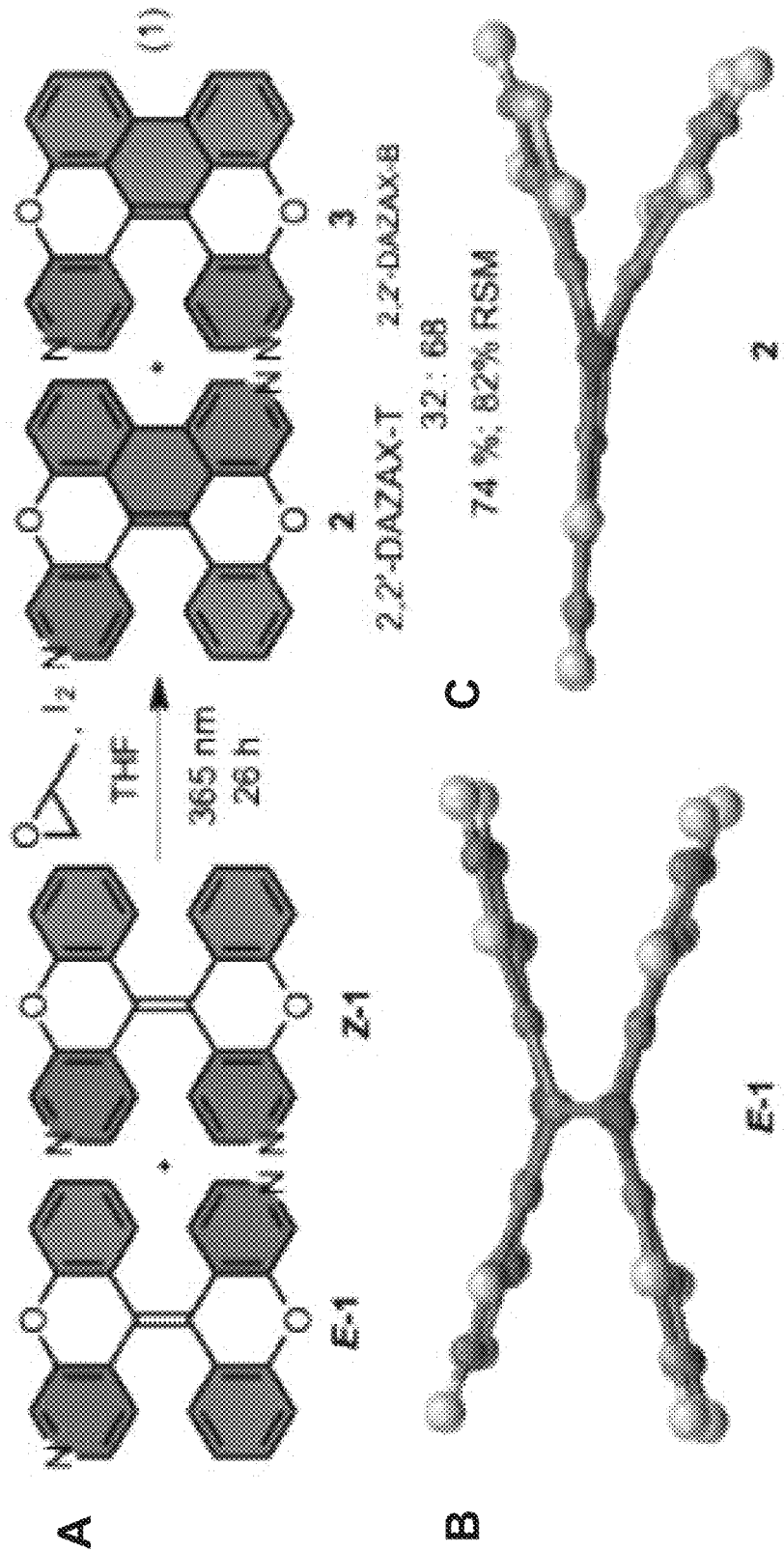
FIG. 3, comprising

The DAZAX-derived scaffolds of compounds 2 and 3 (FIG. 3) represent an original class of emissive polycyclic aromatic scaffold with an impressive variety of possible derivatizations that warrant immediate investigation: 1) changing and/or removing the oxygen tether between aryl rings, 2) limiting the scaffold to a single pyridine moiety, 3) replacing 2-azaxanthione with the 1,3, and 4-azaxanthone analogs, 4) varying pi systems by replacing the phenyl moiety with an acenyl or heteroaryl rings, 5) electronic perturbation via functionalization with different electron withdrawing and/or donating groups, and 6) alkylating the pyridine with a species besides methyl. It was recognized that a small-scale high throughput approach with an emphasis on finding desired bioimaging properties would be much more efficient than repeatedly attempting to optimize any of the nine listed properties by hypothesizing which perturbation(s) to investigate with a single scaffold's synthesis one at a time.

A three-step, one-pot library synthesis was envisioned involving 1) a mixture of biarylthiones forming a statistical mixture of E- and Z- homo- and hetero- reductively coupled alkenes upon refluxing in anhydrous toluene with copper powder, 2) then irradiating (365 nm) the resulting DAZAX-like scaffolds for 24 h to induce photo-electrocyclization, and 3) subsequent methylation of the resulting mixture. Water solubility would then be evaluated first by simply doing an aqueous extraction. The resulting aqueous mixture could then be assayed by HPLC before and after extended irradiation in order to do a qualitative assessment of photostability. Finally, any species showing emission from excitation at 488 nm on a plate reader would be concentrated, taken up in media, and incubated with HeLa cells to evaluate cell permeability and localization specificity by confocal microscopy.

Figure 6:
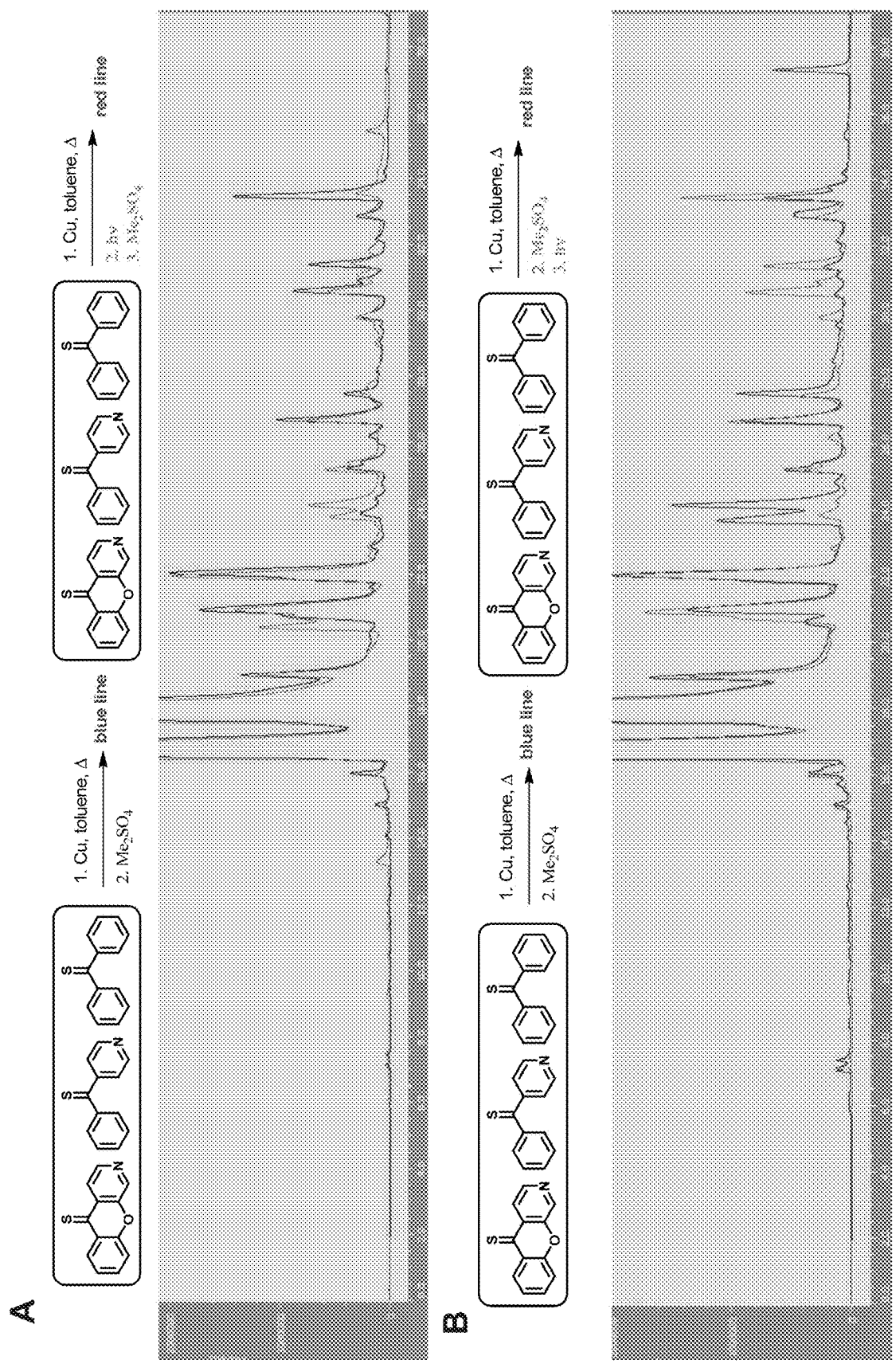
FIG. 6, comprising
Figure 7:
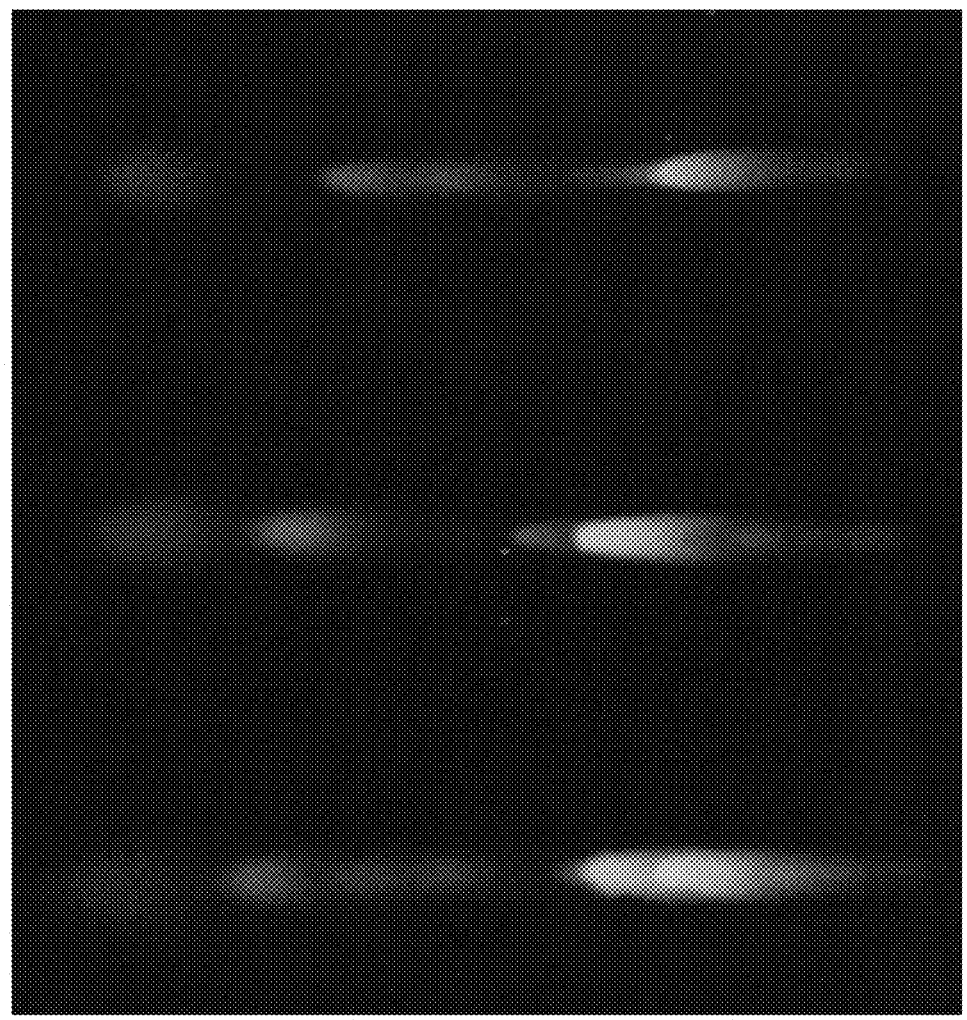
FIG. 7 is a photograph of a TLC plate screened for emission, using an excitation wavelength of 488 nm. Lane 1 illustrates the emission using a protocol of photolysis followed by methylation. Lane 2 illustrates the emission using a protocol of methylation only. Lane 3 illustrates the emission using a protocol of methylation followed by photolysis.

The thione precursors used for an exemplary compound library was 2-azaxanthione 4, phenylpyridinethione 5, and diphenylthione 6 (FIG. 4). These precursors allowed initial investigation into the significance of diaza vs. monoaza scaffolds, E- vs. Z-effects, and oxygen-tethered biaryl thiones vs. untethered biaryl thiones. The thione mixture was refluxed in dry toluene for 48 h, photolyzed at 365 nm in a Rayonet for 24 h, then treated with excess dimethylsulfate in 55° C. chloroform (FIG. 5). The resulting mixture was extracted into water, irradiated for another 24 hours, concentrated and chromatographed using reverse-phase HPLC or TLC (FIG. 6A). A similar chromatograph was generated using a methylation-then-photolysis protocol (FIG. 6B). It was hypothesized that the methylated mixture underwent more efficient ring-closing under visible light conditions than the non-methylated mixture did under either UV or visible light conditions. Although not wishing to be bound by any particular theory, this result suggests that the less photostable of these scaffolds could serve as useful photoswitches in vivo. A Tecan plate reader was used to screen for emission, using an excitation wavelength of 488 nm (FIG. 7).

Figure 8:
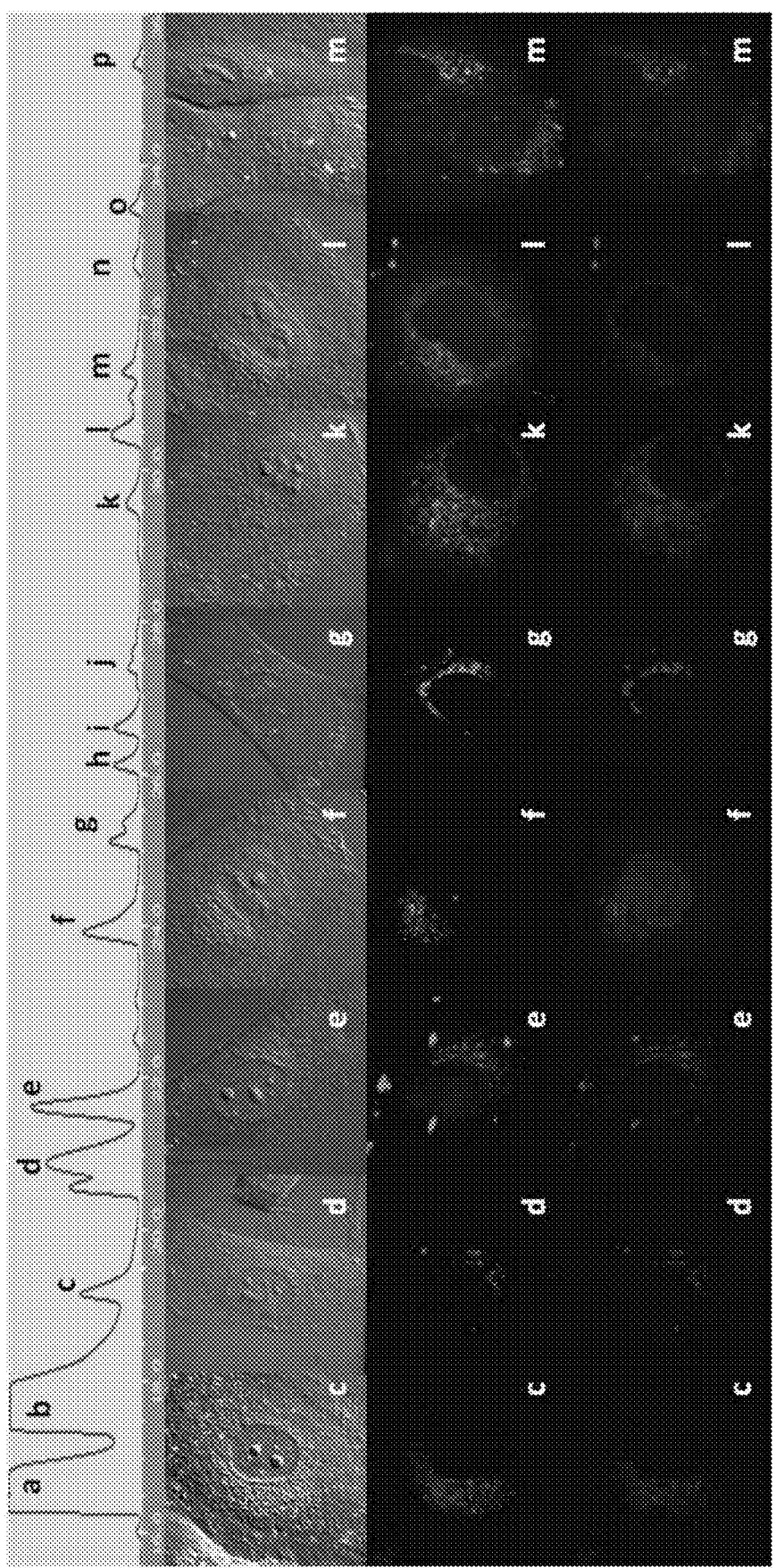
FIG. 8 is an image of confocal microscopy identifying cells stained using isolated compounds of the present invention. Stained cells were imaged by exciting with a 488 nm laser while observing at 503-545 nm (the green overlay images), exciting with a 561 nm laser while observing at 583-650 nm (the red overlay images), and by DIC (the grey images).
Figure 9:
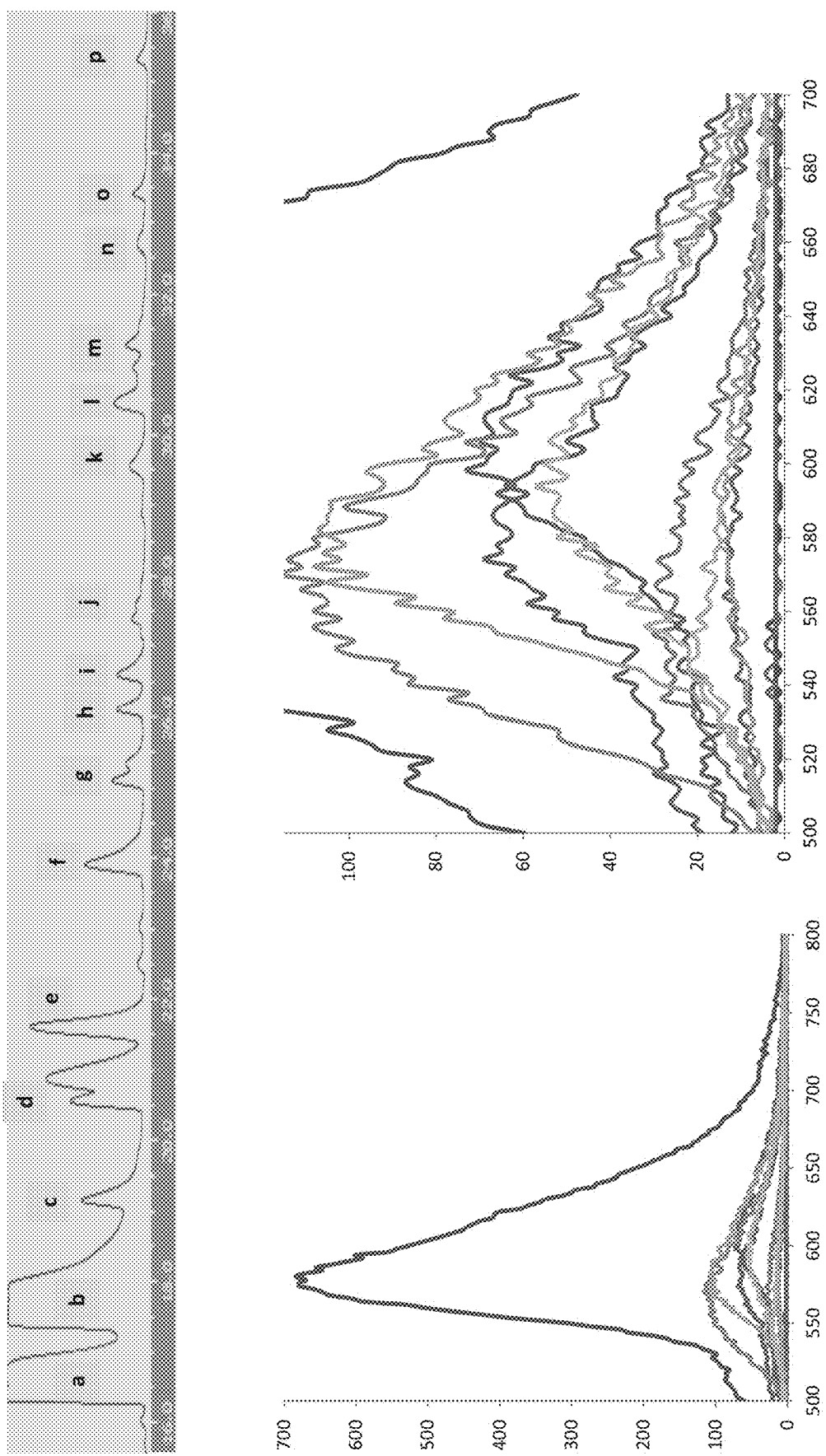
FIG. 9 depicts the plate reader emission spectra for compounds prepared using the methods of the invention upon excitation using a wavelength of 488 nm.
Figure 10:
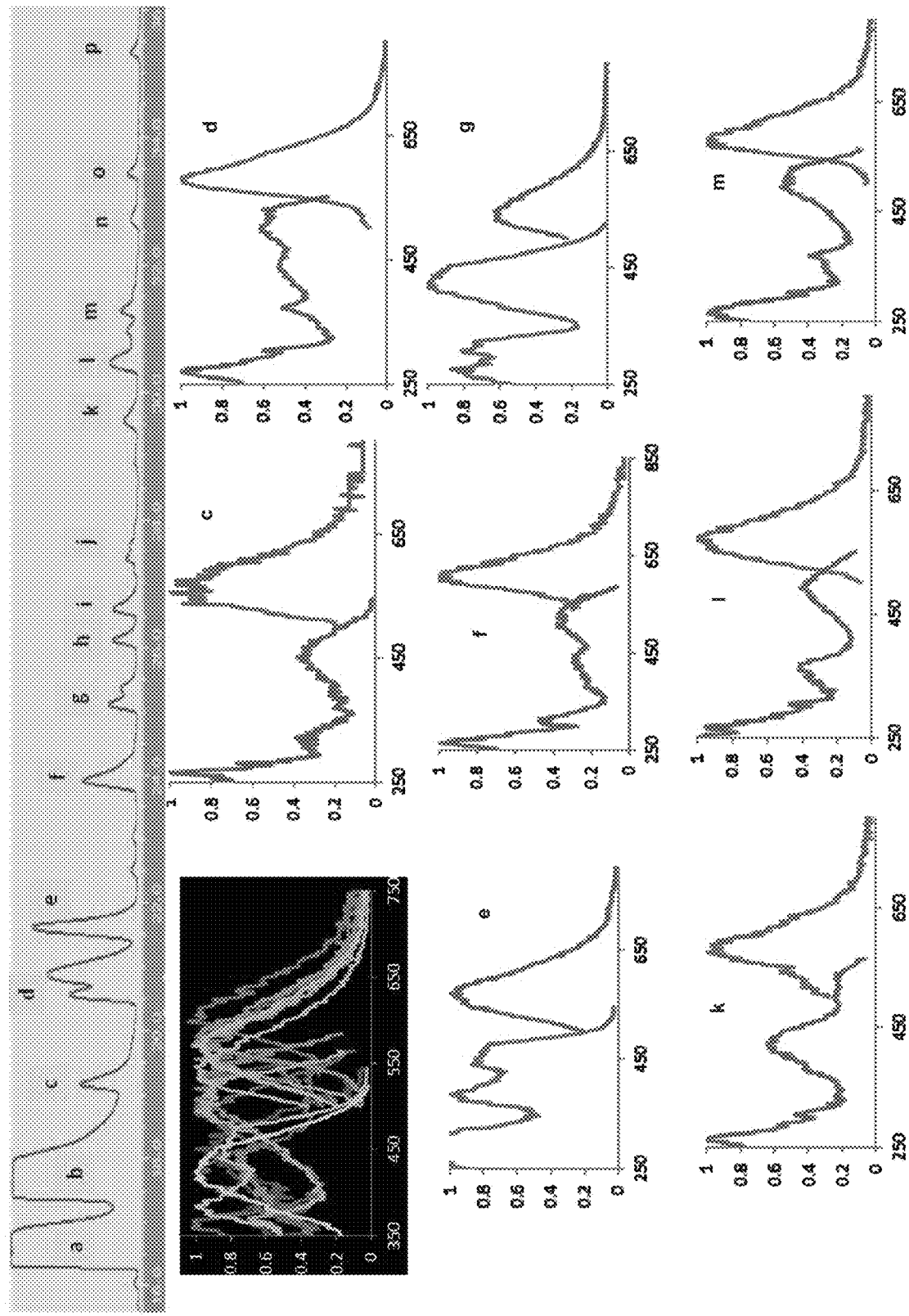
FIG. 10 depicts the excitation/emission spectra for compounds prepared using the methods of the invention upon excitation using a wavelength of 488 nm.
Figure 11:
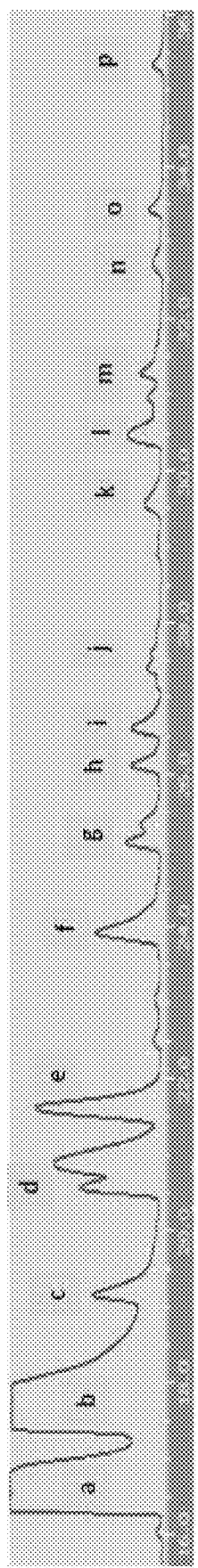
FIG. 11 depicts the excitation/emission spectra for compound c. Green coloring indicates an excitation wavelength of 488 nm, collected from 503-545 nm. Red: coloring indicates an excitation wavelength of 560 nm, observed at 583-650 nm.
Figure 11:
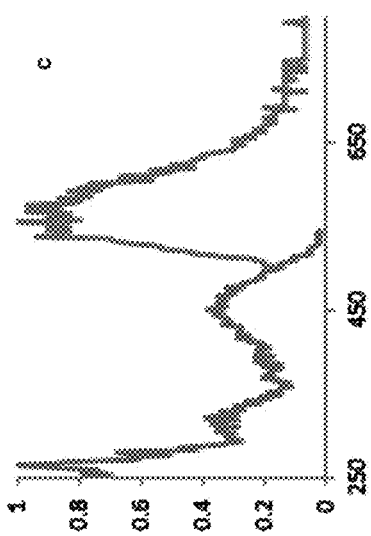
Figure 11:
Figure 11:
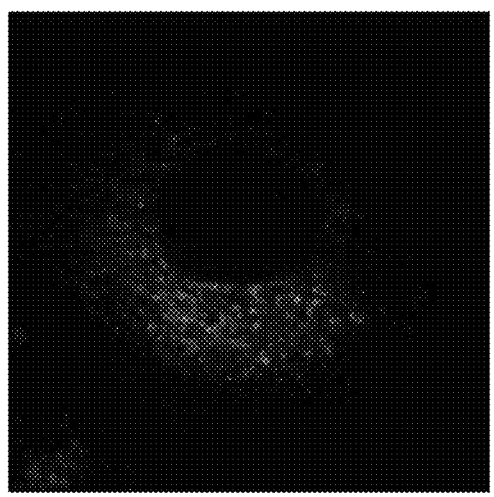
Figure 11:
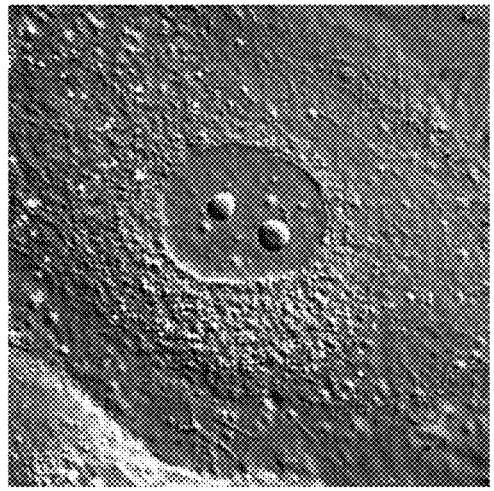
Figure 12:
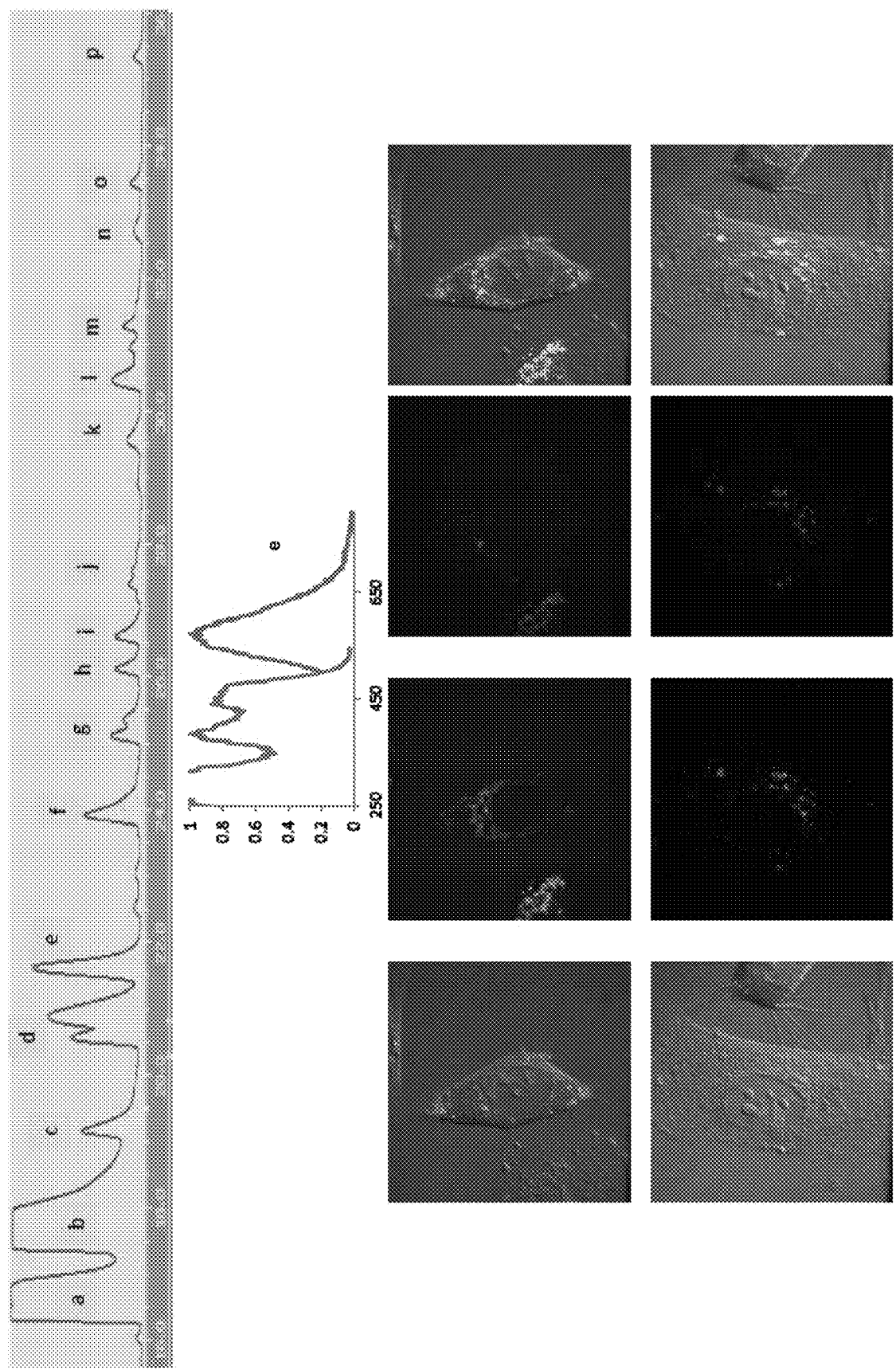
FIG. 12 depicts the excitation/emission spectra for compound e. Green coloring indicates an excitation wavelength of 488 nm, collected from 503-545 nm. Red: coloring indicates an excitation wavelength of 560 nm, observed at 583-650 nm.
Figure 13:
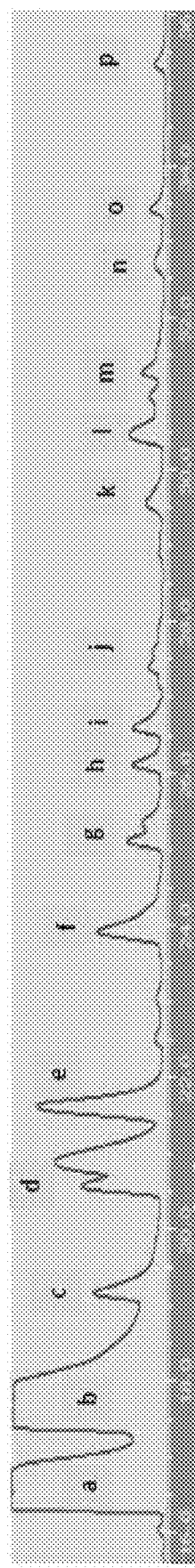
FIG. 13 depicts the excitation/emission spectra for compound g. Green coloring indicates an excitation wavelength of 488 nm, collected from 503-545 nm. Red: coloring indicates an excitation wavelength of 560 nm, observed at 583-650 nm.
Figure 13:
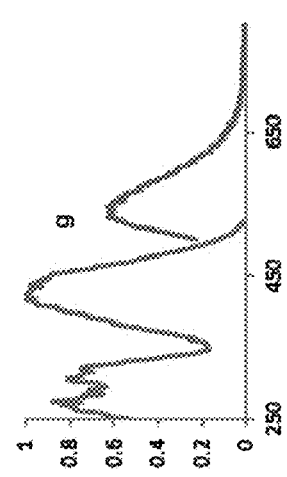
Figure 13:
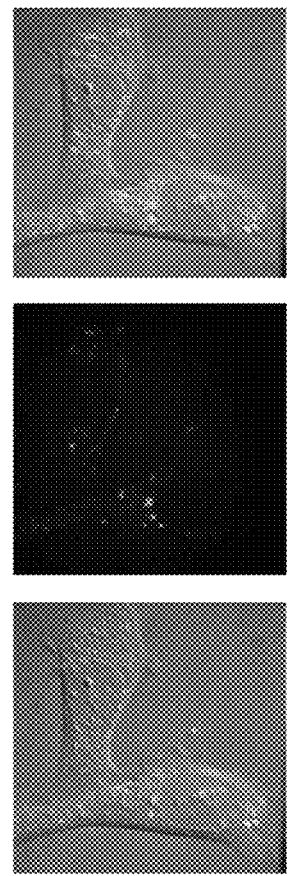
Figure 13:
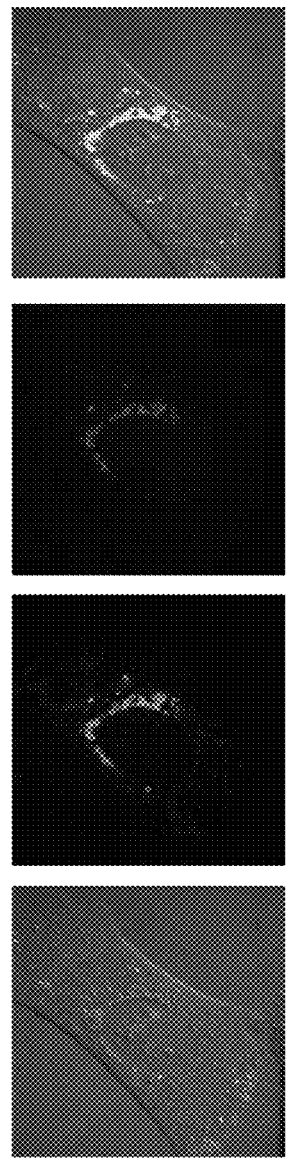
Figure 14:
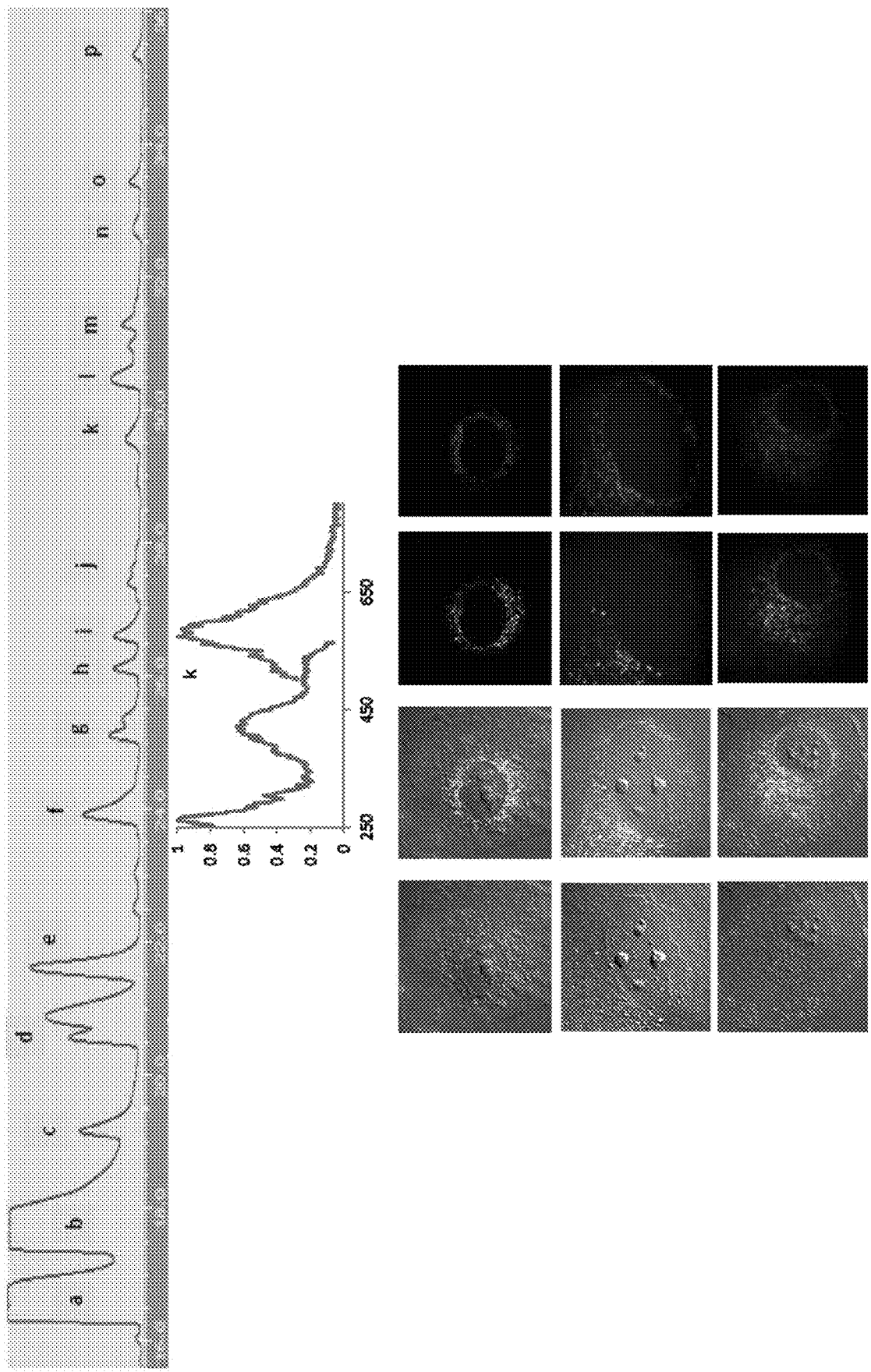
FIG. 14 depicts the excitation/emission spectra for compound k. Green coloring indicates an excitation wavelength of 488 nm, collected from 503-545 nm. Red: coloring indicates an excitation wavelength of 560 nm, observed at 583-650 nm.
Figure 15:
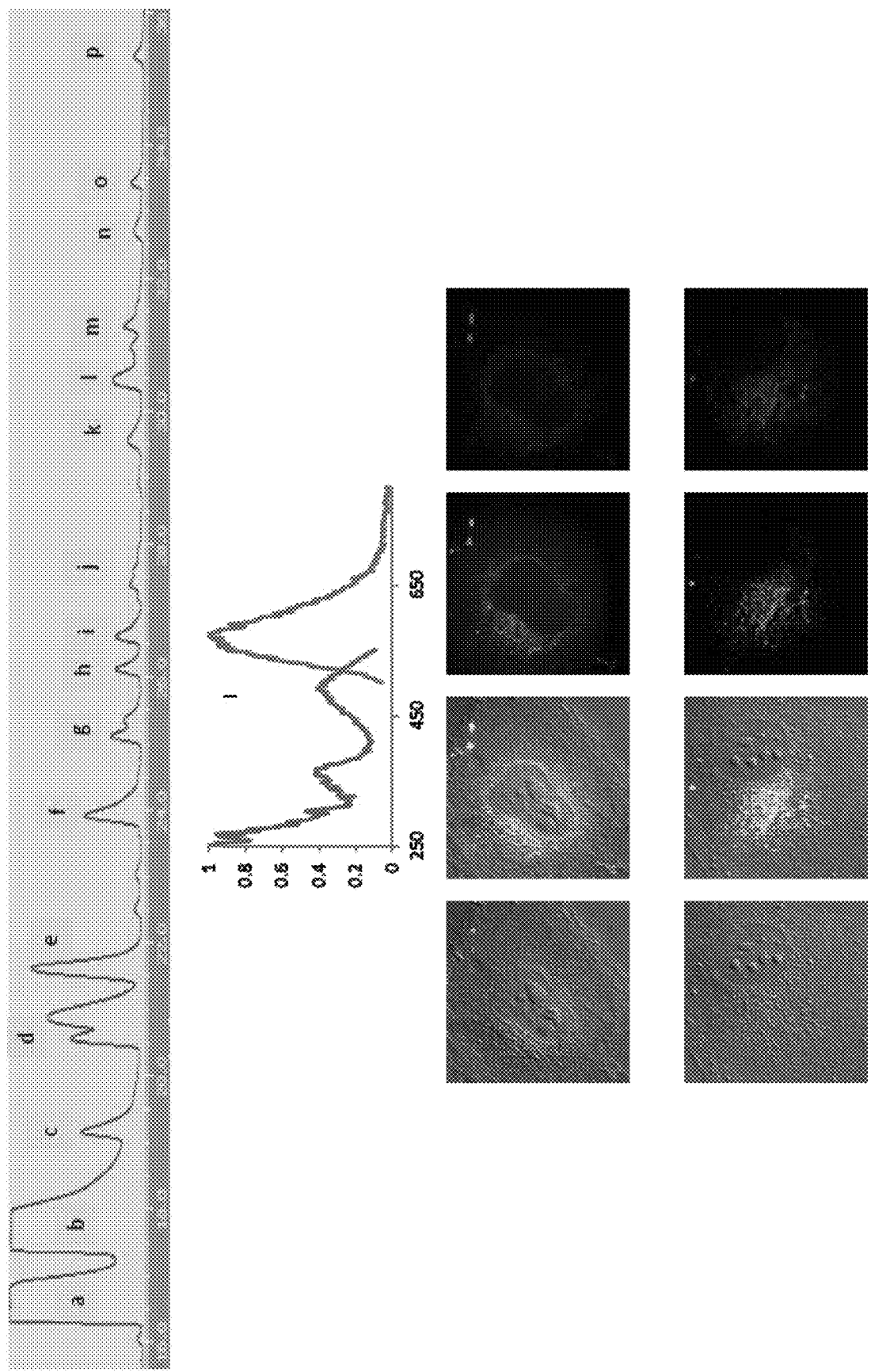
FIG. 15 depicts the excitation/emission spectra for compound l. Green coloring indicates an excitation wavelength of 488 nm, collected from 503-545 nm. Red: coloring indicates an excitation wavelength of 560 nm, observed at 583-650 nm.
Figure 16:
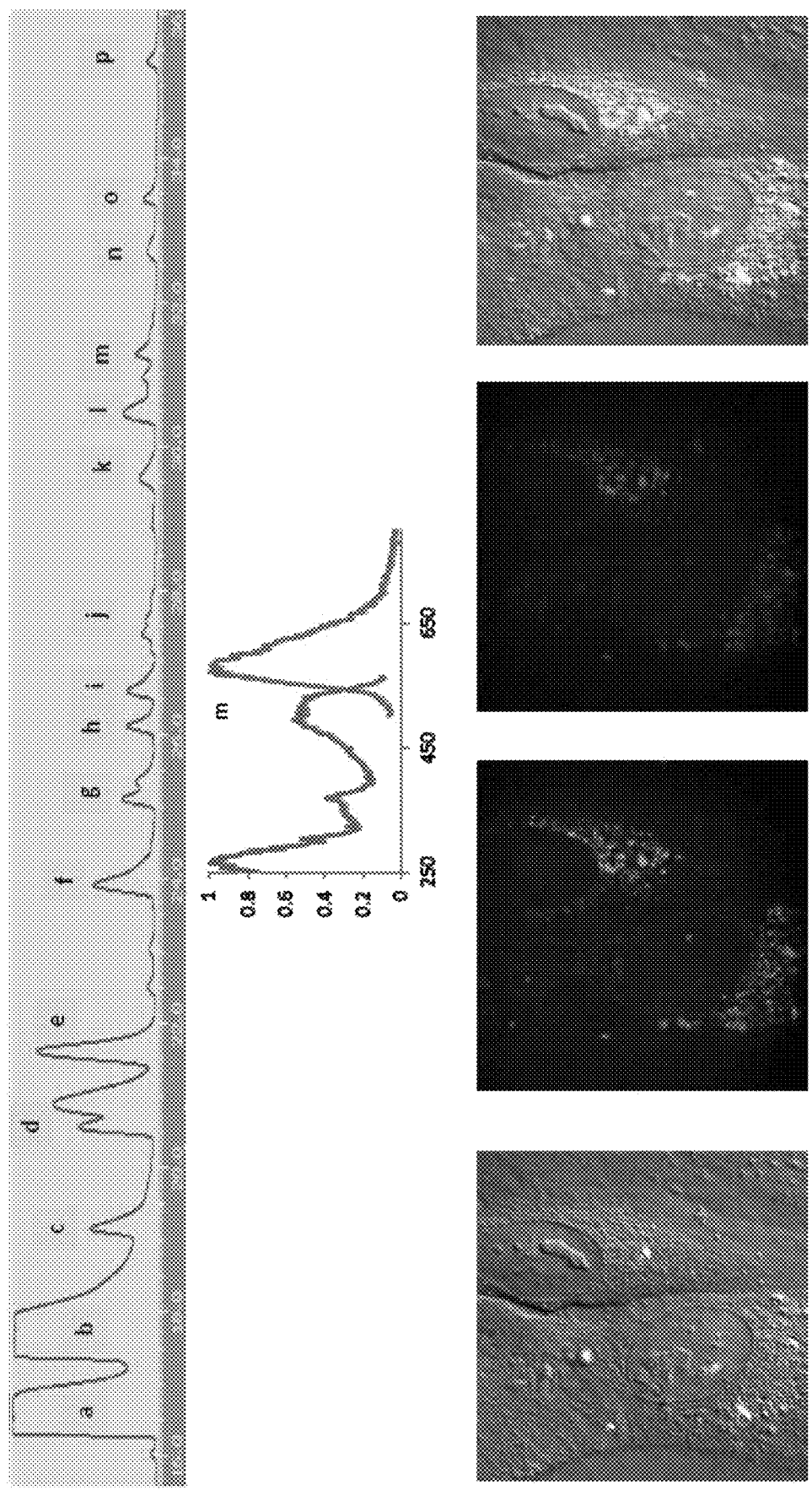
FIG. 16 depicts the excitation/emission spectra for compound m. Green coloring indicates an excitation wavelength of 488 nm, collected from 503-545 nm. Red: coloring indicates an excitation wavelength of 560 nm, observed at 583-650 nm.

The compounds that displayed promising excitation/emission properties were concentrated, introduced to HeLa cells in 2 mL solutions in DMEM media, and incubated for 12 h at 37° C./5% $CO_2$. Confocal microscopy was done on a Yokogawa spinning disk inverted microscope with a 100× lens. Each batch of stained cells was imaged by exciting with a 488 nm laser while observing at 503-545 nm (the green overlay images), exciting with a 561 nm laser while observing at 583-650 nm (the red overlay images), and by DIC (the grey images) (FIG. 8). Every compound that was of interest after the plate reader assay was cell permeable. A variety of specific staining abilities were discovered among the very first library; a total of eight water-soluble, cell-permeable, 488 nm-excitable dyes were discovered. As depicted in FIG. 8, compounds f and m provided both nuclear and extranuclear punctuate staining, compounds c, d, e, and g provided punctuate staining, and compounds k and l both provided what appeared to be Mitochondrial staining. The results of the plate reader screen for the library can be seen in FIGS. 9-16.

Figure 17:
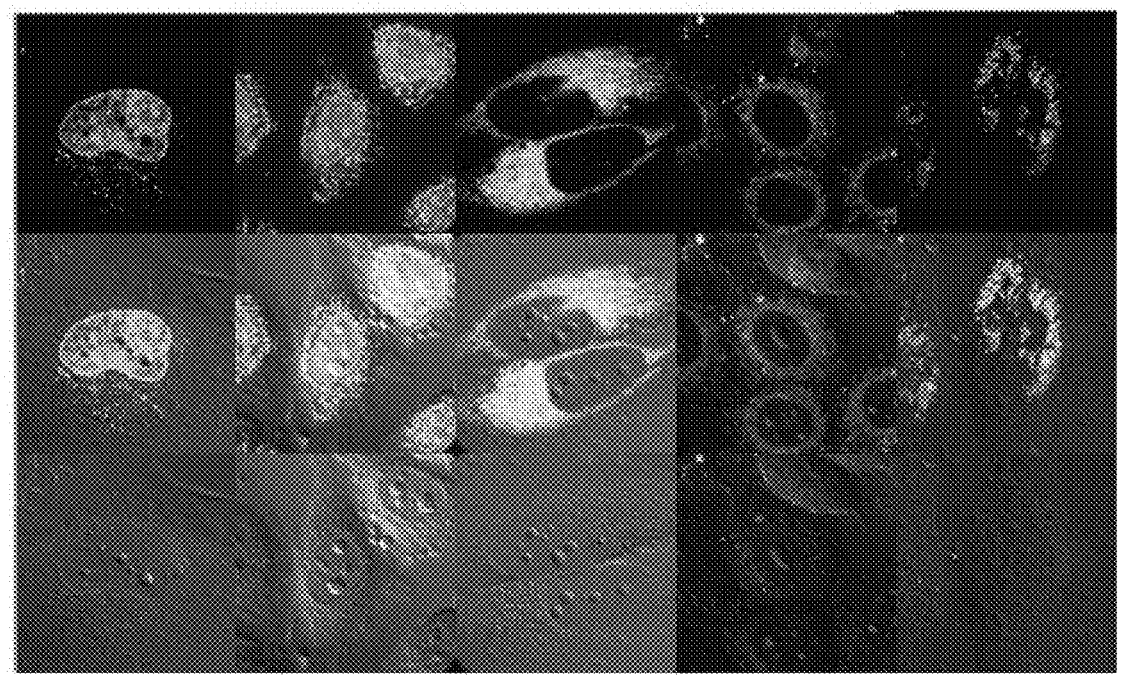
FIG. 17 depicts the nuclear staining of compounds Me-3, Me-2, 2, and Me-E-1 in HeLa cells.
Figure 17:
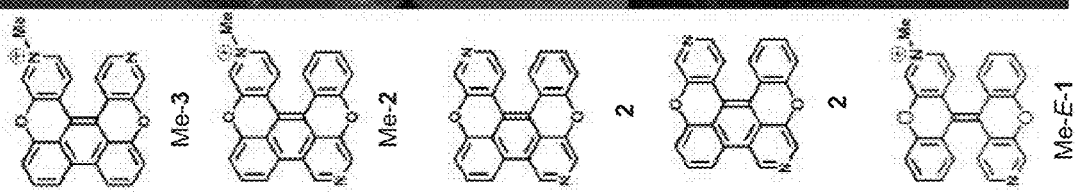
Figure 18:
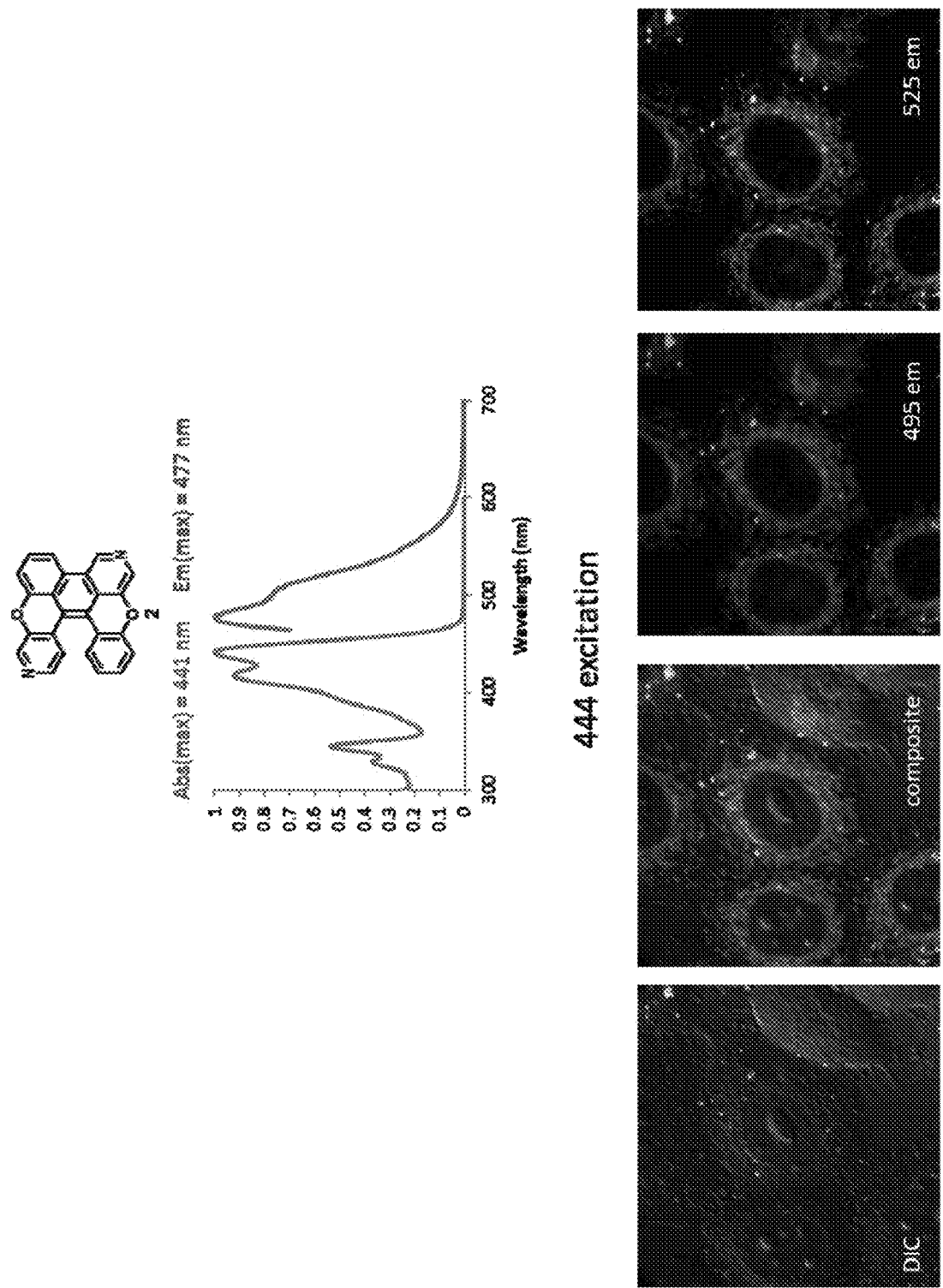
FIG. 18 is a series of images of cells stained with compound 2. Cells were irradiated using an excitation wavelength of 444 nm.
Figure 19:
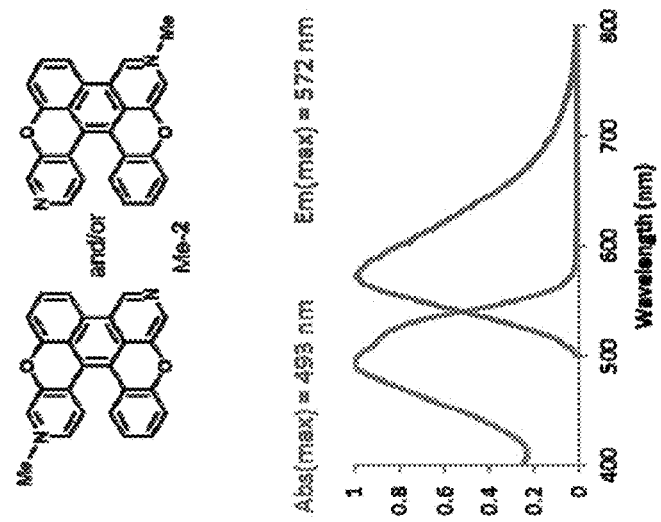
FIG. 19 is a series of images of cells stained with compound Me-2.
Figure 20:
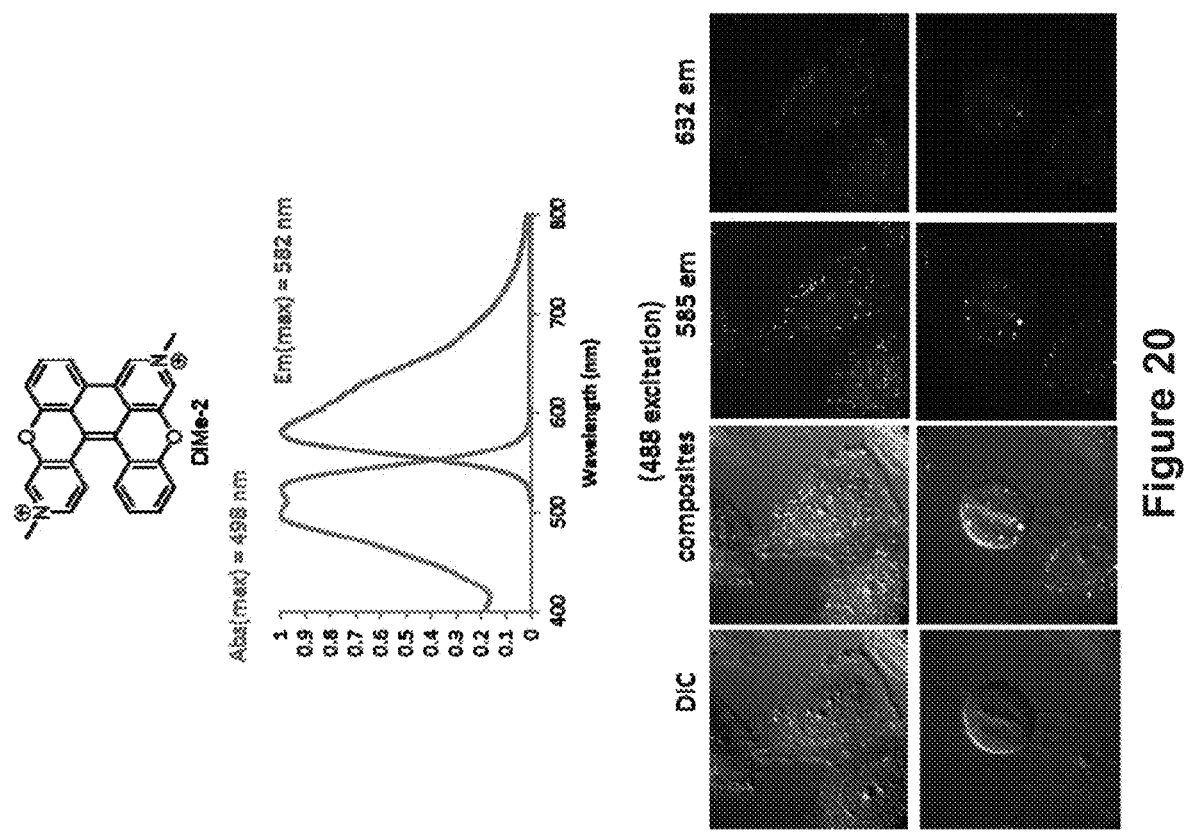
FIG. 20 is a series of images of cells stained with compound DiMe-2. Cells were irradiated using an excitation wavelength of 488 nm.
Figure 21:
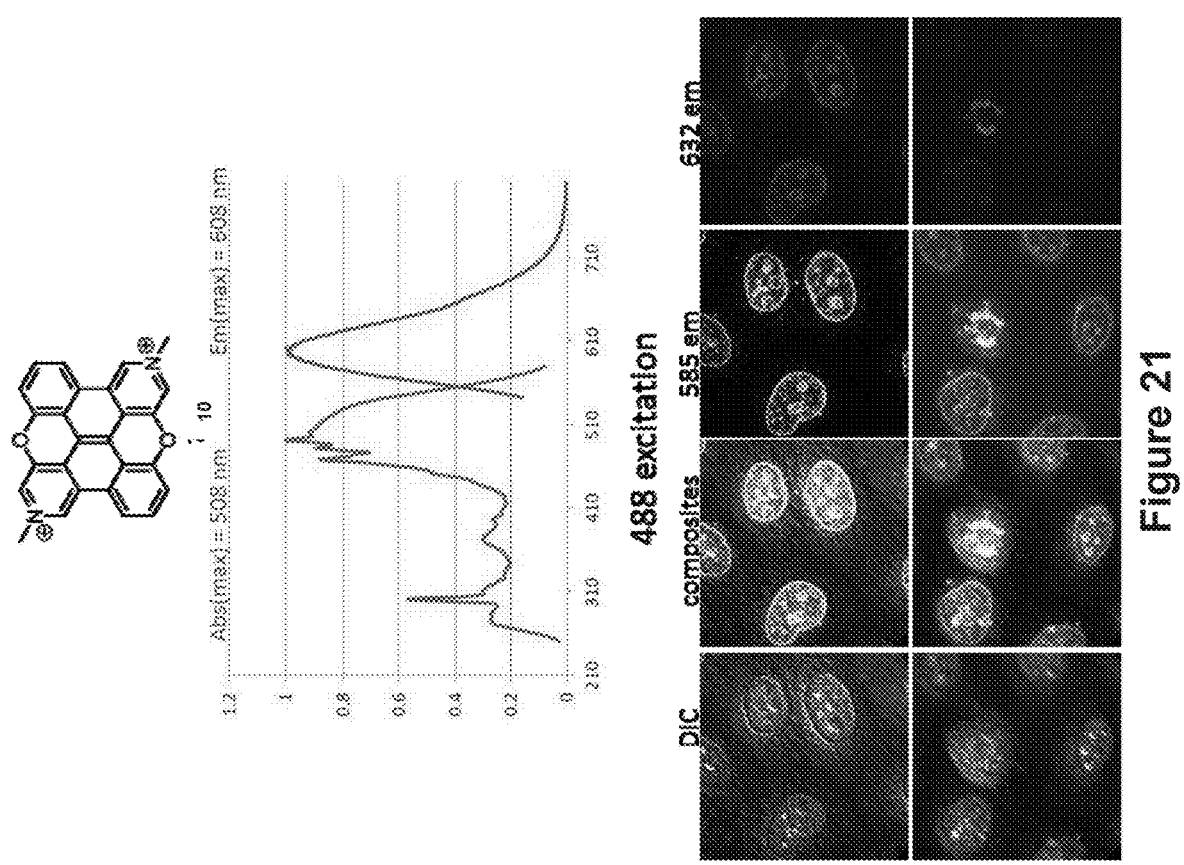
FIG. 21 is a series of images of cells stained with compound 10. Cells were irradiated using an excitation wavelength of 488 nm.
Figure 22:
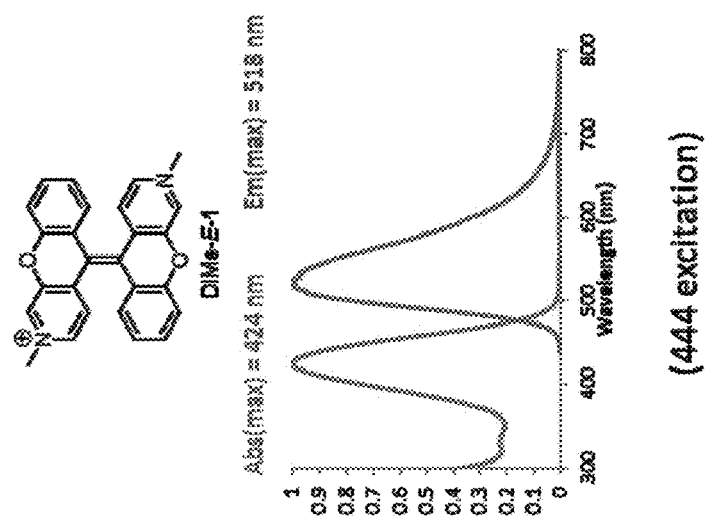
FIG. 22 is a series of images of cells stained with compound DiMe-E-1. Cells were irradiated using an excitation wavelength of 444 nm.
Figure 22:
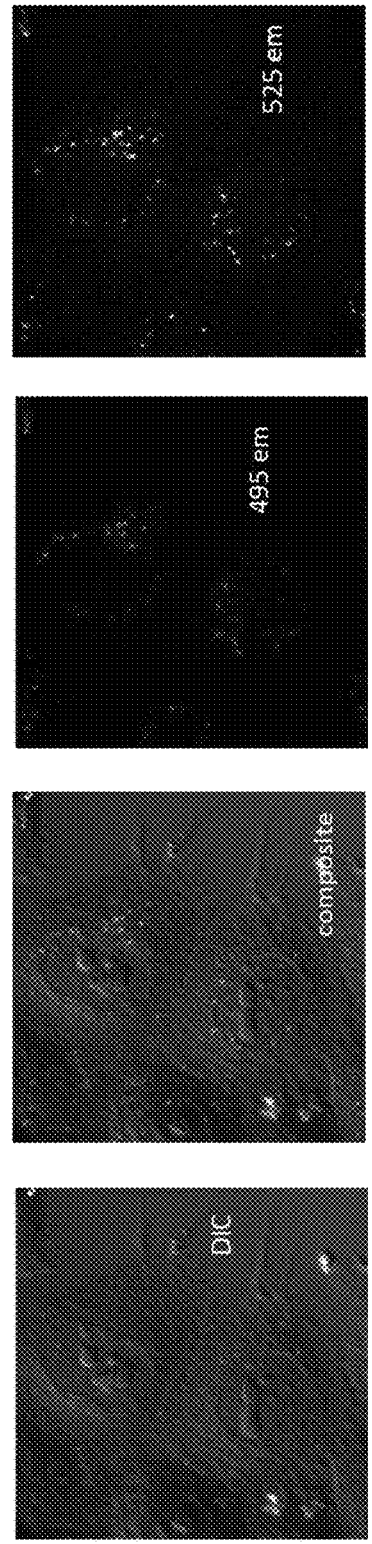

Mass spectrometry was used to determine that nuclear-staining species was either monomethylated diazaxanthylidene 2 or 3. Pure monomethylated Me-2 and monomethylated Me-3 were generated by methylating diazaxanthylidene 1 followed by irradiation with a fluorescent light followed by HPLC purification. Interestingly, both monomethylated photoproducts provided nuclear staining in HeLa cells (FIG. 17). This result supports the hypothesis that the geometry of the scaffold is more significant that the position ("E" vs "Z") of its pyridine nitrogens. However, the methyl-pyridinium was found to be crucial as well: The introduction of compounds 2 and 3 to HeLa cells via DMSO led to the discovery that they are not only cell permeable, but they selectively stain mitochondria rather than the nucleus. A 444 nm excitation was required to image with compounds 2 and 3 (FIG. 18). Compounds Me-2, dimethylated 2 (DiMe-2), compound 10, and DiMe-E-1 were also imaged (FIGS. 19-22, respectively). A subsequent plate reader screen with excitation at 444 nm and subsequent cell staining experiments revealed that monomethylated 3,3'-DAXAZ is a good lysosomal stain. Mass spectral data has identified the non-methylated coupling product of 2-azaxanthione 4 and phenylpyridinethione 5 as compound k.

Figure 23:
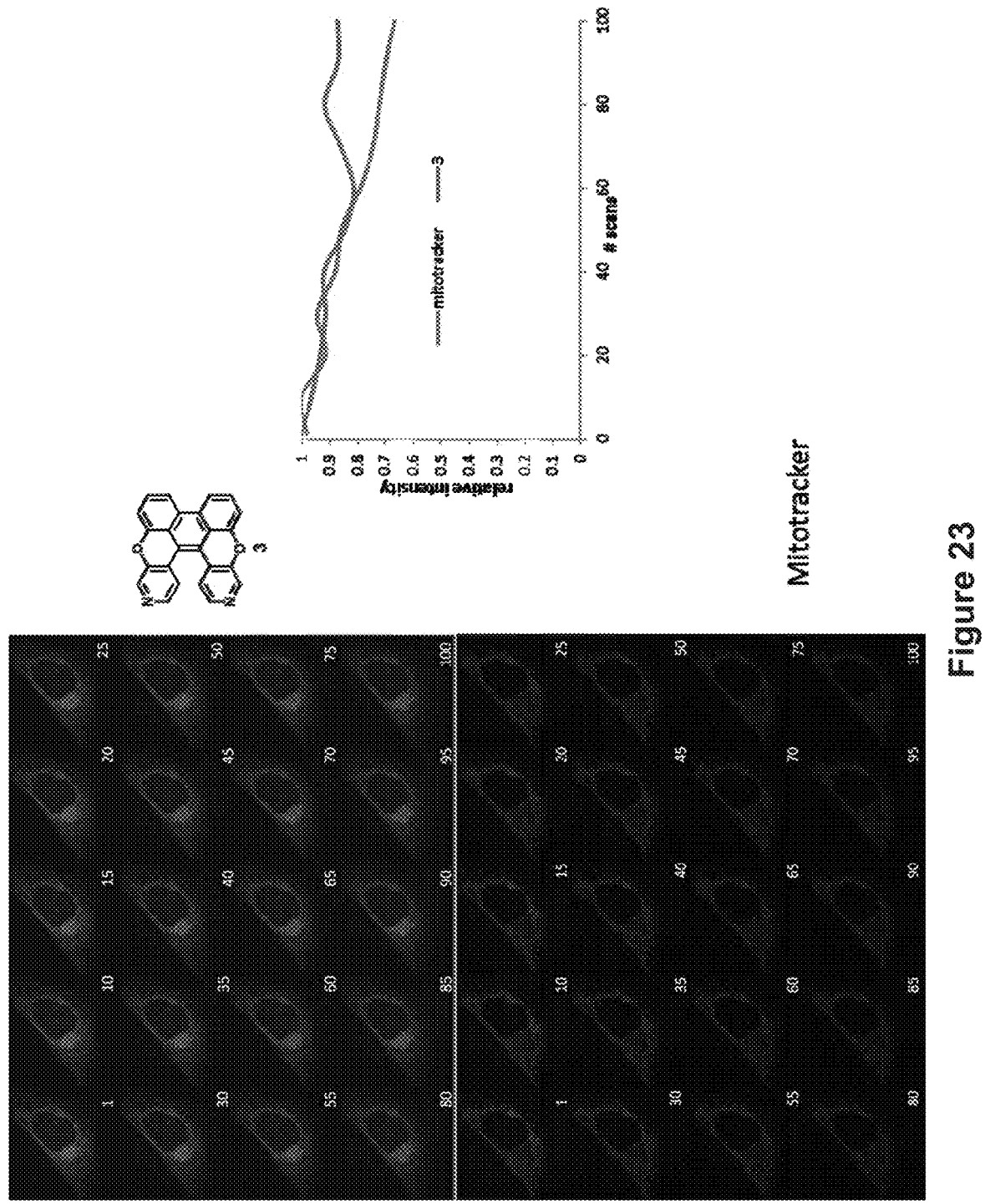
FIG. 23 is a series of images overlaying the emission images of mitotracker red and compound 3.
Figure 24:
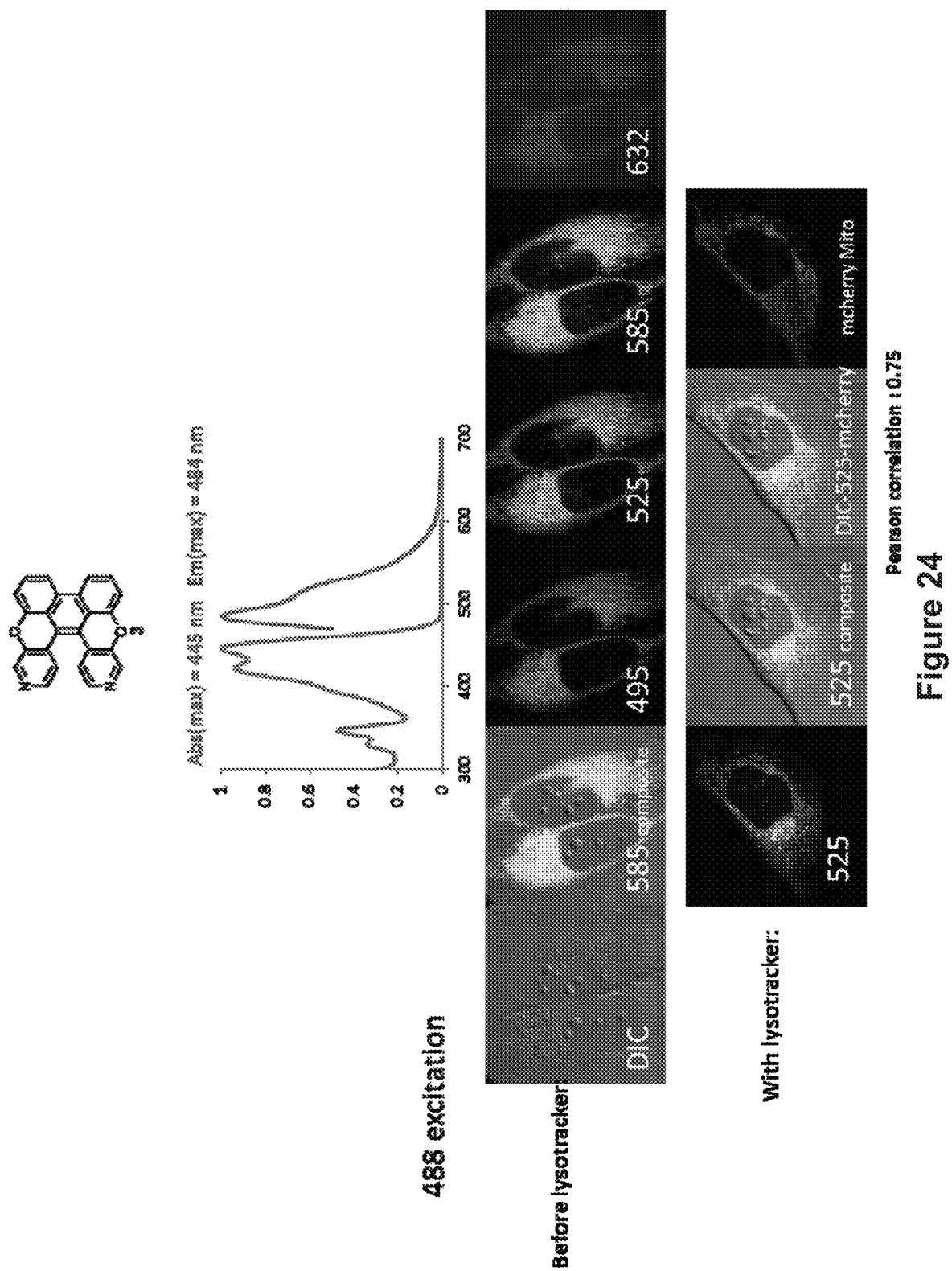
FIG. 24 is a series of images depicting the Pearson correlation value of compound 3, indicating that compound 3 primarily stains mitochondria.
Figure 25:
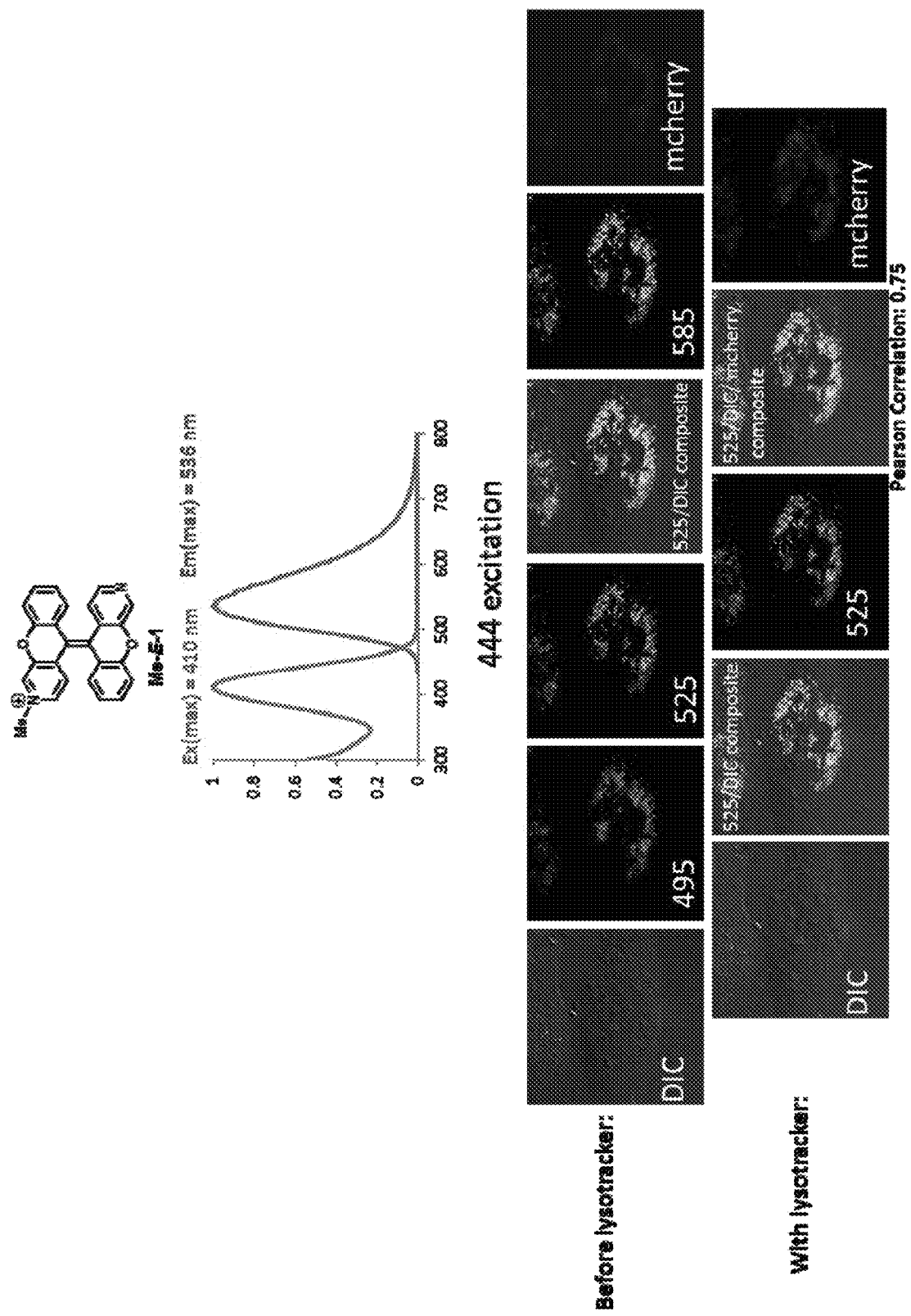
FIG. 25 is a series of images depicting the Pearson correlation between lysotracker red and monomethylated-3, 3'-DAZAX (Me-E-1), indicating that Me-E-1 is a lysosome-specific stain.
Figure 26:
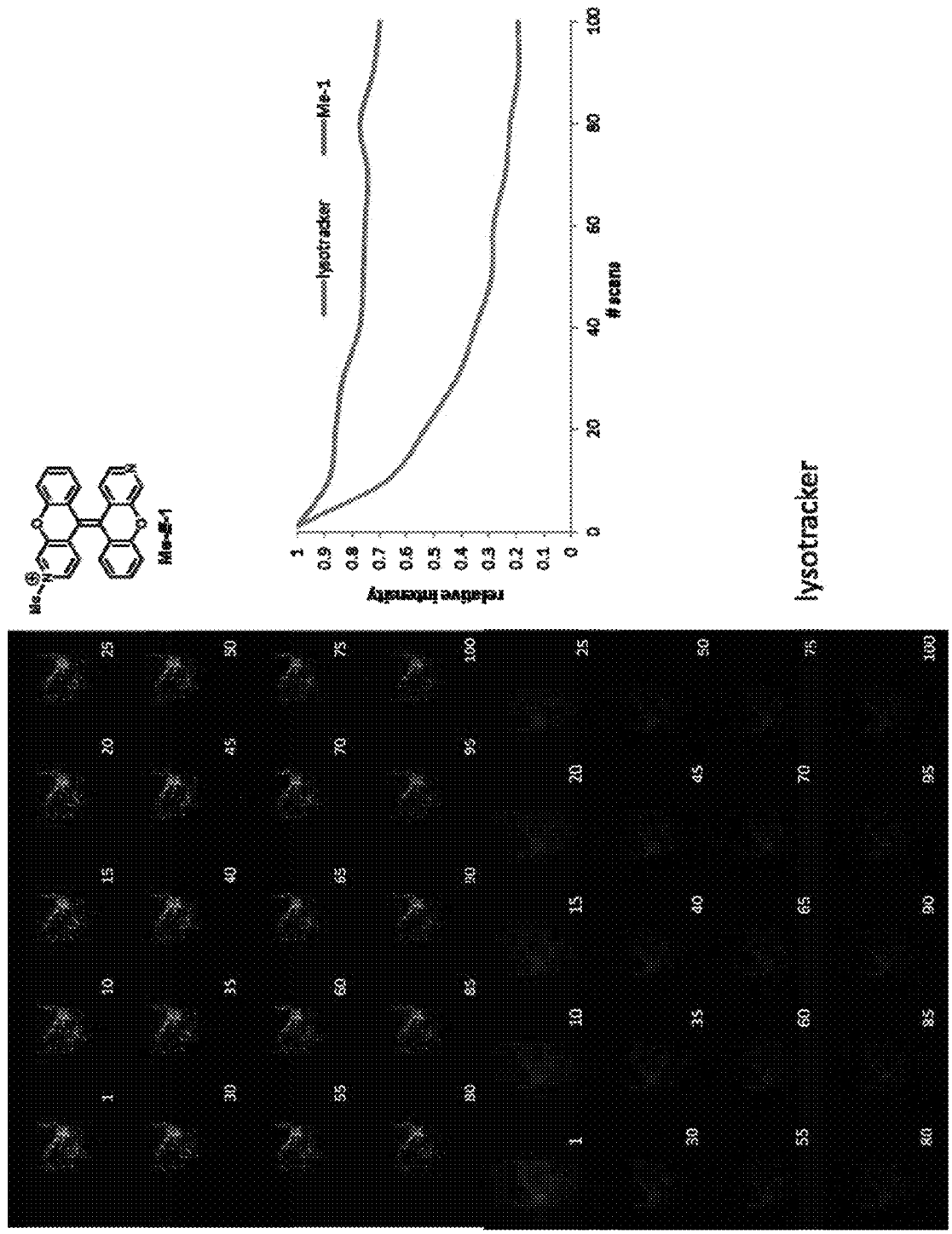
FIG. 26 is a series of images overlaying the emission images of lysotracker red and compound Me-E-1.
Figure 27:
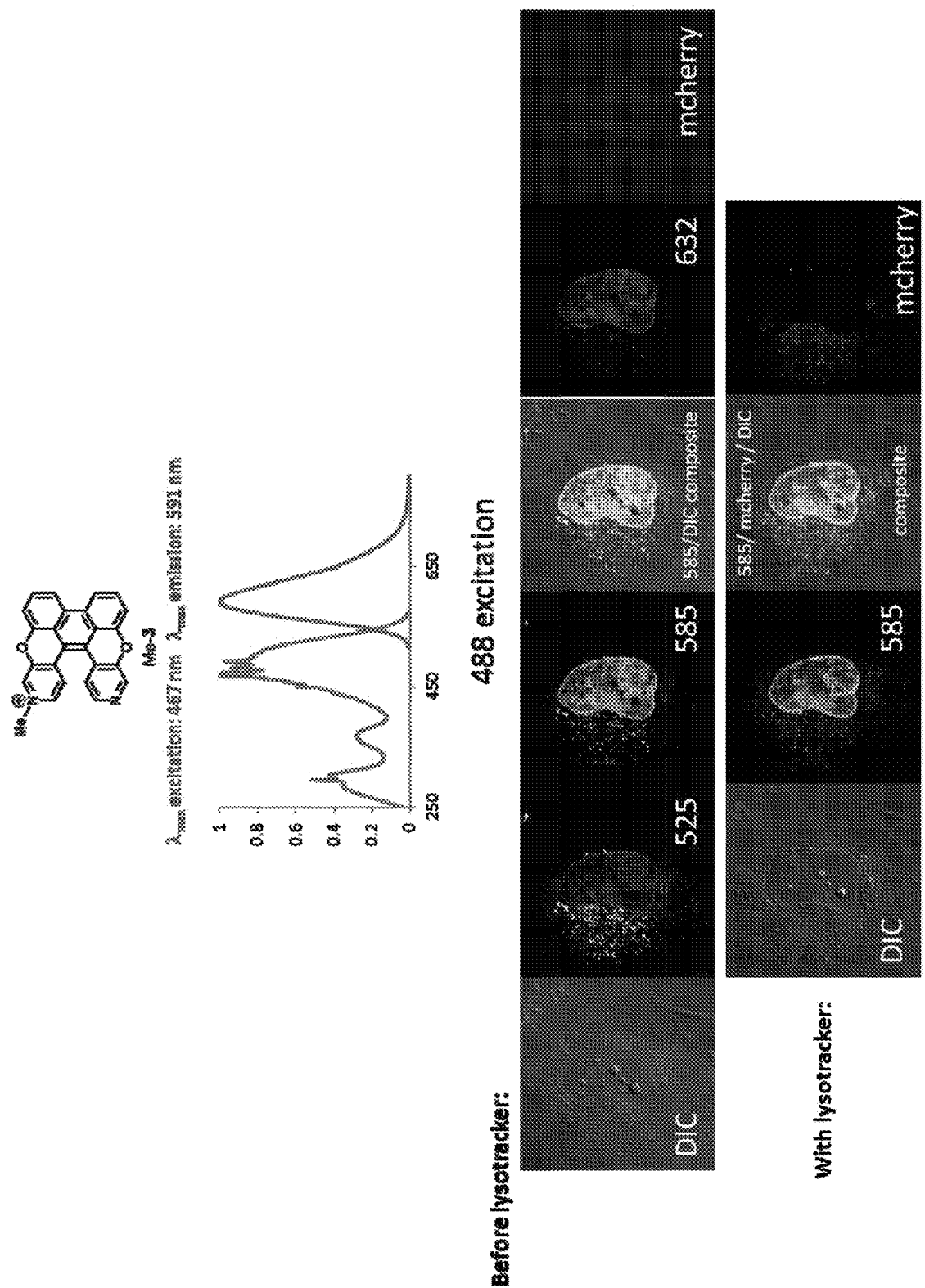
FIG. 27 is a series of images depicting the Pearson correlation between lysotracker red and monomethylated-3 (Me-3), indicating that Me-3 stains lysosomes.
Figure 28:
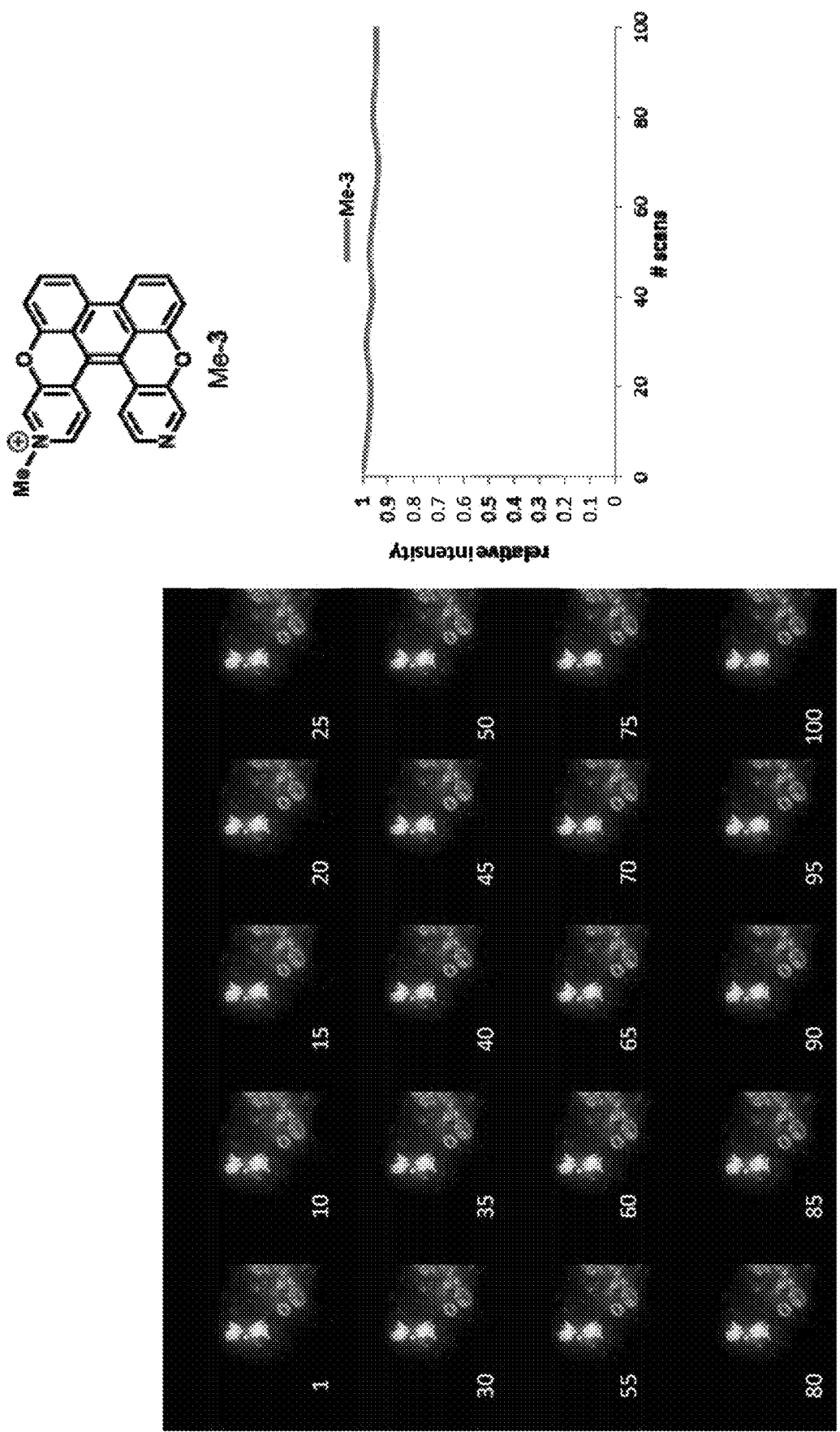
FIG. 28 is a series of emission images of compound Me-3.

Pearson correlations were done after co-staining with mitotracker or lysotracker to evaluate specificity. Overlaying the emission images of mitotracker red and compound 3 makes it clear that compound 3 is staining something in addition to mitochondria (FIG. 23), but a good Pearson correlation value of 0.75 indicates that it primarily stains mitochondria (FIG. 24). Likewise, the Pearson correlation between lysotracker red and monomethylated-3,3'-DAZAX (Me-E-1) was found to be 0.75 (FIGS. 25-26). Although not wishing to be bound by any particular theory, these results indicate that Me-3,3'-DAZAX (Me-E-1) is a lysosome-specific stain. It is apparent that monomethylated-3 (Me-3) stains something other than the nucleus, and a Pearson correlation of 0.25 with lysotracker suggests that it is staining lysosomes (FIGS. 27-28). These results demonstrate that this library approach is effective for generating a variety of dyes for multiple purposes.

Figure 29:
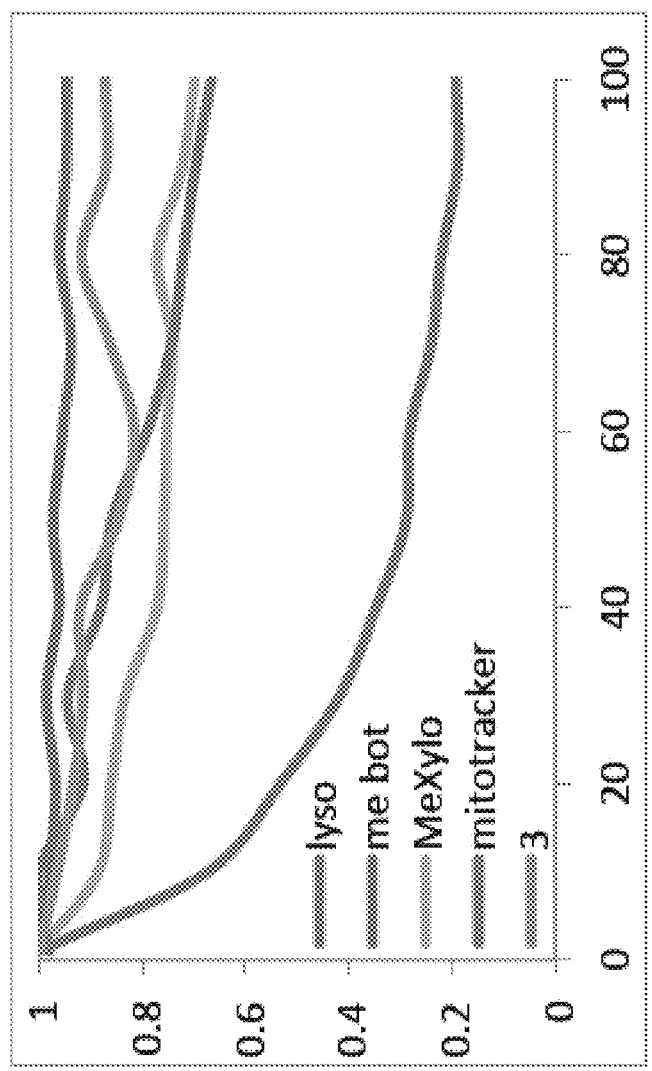
FIG. 29 is a graph evaluating the photostability and/or resistance to photobleaching of compounds Me-3,3'-DAZAX (Me-E-1), 3, and Me-3 compared with the commercial dyes lysotracker and mitotracker.
Figure 30:
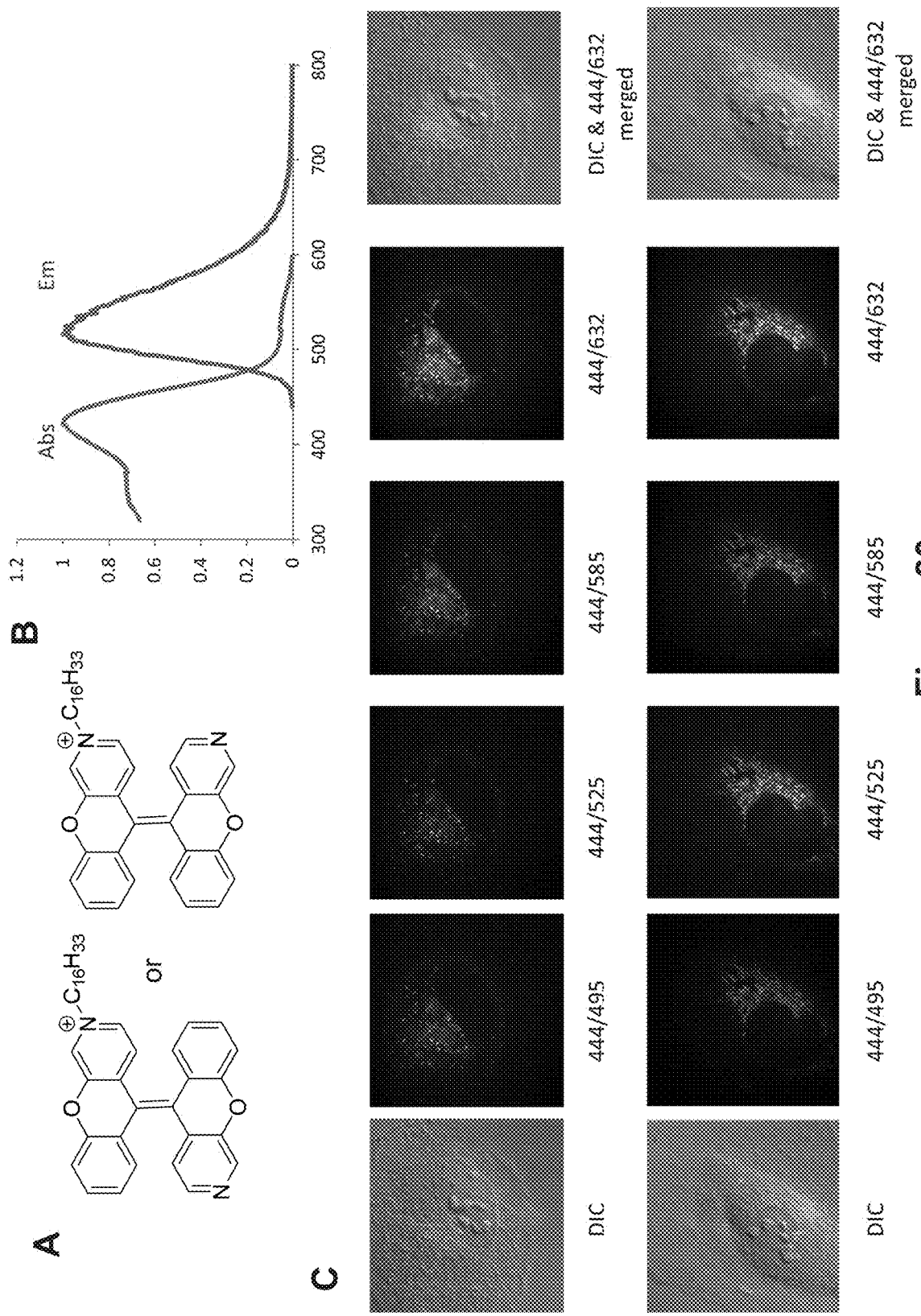
FIG. 30, comprising
Figure 31:
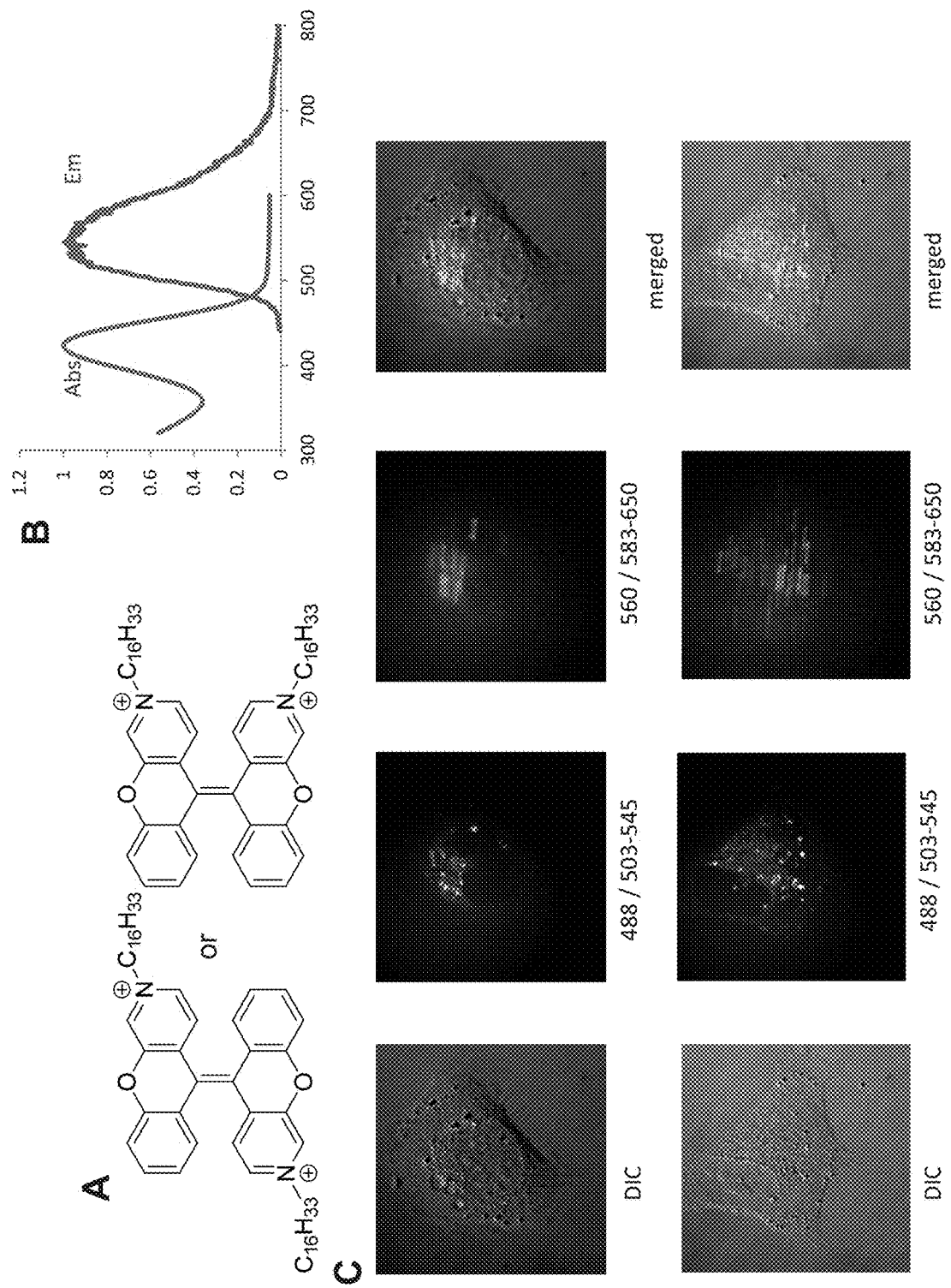
FIG. 31, comprising
Figure 32:
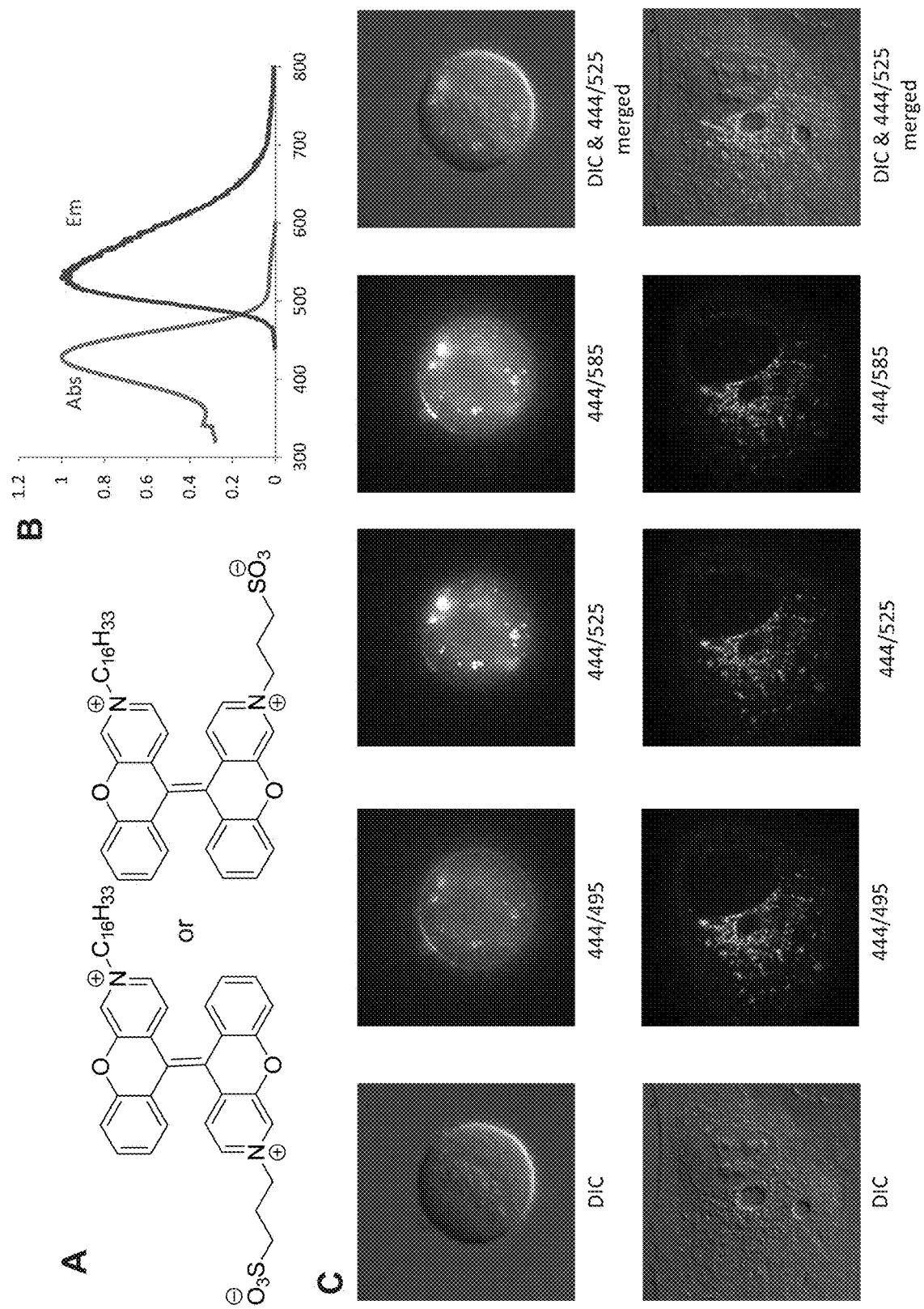
FIG. 32, comprising
Figure 33:
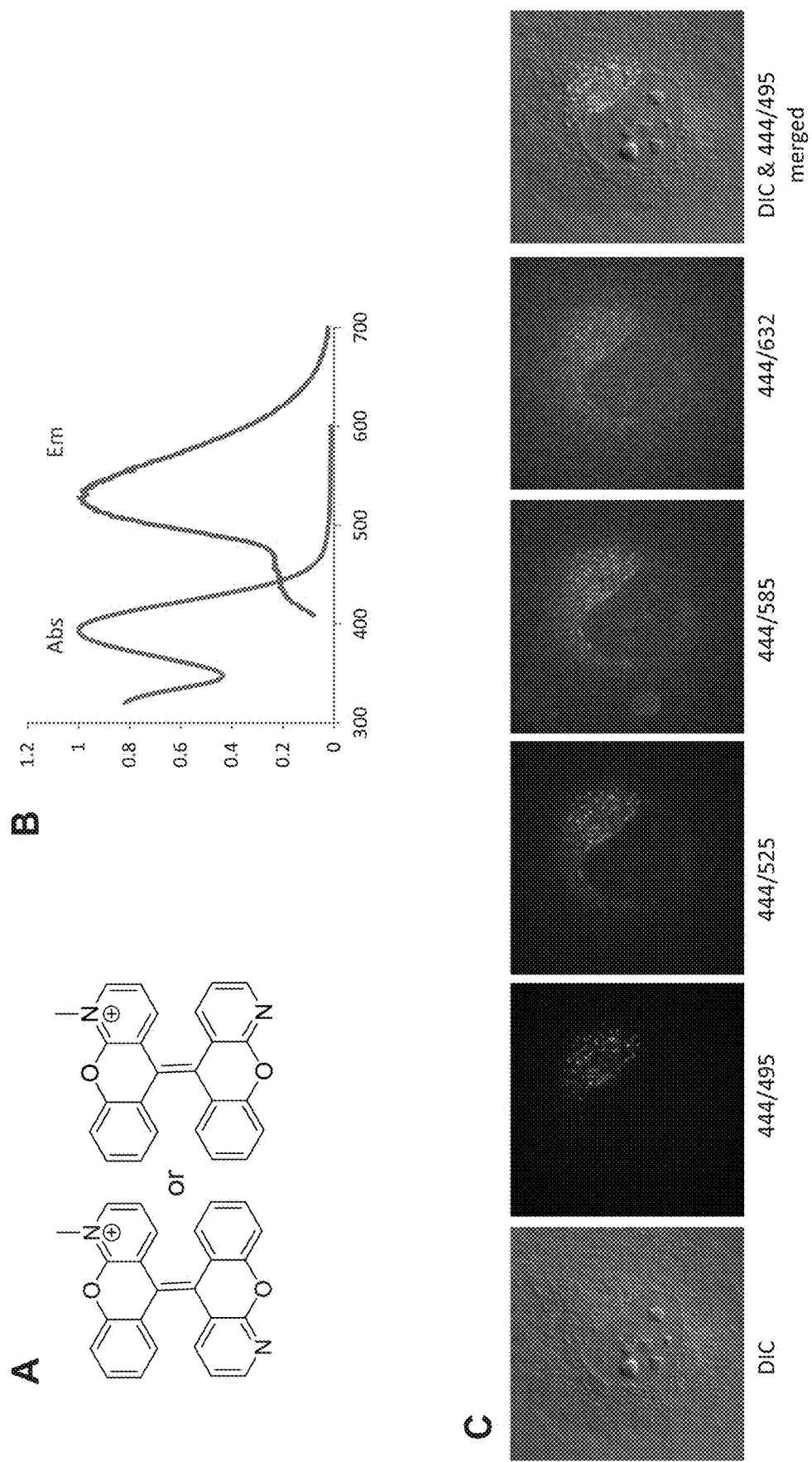
FIG. 33, comprising
Figure 34:
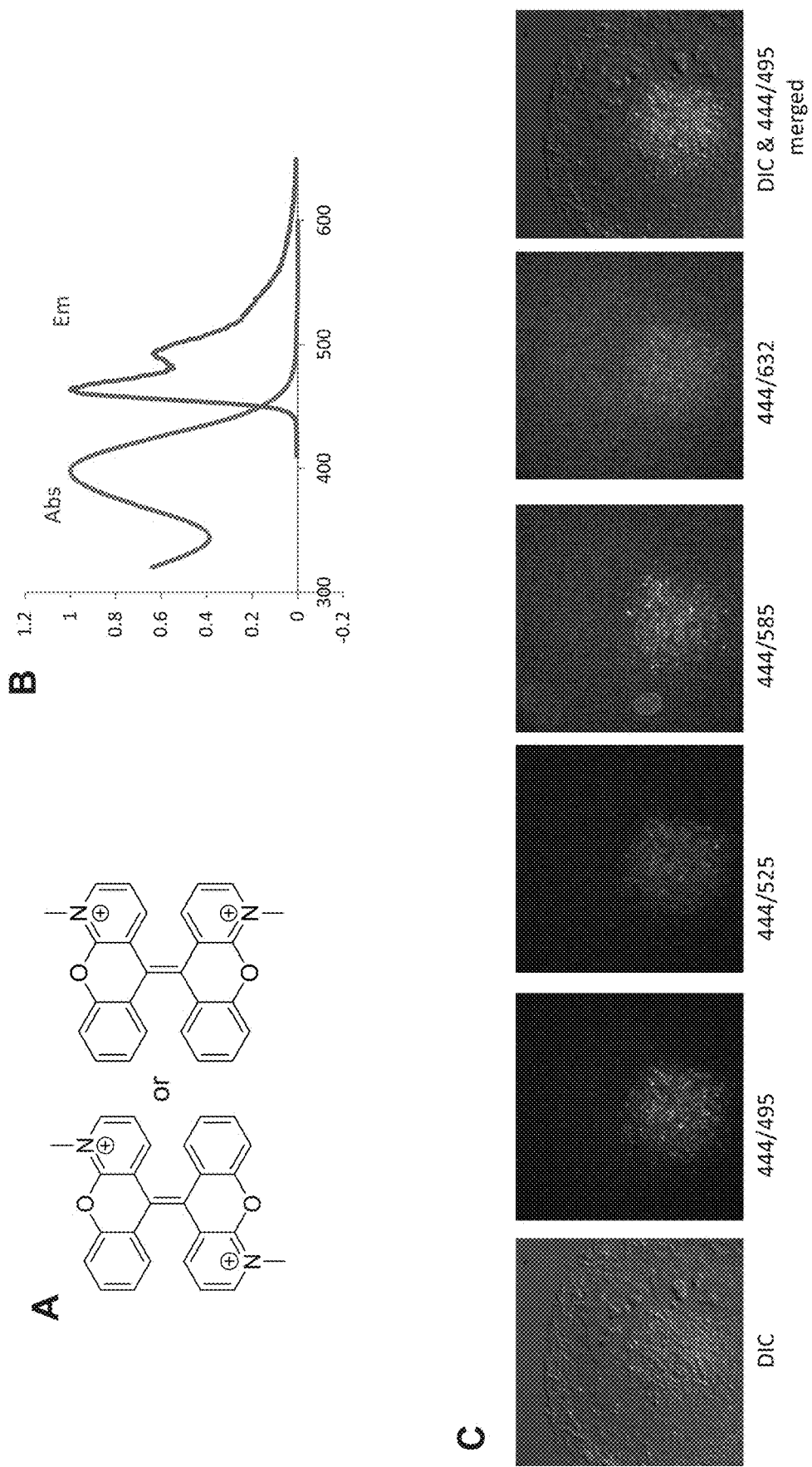
FIG. 34, comprising
Figure 35:
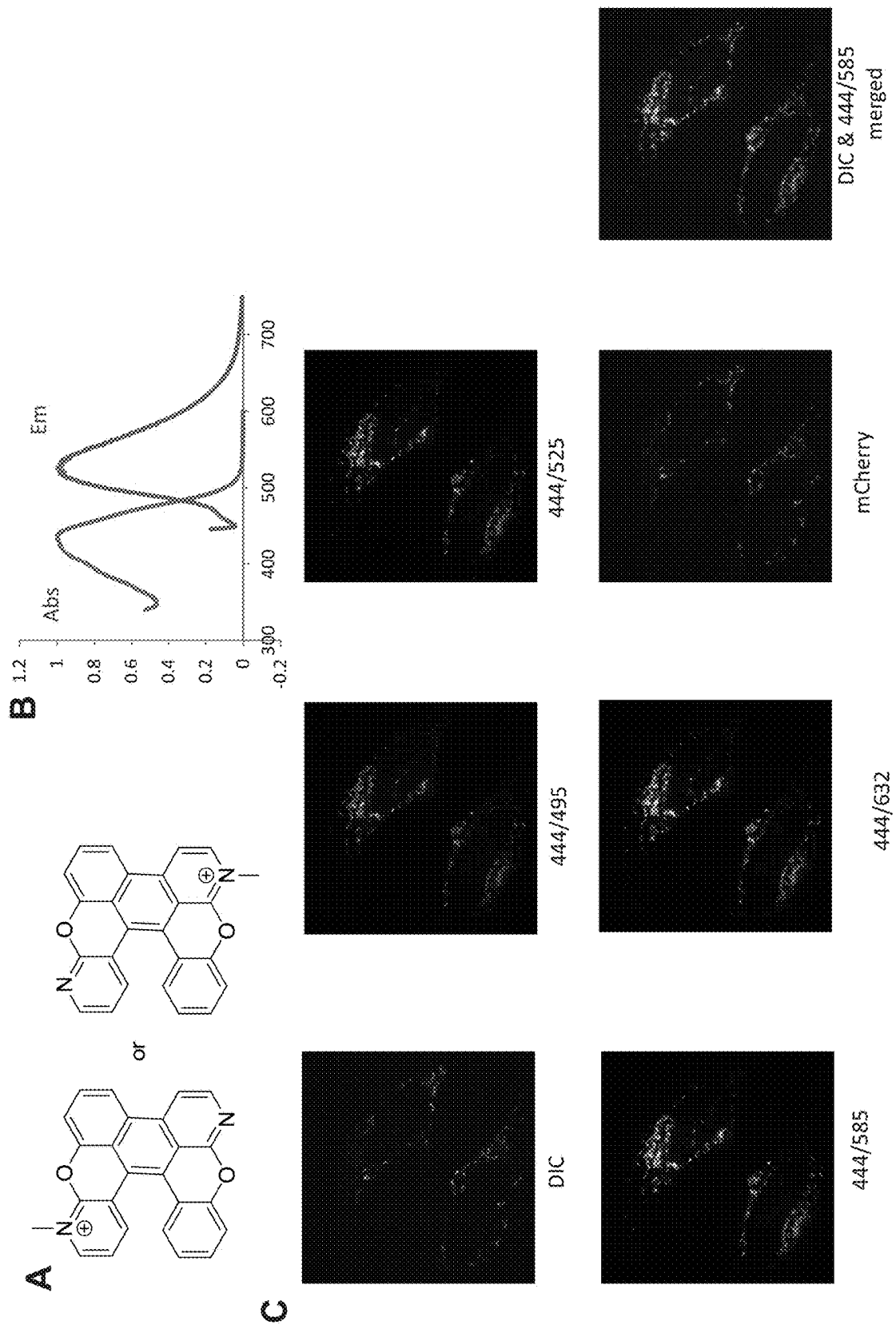
FIG. 35, comprising
Figure 36:
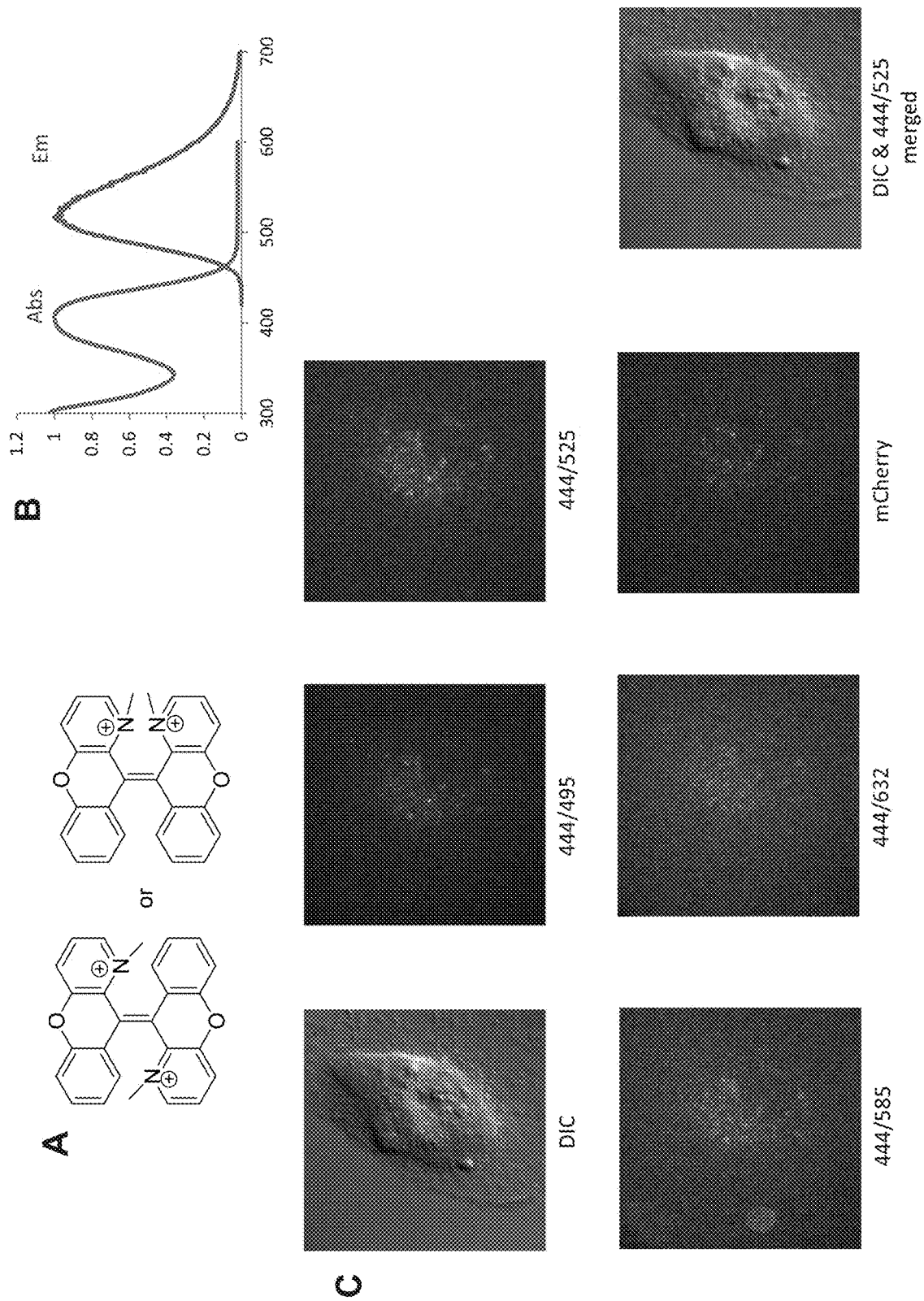
FIG. 36, comprising

One-hundred-time-point microscopy experiments were performed to evaluate photostability and/or resistance to photobleaching in comparison with the commercial dyes of lysotracker and mitotracker. As shown in FIG. 29, all three of the identified stains are less prone to photobleaching than both lysotracker and mitotracker. For these experiments, each sample was pulsed 100 times for 300 ms and the maximum intensity of the image was tracked over time. Me-3,3'-DAZAX (Me-E-1) was found to lose ~30% of its intensity over 100 scans while the lysotracker with which it was co-stained lost 80%. Mitotracker was more robust than lysotracker, losing only 34% of its intensity over the 100 scans, while compound 3 lost only ~13%. The most robust dye discovered thus far is monomethylated-3 (Me-3), which lost only ~5% of its intensity over 100 scans. These results demonstrates that this approach is effective for targeting extensive irradiation of a library, thereby streamlining the discovery of more photostable dye molecules.

Figure 37:
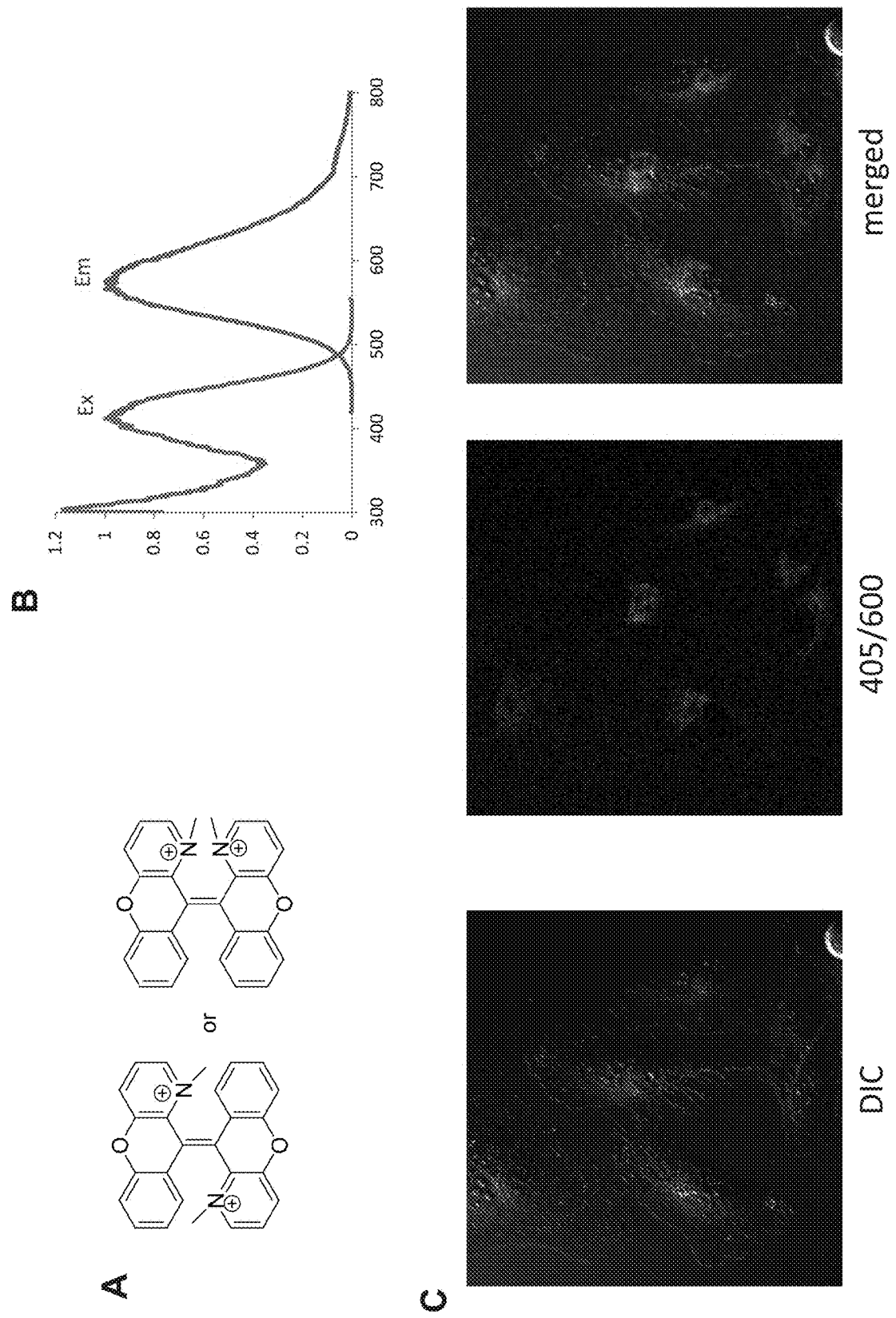
FIG. 37, comprising
Figure 38:
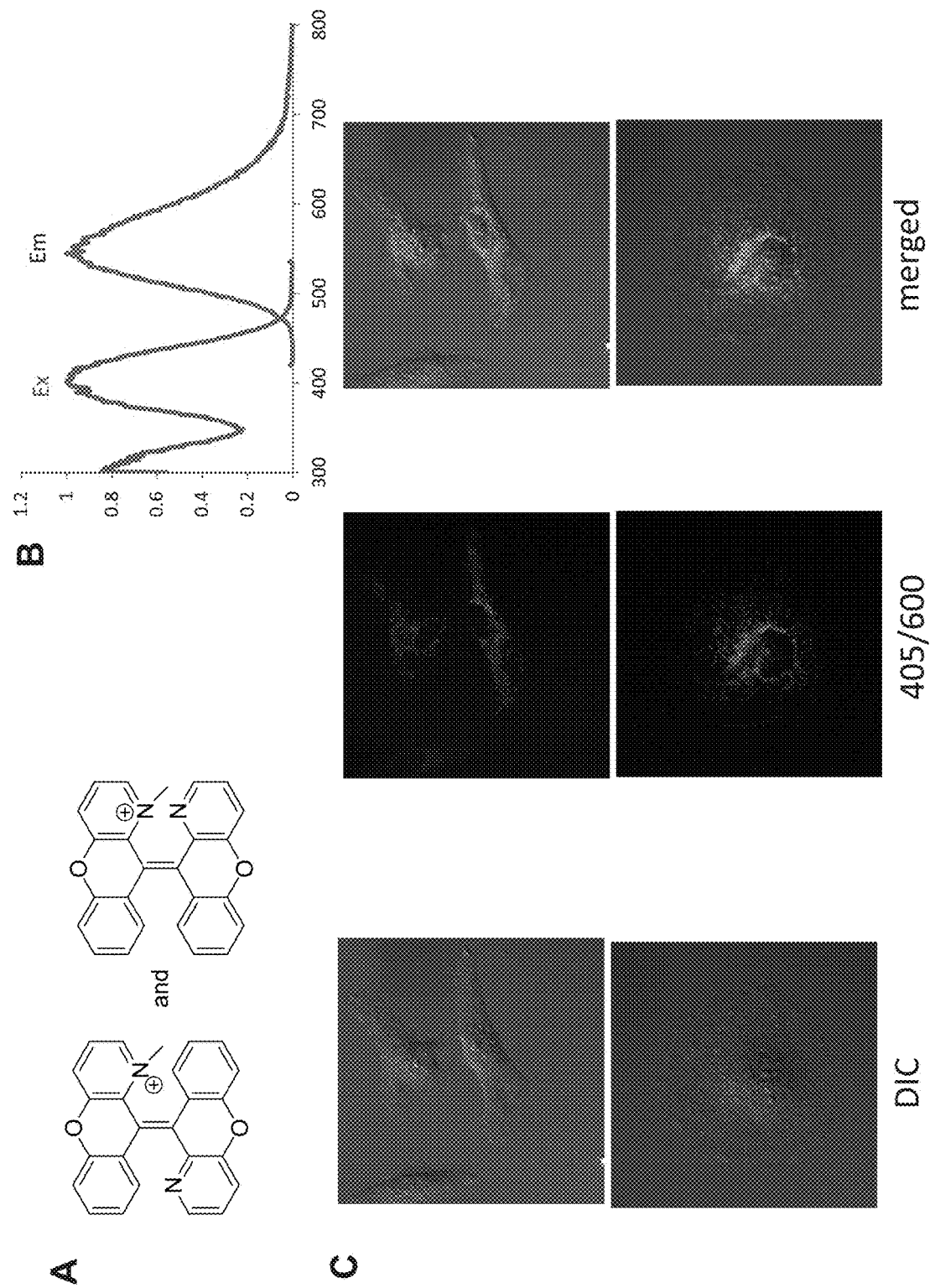
FIG. 38, comprising

This single library has demonstrated trends that the effects perturbations of the DAZAX scaffold have on its staining properties. It was observed that methylation is not a requisite for cell permeability, nor for improving water solubility and red-shifting the chromophore. Methylation of 3 results in a mitochondria-specific stain, while non-methylated 3 is identified as a nuclear stain. The photocyclization reaction can also affect the stain specificity of the compound, as Me-1 is a lysosome-specific stain while Me-3 primarily stains the nucleus. There seems to be no significant difference in the behavior of E- and Z-isomers and their analogous derivatives in this class of compounds, as both compounds 2 and 3 are mitochondria-specific dyes, while their respective monomethylated derivatives are both nuclear stains. FIGS. 30-36 depict the absorption spectra, emission spectra and cell staining images of compounds useful in the invention. FIGS. 37-38 depict the excitation spectra, emission spectra and cell staining images of compounds useful in the invention.

These results demonstrate that a thione-based high throughput approach for stain development is effective. 3,3'-DAZAX provided the inspiration for discovering new bioimaging agents using an expedited approach involving 1) a modular one pot synthetic process with a biarylthione mixture, 2) rapid introduction of diversity via E-/Z-interconversion, methylation and photocyclization, and 3) rapid evaluation using an aqueous workup, extended raditation, HPLC plate reader, and microscopy with HeLa cells. A lower tech approach is also be feasible using TLC and a fluorimeter. From a three thione mixture that could provide over forty new compounds was discovered eight new water-soluble, cell-permeable, photo-stable dyes with convenient excitation at 488 nm and a variety of specificities including mitochondrial and nuclear staining. These results support the hypotheses that 1) pyridine methylation has a drastic effect on site selectivity in addition to solubility and red-shifting dyes, 2) photocyclization effects site selectivity, and 3) E-/Z-isomers do not have a drastic effect on any relevant staining property.

Example 2

Synthesis and Properties of Lysosome Specific Photoelectrocyclization Probes for Live Cell Imaging The results described herein demonstrate that the bis-tricyclic aromatic ene (BAE) 3,3'-diazaxanthylidene scaffold serves as a template for discovering photo-resistant cell-permeable fluorophores with subcellular specificities for mitochondria and lysosomes. This class of compounds demonstrates effective bis-tricyclic heteroaromatic ene (BHAE)-derived fluorophores with good biocompatibilities, specificities for lysosomes or mitochondria, and minimal synthetic demand that lends itself to the tunability that has proven so effective with the more commonly reported BODIPY and cyanine dyes. Bathochromatic emission and excitation shifts were achieved upon either N-methyl-pyridinium formation or intramolecular photolytic oxidative couplings of aromatic rings. Crystal structures confirmed that the oxidative coupling results in a conformational change that can account for the red shift and corresponds to changes in subcellular specificity. The cationic N-methyl pyridinium species were also shown to have different subcellular localization patterns than their neutral analogs. Lysosome-specific and mitochondria-specific stains with greater resistance to photobleaching than known stains Lysotracker Red™ and Mitotracker Red™ are demonstrated.

Figure 39:
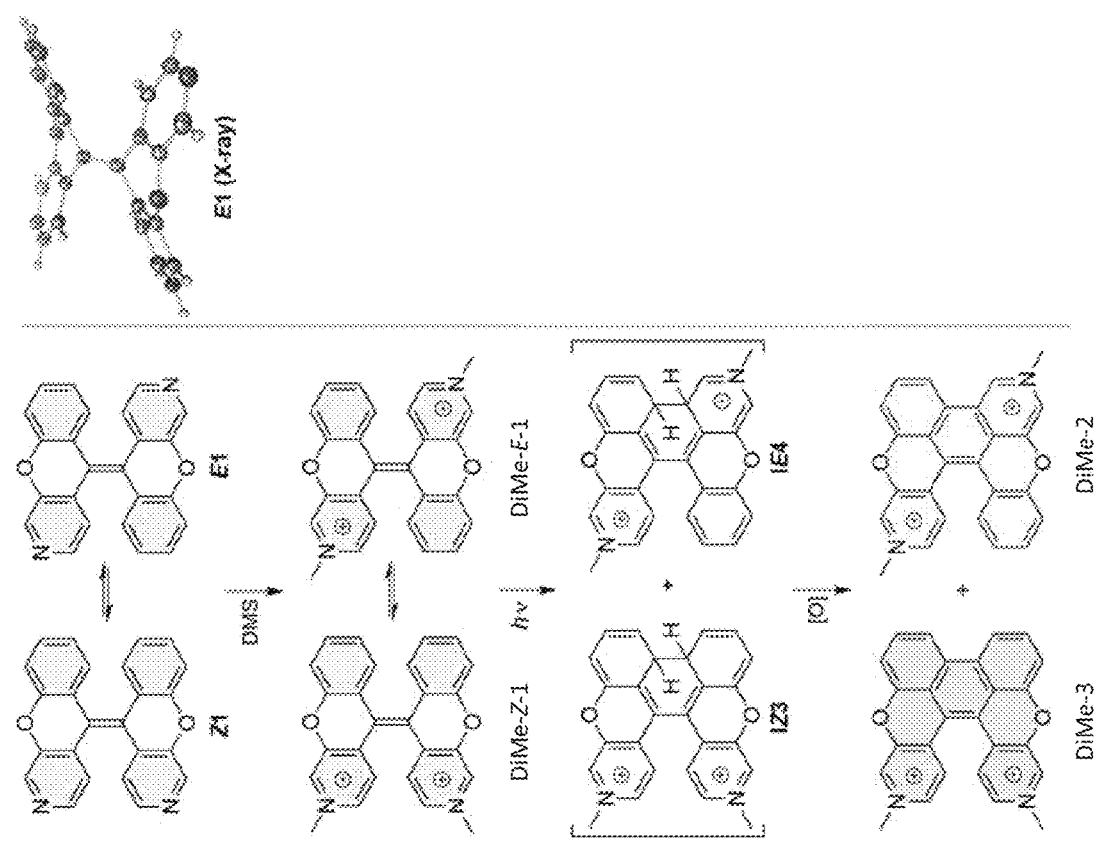
FIG. 39, comprised of FIGS. 39A-39C, depicts exemplary compounds.
Figure 40:
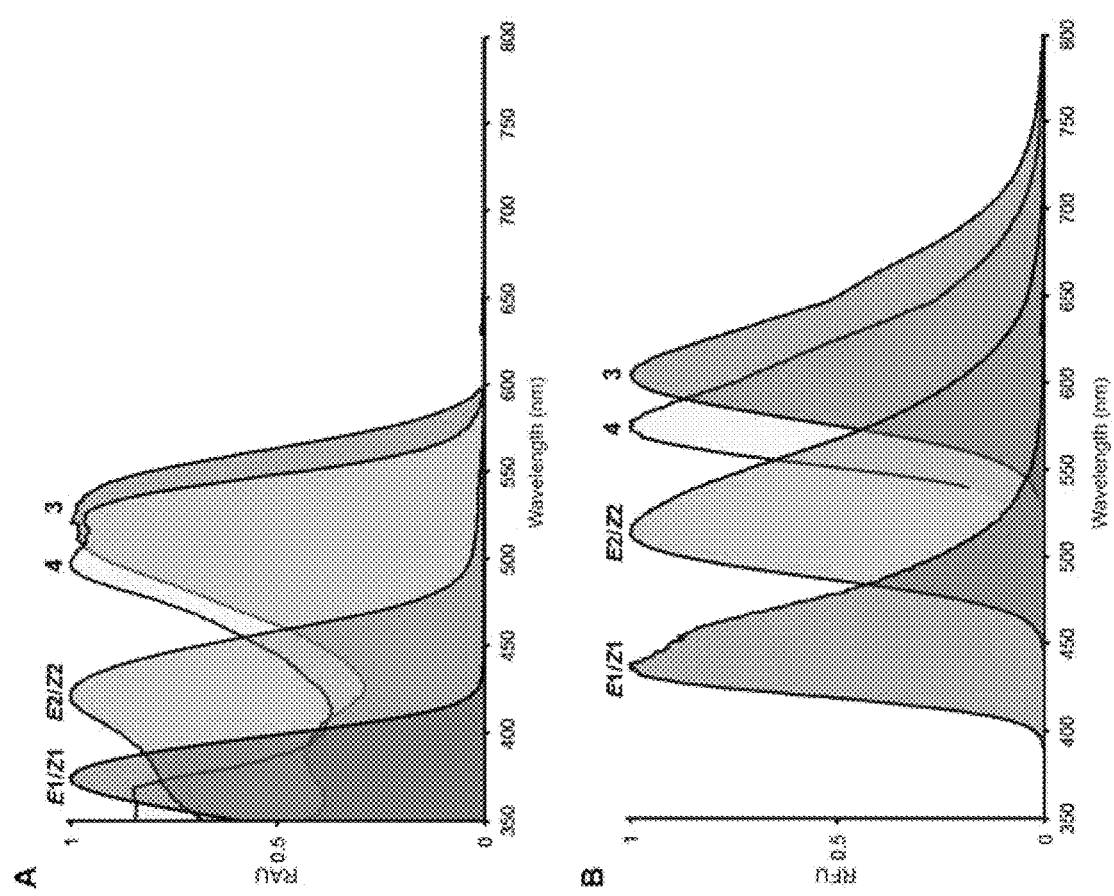
FIG. 40, comprised of FIGS. 40A-40B, depicts a series of absorption and excitation/emission spectra of exemplary compounds of the invention.

The bis-tricyclic heteroaromatic ene 2,2'-diazaxanthylidene (E/Z-1) was previously synthesized to investigate its ability to bind β-form DNA. The bis-N-methylation of the blue-emissive E/Z-1 resulted in the bis-N-methylpyridinium species DiMe-E-1 and DiMe-Z-1 (FIG. 39), which had red-shifted excitation and emission profiles (FIG. 40). A similar red-shift was also observed upon exposing a colorless solution of E/Z-1 to direct sunlight for a day. TLC analysis of the resulting yellow-emitting solution revealed trace amounts of photoproducts 9,14-diaza-benzo[1,2,3-kl: 6,5,4k'l']di-xanthene (3) and 2,9-diaza-benzo[1,2,3-kl:6,5, 4k'l']dixanthene (2). The yield of 2 and 3 was improved under Mallory conditions: photolysis of a THF solution of E/Z-1, methyloxirane, and iodine in a Rayonet photo-reactor provided a 32:68 mixture of 2:3 in 74% yield (FIG. 39A). Although not wishing to be bound by any particular theory, it is likely that 3 comes from Z-1 and 2 from E-1 via intramolecular oxidative coupling. Neither of the dihydrophenanthrene intermediates IZ-1 or IE-1 were isolable from the reaction mixture. X-ray crystallography was used to confirm the structure of 2. Comparing the crystal structures of 1 and 2, it is clear that the red shifted emission of 2 is the result of increased planarity within the scaffold, allowing for greater electron delocalization through the extended π-system (FIG. 39B).

Bis-N-methylpyridinium formation from and intramolecular oxidative coupling with E/Z-1 caused bathochromic shifts in emission and excitation. Oxidative coupling provided a greater excitation shift while dimethylation provided a greater emission shift. These trends were consistent upon the synthesis of dimethylated photoproducts DiMe-2 and DiMe-3 which were pursued via several synthetic approaches. Bis-N-Methylpyridinium species DiMe-2 and DiMe-3 were easily accessible from pure 2 and 3, respectively, but the purification of 2 and 3 was inconvenient on scale. Therefore, DiMe-2 and DiMe-3 were pursued by first forming DiMe-E-1 and DiMe-Z-1, which was easy to purify on C18-silica gel. The conversion of E/Z-6 into DiMe-2 and DiMe-3 was not viable using the original Rayonet conditions, however it was discovered that superior conversion could be achieved using visible light photolysis without any catalyst.

Figure 41:
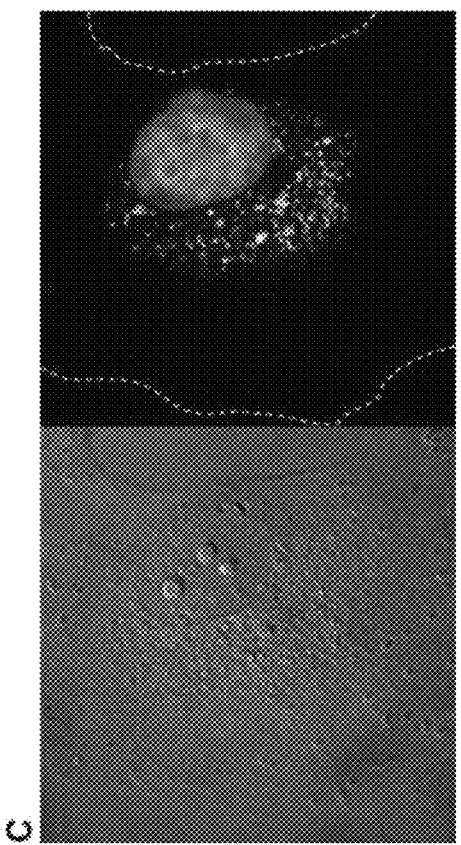
FIG. 41, comprising
Figure 41:
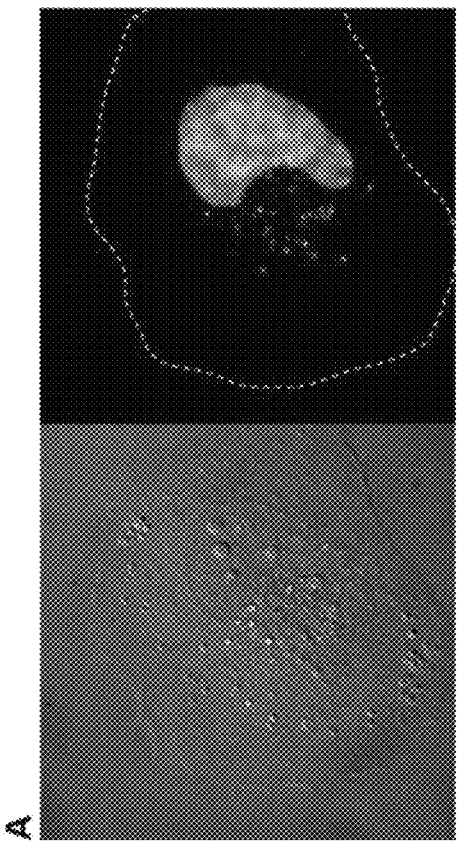
Figure 41:
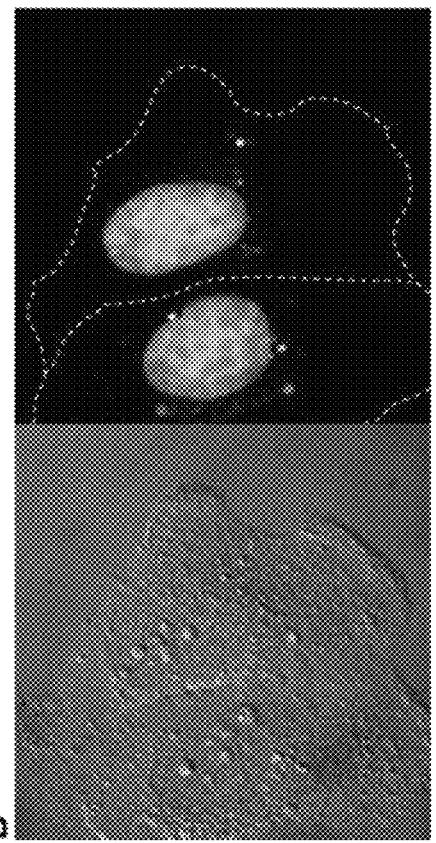

Confocal microscopy revealed that the poor solubility of E/Z-1 in DMSO precluded live-cell imaging, but that fluorophores 2, 3, DiMe-2, DiMe-3, DiMe-E-1, and DiMe-Z-1 are all cell permeable and non-toxic to HeLa cells on a 24 h timescale. Neutral photoproducts 2 and 3 appeared to localize primarily in the mitochondria of HeLa cells, while the N,N-dimethylated species DiMe-2, DiMe-3, DiMe-E-1, and DiMe-Z-1 were specific for punctuate organelles in HeLa cells, which were believed to be lysosomes (FIG. 41).

Confirmation of the supposed lysosome and mitochondria staining was achieved by doing co-staining experiments with Lysotacker Red™ and Mitortracker Red™, respectively. A Pearson colocalization correlation (PCC) of 0.75 was determined from a costaining experiments in which HeLa cells were incubated with E/Z-2 and Lysotracker. The imperfect correlation is due to higher specificity for a subset of vesicles stained by the Lysotracker. Although not wishing to be bound by any particular theory, it is hypothesized that E/Z-2 is a lysosome-specific stain. Compound 2 exhibited a PCC of 0.75 vs Mitotracker Red, indicating significant but not complete colocalization. Fluorescence images of cells co-stained with 2 and Mitotracker Red show that 2 stains mitochondria and additional structures.

Figure 42:
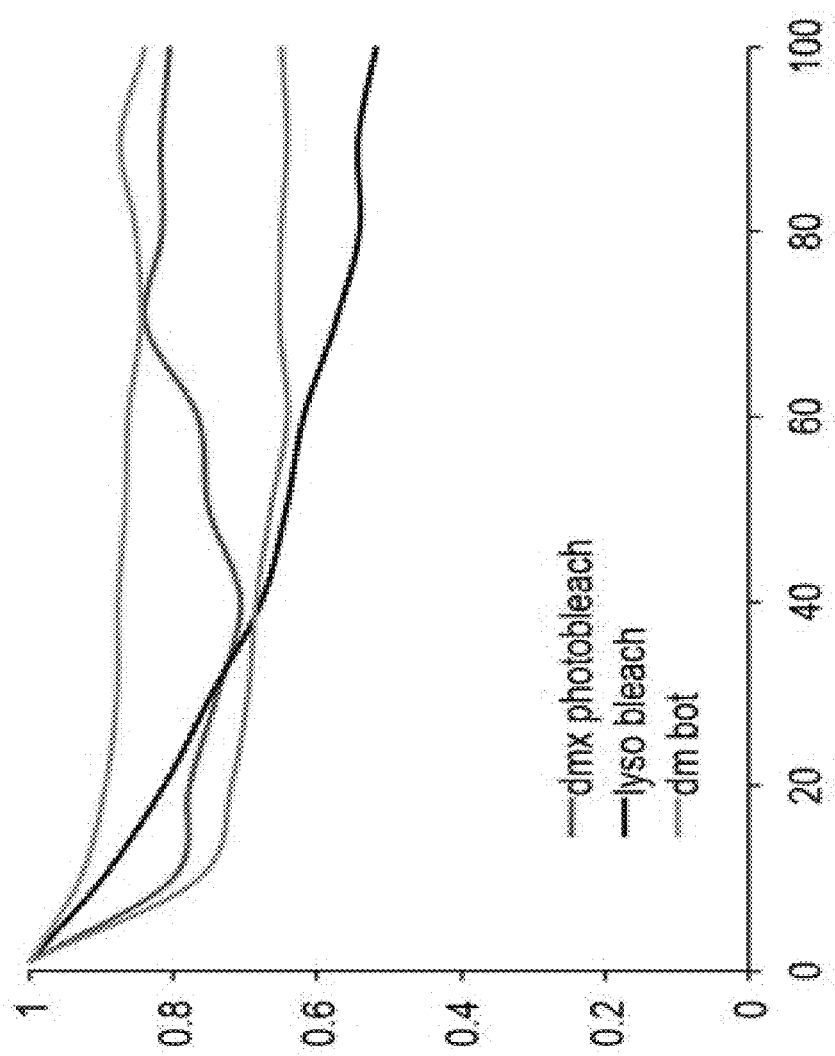
FIG. 42 is a normalized plot depicting experimental data of the average intensity of sequential images monitored over 100 laser pulses of 300 ms. This data in the graph compares the relative photostabilities of DiMe-Z-1, DiMe-E-1, and 3 with Lysotracker Red™ and Mitotracker Red™, respectively.

The in vivo photostabilities of DiMe-E-1, DiMe-Z-1 and 2 were found to be superior to Lysotracker Red™ and Mitotracker Red™, respectively (FIG. 42). This was determined via one-hundred-time-point timelapse microscopy experiments in which the average intensity of the image was monitored over 100 laser pulses of 300 ms (FIG. 42). The mono-N-methylpyridinium species, which were generated in minor amounts when treating 1-3 with excess dimethylsulfate in 55° C. chloroform, displayed similar photophysical properties, subcellular localizations, and photo stabilities to their corresponding dimethylated species DiMe-2, DiMe-3, DiMe-E-1, and DiMe-Z-1.

In terms of controlling subcellular localization, the conformation of the fluorophore scaffold appears to be insignificant compared to the absence/presence of the pyridinium cations. The presumably anti-folded dication E/Z-6 stains lysosomes as effectively as its more planar photo-derivatives DiMe-2 and DiMe-3. Although not wishing to be bound by any particular theory, the fact that the neutral photoproducts 2 and 3 both stain mitochondria suggests a) that the charge(s) on nitrogen(s) may be critical to subcellular localization for this scaffolds, and b) that the positional relationship of the pyridine moieties on the scaffold has no blatant localization effects. The mitochondrial staining of 2 and 3 is not identical, however, as 3 appears to also stain some punctuate vesicles that 2 does not. This subtle difference suggests that 2 is may be an improved mitochondrial stain over 3. Although not wishing to be bound by any particular theory, this result suggests that a pyridinium species other than the methyl derivative may achieve a more blatant differentiation of the isomers' localization patterns.

In conclusion, it has been demonstrated that photolysis of 2,2'-diazaxanthylidene (E/Z-1) provides two isomeric Mallory products that are bathochromatically shifted, biocompatible, cell-permeable, non-toxic, mitochondria-specific photo-stable fluorophores 2 and 3. Furthermore, it has been shown that the dimethylated bis-N,N-pyridinium derivatives of 1, 2, & 3 (DiMe-E-1 and DiMe-Z-1, DiMe-2, & DiMe-3, respectively) provide further bathochromatic shifts, the convenience of water-solubility, and a switch to lysosomal subcellular specificity. The ease with which the parent scaffold E/Z-1 can be derivatized[ref], and the ease with which it can be photolyzed and/or functionalized at its pyridine nitrogens to tune its photophysical properties and subcellular specificity demonstrates the versatility that bis-tricyclic heteroaromatic ene (BHAE) scaffolds can provide the bioimaging community.

Example 3

Photoelectrocyclization Turn-On Probe for Organelle Specific Spatiotemporally Defined Live Cell Imaging The results described herein demonstrate a new concept for photoactivatable organelle specific live cell imaging probes based on a 6π-electrocyclization/oxidation mechanism. Photoactivatable fluorophores are useful tools in live cell imaging due to their potential for precise spatial and temporal control. These results demonstrate the synthesis of diazaxanthilidene derivatives that are useful as a probe and are water-soluble, cell permeable, non-cytotoxic, photoactivatable, and can selectively stain mitochondria. The probe displays large Stokes shifts in both pre-activated and activated forms, allowing simultaneous use with common dyes and fluorescent proteins. Sequential single cell activation experiments in dense cellular environments demonstrate high spatial precision and utility in single or multi cell labeling experiments.

The photoactivation mechanism for this probe is based on a photochemically allowed 6π-electrocyclization/oxidation sequence. The unique preorganization imposed by the molecular architecture of the molecule biases the favored conformation needed for efficient photochemically allowed electrocyclization. These results describe a cell permeable, mitochondrial specific, photoactivatable probe with utility in spatially defined cellular imaging applications. This new mitochondrial probe displays decreased cytotoxicity compared to a frequently reported mitochondrial fluorescent probe. The probe is water-soluble and can be excited between 375-450 nm, an excitation wavelength currently not accessible by most commonly used MitoTracker dyes (Johnson, 2010, Molecular probes handbook: a guide to fluorescent probes and labeling technologies, 11th ed., Life Technologies Corp., USA), providing more choices for multi-dye or fluorescent protein imaging experiments. Also demonstrated is its utility in spatiotemporally defined live-cell imaging of mitochondria in dense cellular populations through sequential single cell activation experiments.

Materials and Methods:
General Information n-Butyllithium in hexanes was purchased from Acros and titrated with diphenylacetic acid, which was recrystallized from toluene. All other reagents were purchased from Sigma Aldrich and used without further purification. Solvents were purchased from either Sigma Aldrich or Fisher Scientific.

Anhydrous solvents were purchased from Fisher Scientific and dried by passing through an alumina column of a solvent purification system. Silica gel (230-400 mesh) used for column chromatography was purchased from Silicycle. Thin layer chromatography plates (250 μm thickness) were purchased from Sorbent Technologies. Revered-phase column chromatography was done using a RediSep Rf Gold C18 column on a Teledyne Isco CombiFlash Rf system. High-performance liquid chromatography (HPLC) was performed on a Jasco HPLC system using a Phenomenex column (Luna 5u C18(2) 100A; 250×4.60 mm, 5 micron). UV absorption spectra were obtained on a Jasco V-650 spectrophotometer using a 1 cm path length quartz cuvette. Fluorescence emission spectra were taken on a Horiba Jobin-Yvon FluoroLog using a 1 cm path length fluorescence quartz cuvette. $^1$H-NMR and $^{13}$C-NMR were recorded on either a Bruker DMX 500 (500 MHz) or a Bruker AVII 500 (500 MHz). High-resolution mass spectrometry was performed using a Waters LCT Premier XE Mass Spectrometer (model KE 332). X-ray chromatography was performed using a Bruker APEX2-DUO CCD X-ray Diffractometer. Photoreactions were carried out in a Rayonet Photochemical Reactor (model RPR-100). Quantum yield was determined by serial dilution method using coumarine 153 (in ethanol, Φ=0.38) and fluorescein (in NaOH 0.1 M, Φ=0.95) as standards (Yvon, A guide to recording Fluorescence Quantum Yields, http://www.horiba.com/fileadmin/uploads/Scientific/Documents/Fluorescence/quantumyie ldstrad.pdf, accessed Jul. 13, 2014; Brouwer, 2011, Pure Appl. Chem. 83: 2213-2228)

Experimental Procedures
Synthesis of Compound 12:

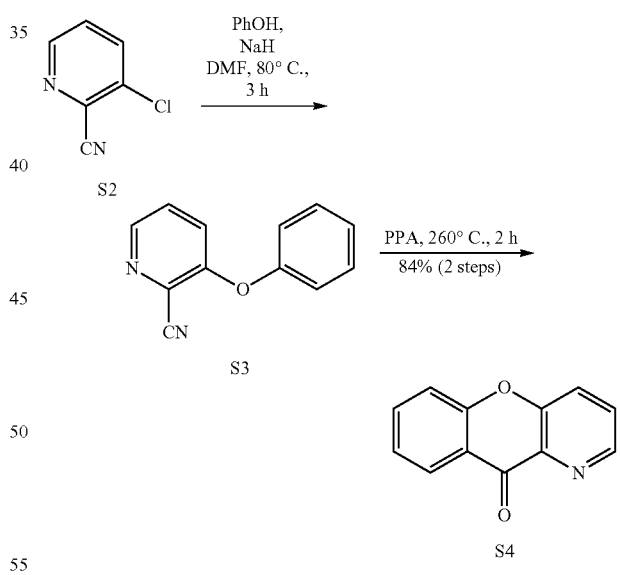

Figure 59:
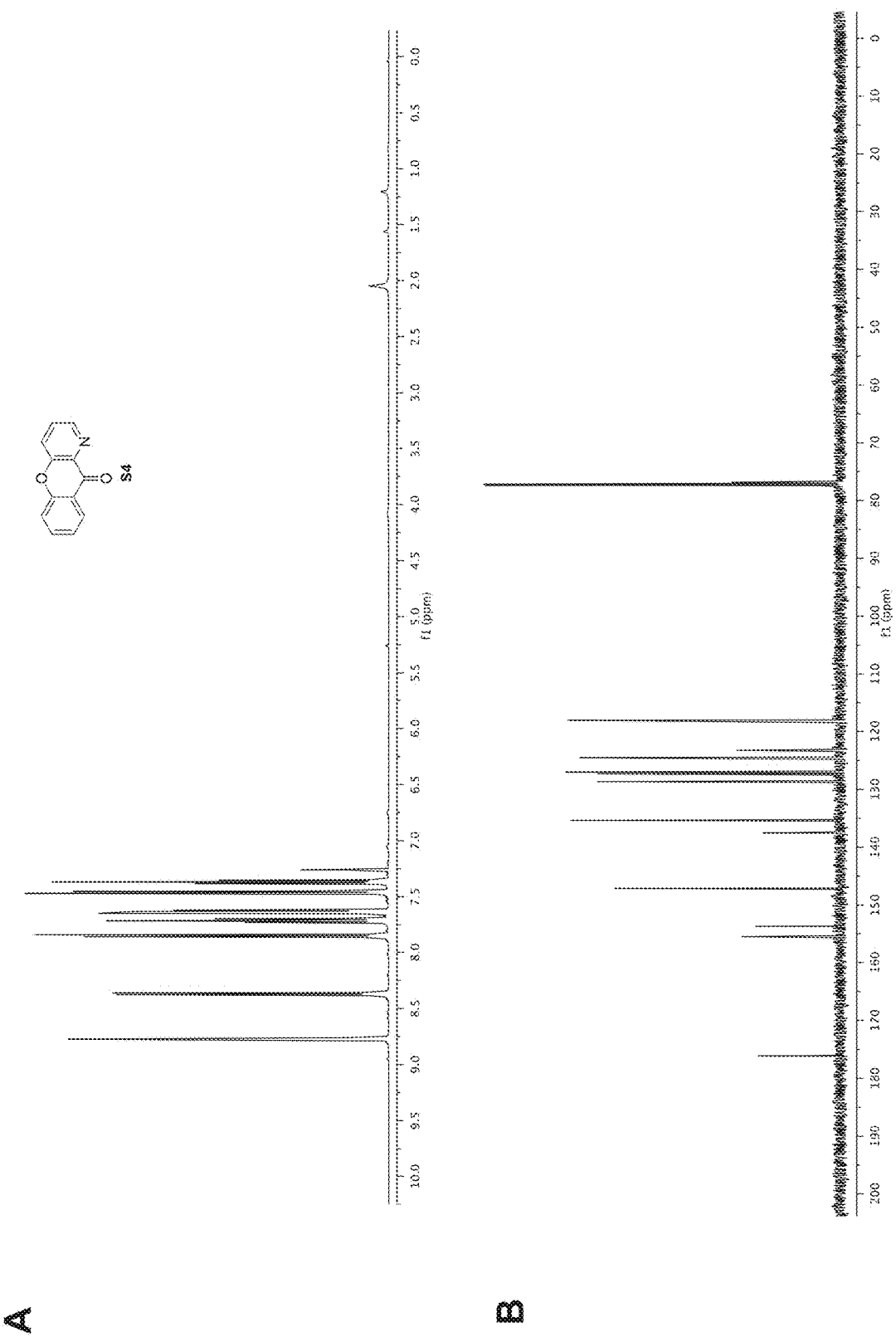
FIG. 59, comprised of FIGS. 59A-59B, depicts NMR spectral data of 1-azaxanthone S4.

To a solution of phenol (1124 mg, 11.9 mmol) in anhydrous DMF (20 mL) was added sodium hydride (60% dispersion in mineral oil, 490 mg, 12.3 mmol). After hydrogen evolution ceased, 3-chloro-2-cyanopyridine S2 (Cailly et al., 2006, Tetrahedron 62: 5862-5867) was added neat and the reaction was heated to 80° C. for 3 hours. DMF was removed under reduced pressure and the residue was dissolved in a mixture of water and DCM. The aqueous layer was extracted with DCM and the combined organic layer was washed with 2M NaOH and brine, dried with $Na_2SO_4$, filtered and concentrated in vacuo. Out of 2315 mg of the obtained crude biaryl ether S3 (Villani et al., 1975, J. Med. Chem. 18: 1-8), 1933 mg was transfer to a 250 mL beaker to carry out the ring closing reaction with 80 g polyphosphoric acid. The reaction mixture was heated in a sand bath to 260° C. for 2 hours. The reaction mixture was allowed to cool down to room temperature, poured over ice and rinsed with distilled water. The solution was neutralized with concentrated NaOH to pH 7 and extracted with DCM. The combined organic layers were washed with brine, dried with $Na_2SO_4$, filtered, and concentrated in vacuo to obtain 1-azaxanthone S4 (Villani et al., 1975, J. Med. Chem. 18: 1-8) as a white powder (1498 mg, 7.6 mmol, 84% yield after 2 steps). $^1$H NMR (500 MHz, CDCl$_3$): δ (ppm) 8.77 (2H, dd, J=4.0 Hz, 1.5 Hz), 8.37 (2H, dd, J=8.0 Hz, 1.5 Hz), 7.85 (2H, dd, J=8.5 Hz, 1.5 Hz), 7.71 (2H, td, J=7.5 Hz, 1.5 Hz), 7.63 (2H, dd, J=8.5 Hz, 4.0 Hz), 7.46 (2H, d, J=8.5 Hz), 7.37 (2H, t, J=7.5 Hz). $^{13}$C NMR (126.9 MHz, CDCl$_3$): δ (ppm) 176.1, 155.5, 153.7, 147.1, 137.5, 135.4, 128.7, 127.3, 127.0, 124.5, 123.2, 118.1. HRMS (m/z): [M+H]$^+$ calcd for $C_{12}H_8NO_2$, 198.0555; found, 198.0552. NMR spectral data for S4 can be found in FIG. 59.

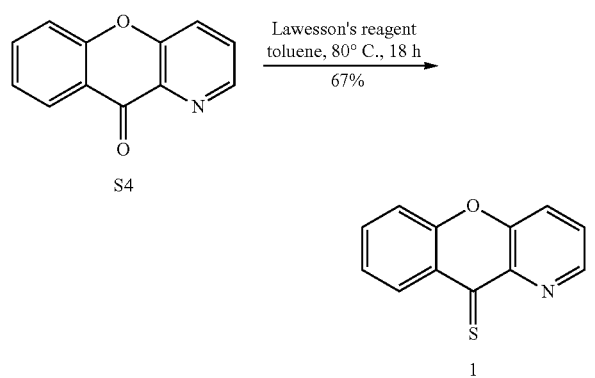

Figure 60:
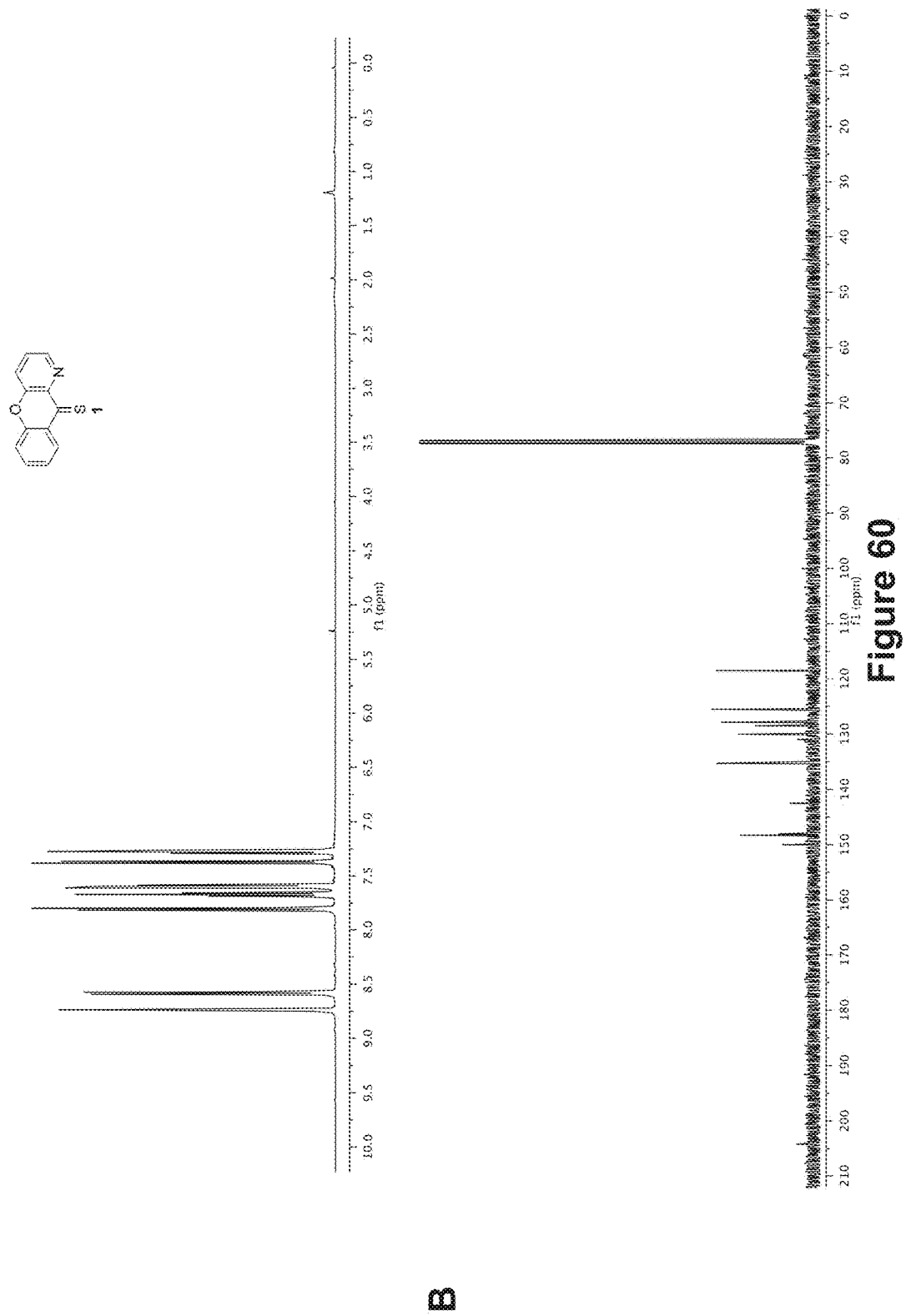
FIG. 60, comprised of FIGS. 60A-60B, depicts NMR spectral data of thioketone 1.

In a round bottom flask, 1-azaxanthone S4 (1089 mg, 5.5 mmol) and Lawesson's reagent (1167 mg, 2.9 mmol) were added and dried under high vacuum at 40° C. for 5 hours. Toluene (15 mL) was added and the reaction mixture was refluxed under argon for 1 hour. The crude mixture was concentrated under reduced pressure and purified by silica gel column chromatography using 5:95 EtOAc:DCM to give thioketone 1 as a green powder (783 mg, 3.7 mmol, 67% yield). $^1$H NMR (500 MHz, CDCl$_3$): δ (ppm) 8.74 (2H, dd, J=4.5 Hz, 1.5 Hz), 8.58 (2H, dd, J=8.5 Hz, 1.5 Hz), 7.80 (2H, dd, J=8.0 Hz, 1.5 Hz), 7.67 (2H, td, J=8.0 Hz, 1.5 Hz), 7.60 (2H, dd, J=8.5 Hz, 4.5 Hz), 7.37 (2H, d, J=8.5 Hz), 7.27 (2H, t, J=8.0 Hz). $^{13}$C NMR (126.9 MHz, CDCl$_3$): δ (ppm) 204.2, 150.0, 148.3, 148.1, 142.5, 135.3, 131.0, 130.0, 128.5, 127.9, 125.5, 118.5. HRMS (m/z): [M+H]$^+$ calcd for $C_{12}H_8NOS$, 214.0327; found, 214.0317. NMR spectral data for thioketone 1 can be found in FIG. 60.

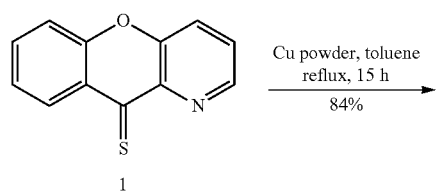

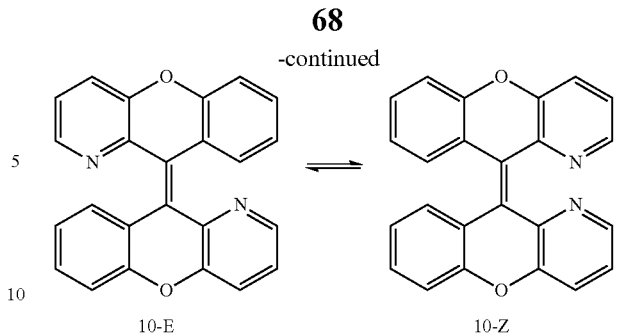

Figure 61:
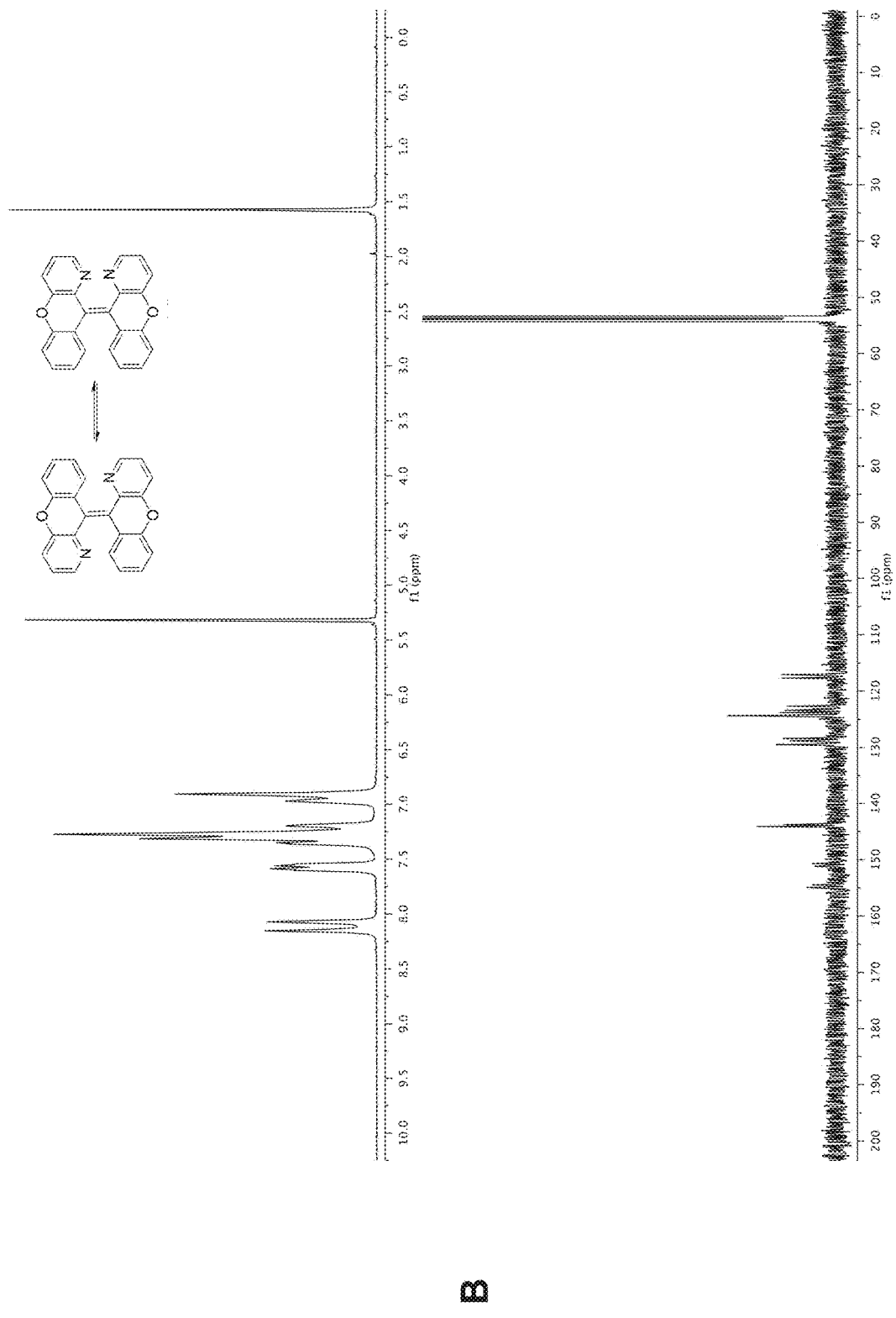
FIG. 61, comprised of FIGS. 61A-61B, depicts NMR spectral data of 10-E/10-Z.

In a 2-necked round bottom flask, copper powder (7884 mg, 124.0 mmol) and 120 ml anhydrous toluene was added. Most of the toluene was distilled off to remove any trace of water. The distillation apparatus was replaced with a condenser and purge with argon for about 15 minutes. In a separate flask, thioketone 1 (783 mg, 3.7 mmol) was dried under vacuum for 3 hours, then dissolved in 50 mL toluene and cannulated to the copper-toluene mixture. The reaction mixture was heated under reflux for 15 hours. The reaction mixture was then filtered, washed with boiling chloroform, and concentrated in vacuo. The crude mixture was purified by silica gel column chromatography using 1:9 EtOAc: DCM to obtain 10-E/10-Z as light yellow powder (557 mg, 1.5 mmol, 84% yield). $^1$H NMR (500 MHz, CD$_2$Cl$_2$): δ (ppm) 8.15 (2H, s), 8.07 (2H, s), 7.60-7.55 (4H, m), 7.36-7.20 (14H, m), 6.97-6.90 (6H, m). $^{13}$C NMR (126.9 MHz, CD$_2$Cl$_2$): δ (ppm) 154.9, 154.4, 151.2, 150.7, 144.1, 143.8, 129.6, 129.5, 128.8, 128.4, 124.5, 124.3, 123.8, 123.4, 122.7, 117.7, 117.1. HRMS (m/z): [M+H]$^+$ calcd for $C_{24}H_{15}N_2O_2$, 363.1134; found, 363.1135. NMR spectral data for 10-E/10-Z can be found in FIG. 61.

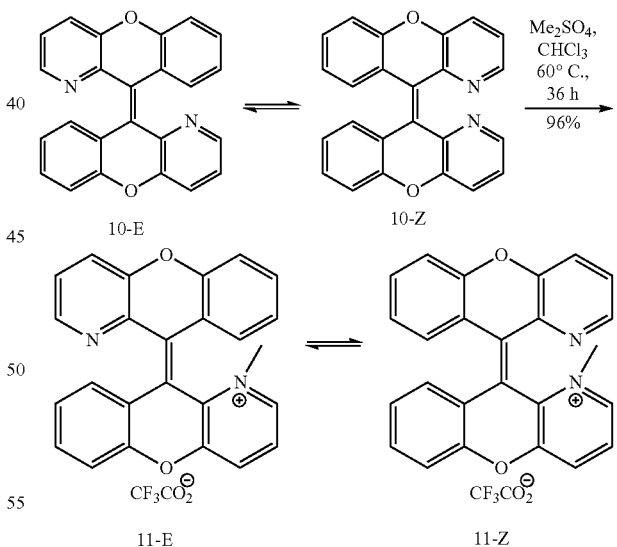

Figure 62:
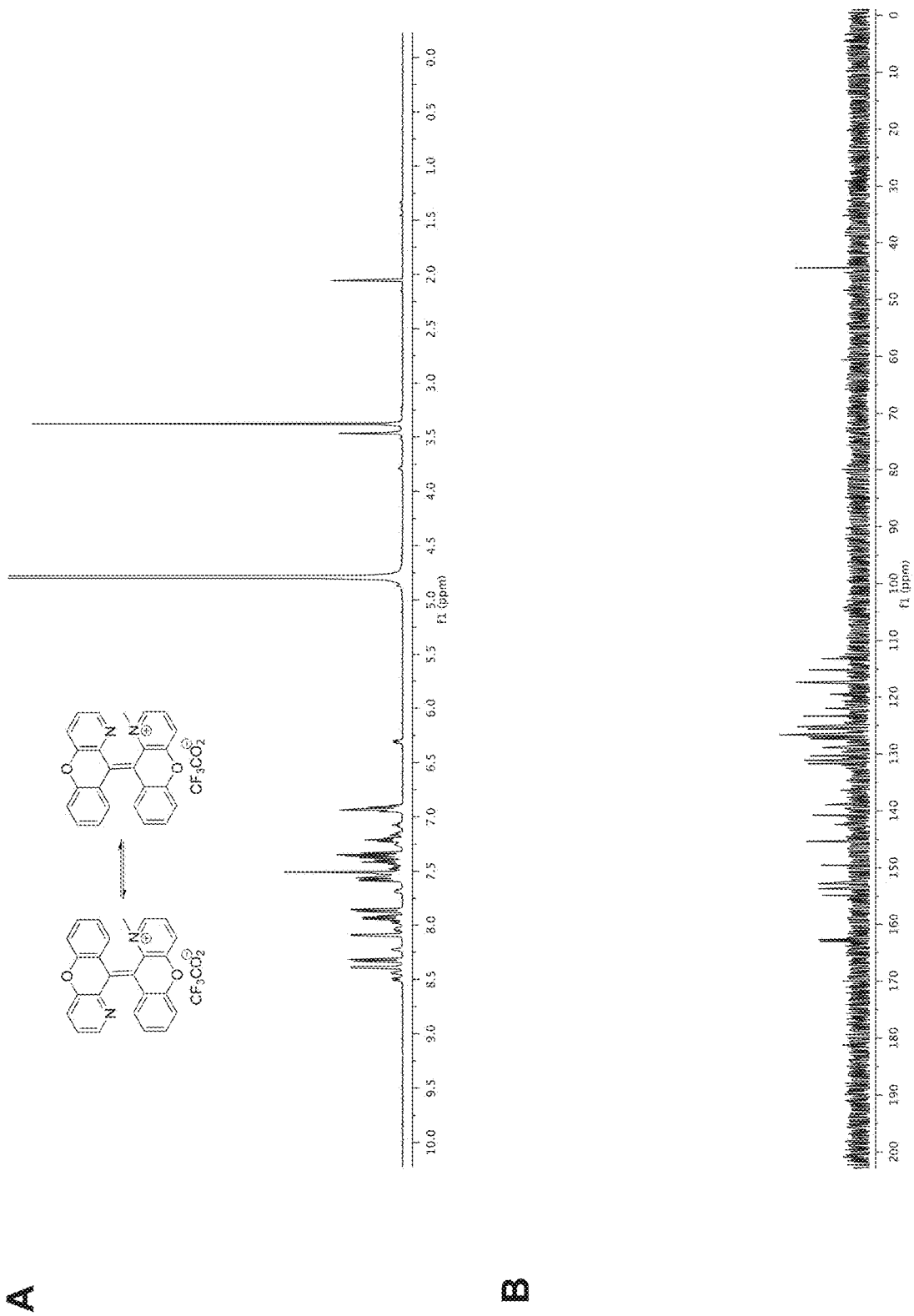
FIG. 62, comprised of FIGS. 62A-62B, depicts NMR spectral data of 11-E/11-Z.

A mixture of 10-E/10-Z (93 mg, 0.26 mmol) was dissolved in 20 mL chloroform and purged with argon for about 15 minutes. The reaction mixture was heated to 60° C. for 36 hours. Distilled water (5 mL) was added and the solution was stirred for about 2 hours. Chloroform was removed under reduced pressure and the aqueous solution was loaded on celite and purified by reversed-phase column chromatography using 0.1% TFA in water and acetonitrile as eluents. The obtained yellow powder was a 3:10 mixture of 11-E/11-Z (121 mg, 0.25 mmol, 96% yield). $^{1}$H NMR (500 MHz, D$_2$O): δ (ppm) 8.50 (0.3, d, J=8.5 Hz), 8.44 (0.3, d, J=6 Hz), 8.38 (1.0, d, J=6 Hz), 8.32 (1.0, d, J=8.5 Hz), 8.22 (0.3, d, J=4 Hz), 8.09 (1.0, dd, J=4.5 Hz, 1.0 Hz), 8.04 (0.3, dd, J=8.5 Hz, 6.5 Hz), 7.97 (0.3, d, J=9.0 Hz), 7.93 (1.0, dd, J=8.5 Hz, 6.0 Hz), 7.86 (1.0, dd, J=8.5 Hz, 1.0 Hz), 7.69 (0.3, dd, J=8.0 Hz, 5.0 Hz), 7.59-7.46 (4.2, m), 7.42 (1.0, td, J=8.0 Hz, 2.0 Hz), 7.37-7.33 (2.0, m), 7.26-7.15 (1.6, m), 7.07 (0.3, t, J=7.0 Hz), 6.95-6.90 (2.0, m), 6.31 (0.3, d, J=7.5 Hz), 3.46 (0.9, s), 3.37 (3.0, s). $^{13}$C NMR (126.9 MHz, D$_2$O): δ (ppm) 154.8, 153.7, 153.6, 152.8, 149.5, 145.4, 142.4, 140.7, 138.9, 131.7, 131.1, 130.3, 128.9, 127.3, 127.0, 126.6, 125.6, 125.2, 123.4, 122.0, 119.5, 117.5, 117.3, 113.2, 44.5; CF$_3$COO$^-$: 162.9 (m), 116.3 (m). HRMS (m/z): [M]$^+$ calcd for C$_{25}$H$_{17}$N$_2$O$_2$, 377.1290; found, 377.1290. Extinction coefficient Φ=11040 M$^{-1}$cm$^{-1}$ (solvent: water). Quantum yield Φ=0.021 (solvent: water, standard: coumarine 153 in ethanol). NMR spectral data for 11-E/11-Z can be found in FIG. 62.

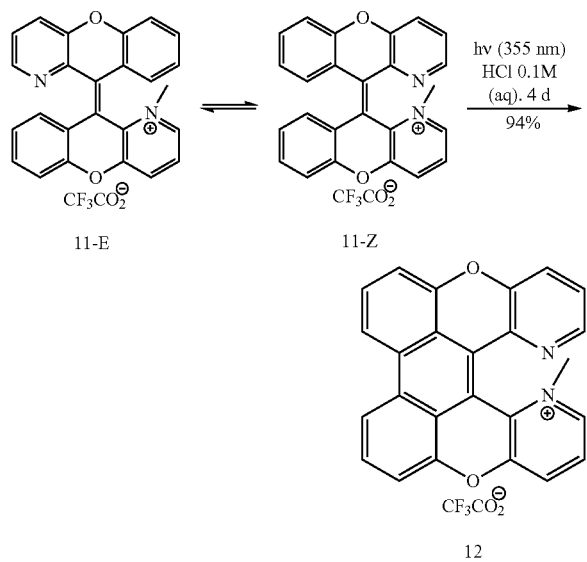

Figure 63:
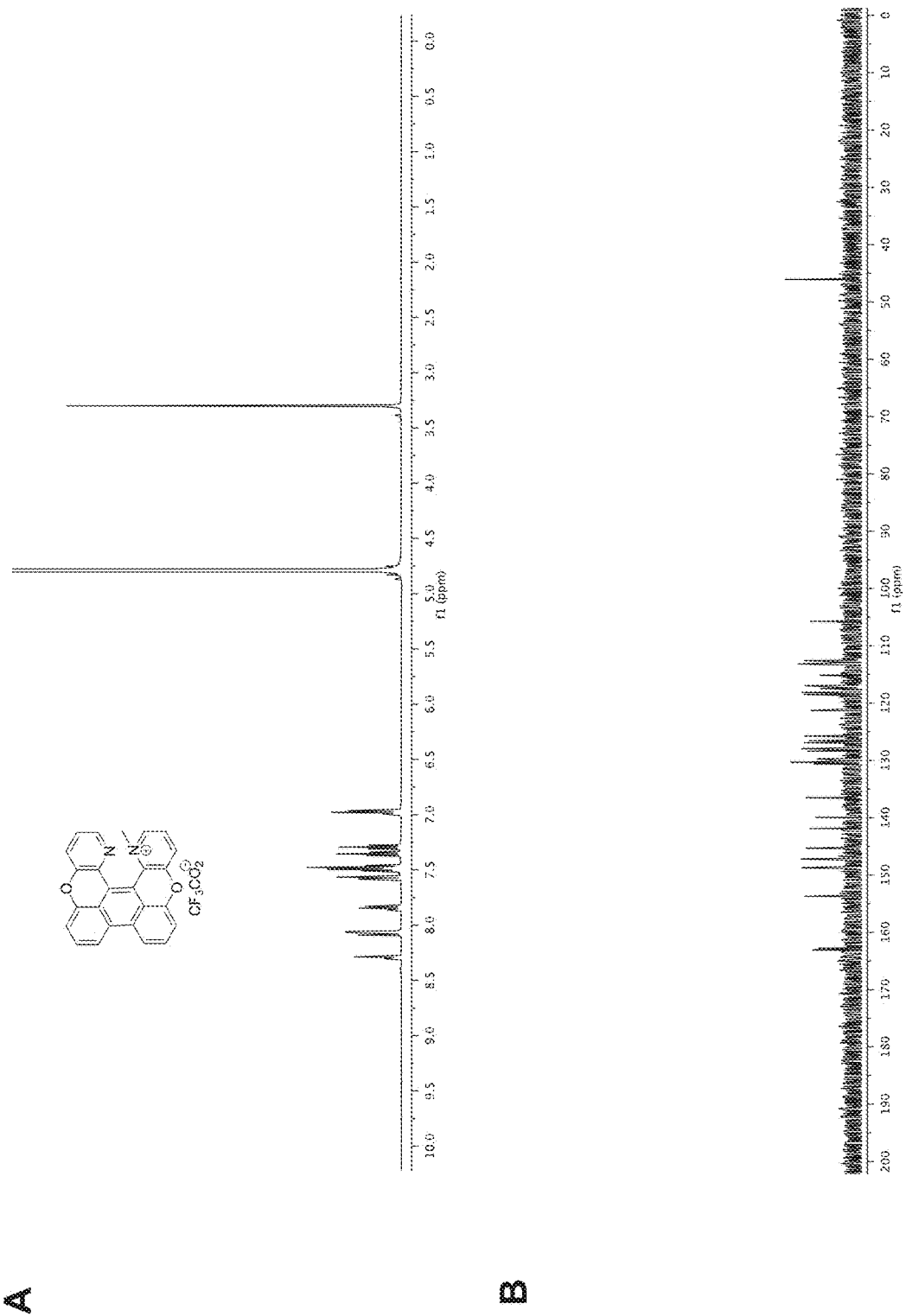
FIG. 63, comprised of FIGS. 63A-63B, depicts NMR spectral data of 12.

A solution of 11-E/11-Z (5.2 mg, 0.011 mmol) in 20 mL HCl 0.1M was injected into a teflon tube, which was wrapped around a graduated cylinder, to increase surface area. The teflon tube was held in place by transparent tape and copper wire. The two ends were clamped together using a Hoffmann clip. The reaction was taken place in a photoreactor using 355 nm lamp. After 4 days, solvent was evaporated under reduced pressure. The crude mixture was purified using reversed-phase column chromatography using 0.1% TFA in water and acetonitrile, giving 12 as a red solid (4.9 mg, 0.010 mmol, 94% yield). $^{1}$H NMR (500 MHz, D$_2$O): δ (ppm) 8.29 (1H, d, J=6.0 Hz), 8.09-8.06 (2H, m), 7.85 (1H, dd, J=8.5 Hz, 6.0 Hz), 7.57 (1H, dd, J=8.0 Hz, 1.5 Hz), 7.51-7.46 (3H, m), 7.36 (1H, t, J=8.0 Hz), 7.29 (1H, t, J=8.0 Hz), 6.98 (2H, t, J=6.5 Hz), 3.30 (1H, s). $^{13}$C NMR (126.9 MHz, D$_2$O): δ (ppm) 153.7, 148.7, 148.7, 147.2, 145.4, 141.9, 140.0, 136.5, 130.6, 130.3, 129.7, 128.4, 128.3, 128.0, 126.9, 126.5, 125.8, 121.3, 118.5, 118.1, 117.0, 113.2, 112.6, 105.7, 46.1; CF$_3$COO$^-$: 163.0 (m), 116.3 (m). HRMS (m/z): [M]$^+$ calcd for C$_{25}$H$_{17}$N$_2$O$_2$, 377.1290; found, 377.1290. Extinction coefficient Φ=11496 M$^{-1}$cm$^{-1}$ (solvent: water). Quantum yield Φ=0.100 in (solvent: water, standard: fluorescein in NaOH 0.1 M). NMR spectral data for 12 can be found in FIG. 63.

Cell Imaging

For live cell imaging, HeLa cells and HeLa cells expressing a mitochondrial outer membrane targeting domain from Listeria monocytogenes (ActA, C-terminal 47 amino acids) fused to a HaloTag-GFP construct (Ballister et al., 2014, Nat. Commun. 5: 4575) were used. Cells were cultured in a 60 mm culture dish using Life Technologies Dulbecco's Modified Eagle Medium (DMEM) media with phenol red, 10% Fetal Bovine Serum and 1% penicillin-streptomycin at 37° C. in a humidified atmosphere with 5% CO$_2$. The cells were detached with 0.05% trypsin-EDTA and transferred to a 35 mm glass bottom poly-D-lysine coated dish 2-5 days before imaging with about 2 mL of the above-mentioned media. A 5 mM solution of 11-E/11-Z in MiliQ water and a 1 mM solution of MitoTracker Red FM in DMSO were prepared. Two microliter of each solution was mixed with 2 mL new media and added to the cells after the old media was removed. After incubation (3 hours to overnight for 11-E/11-Z and 1 hour for MitoTracker Red FM), the excess dyes were washed twice with non-phenol red DMEM before imaging. The cells were kept in 2 mL non-phenol red DMEM during imaging.

A Leica TCS SP8 confocal microscope equipped with a 63×/1.4 NA oil immersion objective lens was used in FIG. 2A, 3E, S2, S3, and S4. To selectively observe 11-E/11-Z, the excitation wavelength of 405 nm and the emission wavelength range of 620-650 were used. To selectively observe MitoTracker Red FM, the excitation wavelength of 638 nm and the emission wavelength range of 650-700 were used. To selectively observe GFP, the excitation wavelength of 488 nm and the emission wavelength range of 500-550 were used.

A Leica DM4000 spinning disk confocal microscope equipped with a 100×1.4 NA oil immersion objective was used in FIGS. 3A and 3B. In FIG. 3A, two channels were used. The first channel has 444 nm excitation wavelength and 525 nm emission wavelength (emission bandpass filter, bandwidth=36 nm). The second channel has 488 nm excitation wavelength and 632 nm emission wavelength (emission bandpass filter, bandwidth=60 nm). The two channels were used alternatingly to carry out 200 150-ms pulses. In FIG. 46B, selective activation was carried out by short pulse (about 1 second) using a 405 nm laser (CrystaLaser, DL405-050-O) controlled by the iLas2 module in Metamorph. All image processing was done using ImageJ. All curve fitting was done using Prism.

Cytotoxicity Studies

In a 96-well plate, HeLa cells were plated at 5,000 cells/well in culture media as described above (50 μL/well) and incubated at 37° C. in a humidified atmosphere with 5% CO$_2$. After 24 hours, cells were treated with 11-E/11-Z (final concentration was 5 μM), MitoTracker Red FM (final concentration was 1 μM), and DMSO (vehicle control for MitoTracker). For wells treated with MitoTracker and DMSO, DMSO concentration was kept at 1%. Untreated cells were used as vehicle control for 11-E/11-Z. Final volumes were 100 μL/well. Cells were incubated at 37° C. in 5% CO$_2$ for 24, 48, or 72 hours. Alamar Blue (10 μL) was added 2 hours prior to fluorescence measurement. Fluorescence was measured at 560 nm excitation and 590 nm emission. Vehicle control was taken as 100% cell viability.

Figure 43:
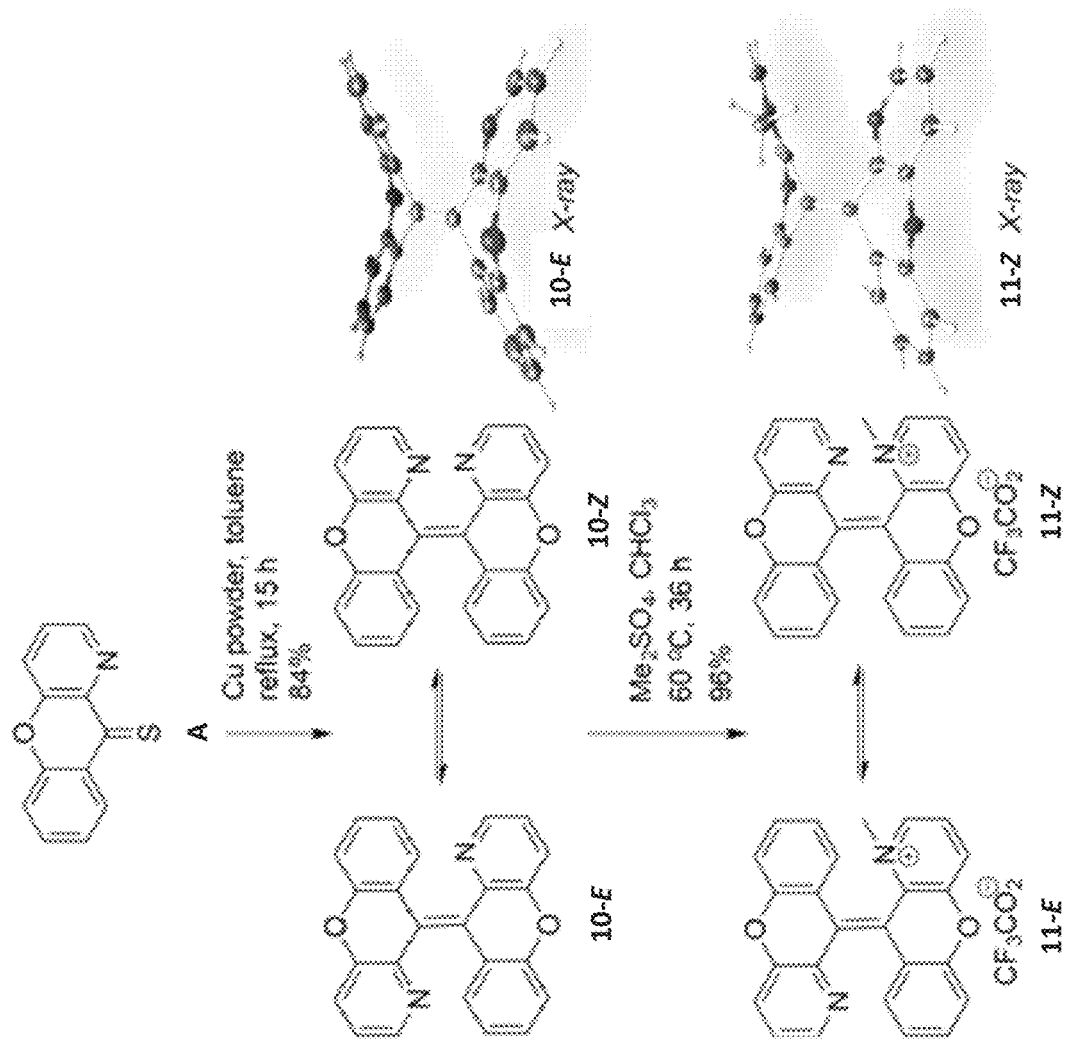
FIG. 43 is an exemplary synthetic scheme of 11-E/11-Z and the crystal structures of 10-E and 11-Z.
Figure 52:
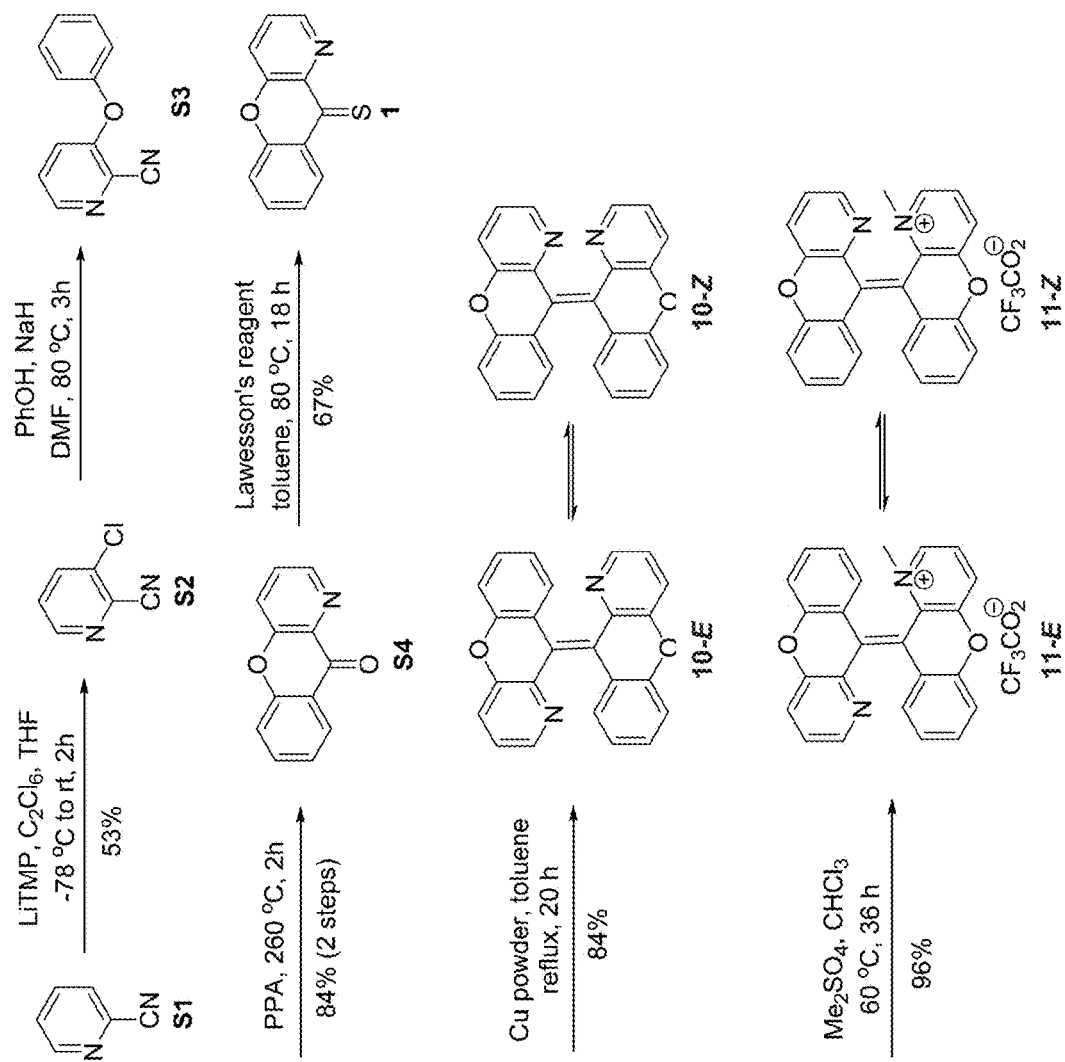
FIG. 52 is an exemplary synthetic scheme of the preparation of compounds 11-E/11-Z.
Figure 53:
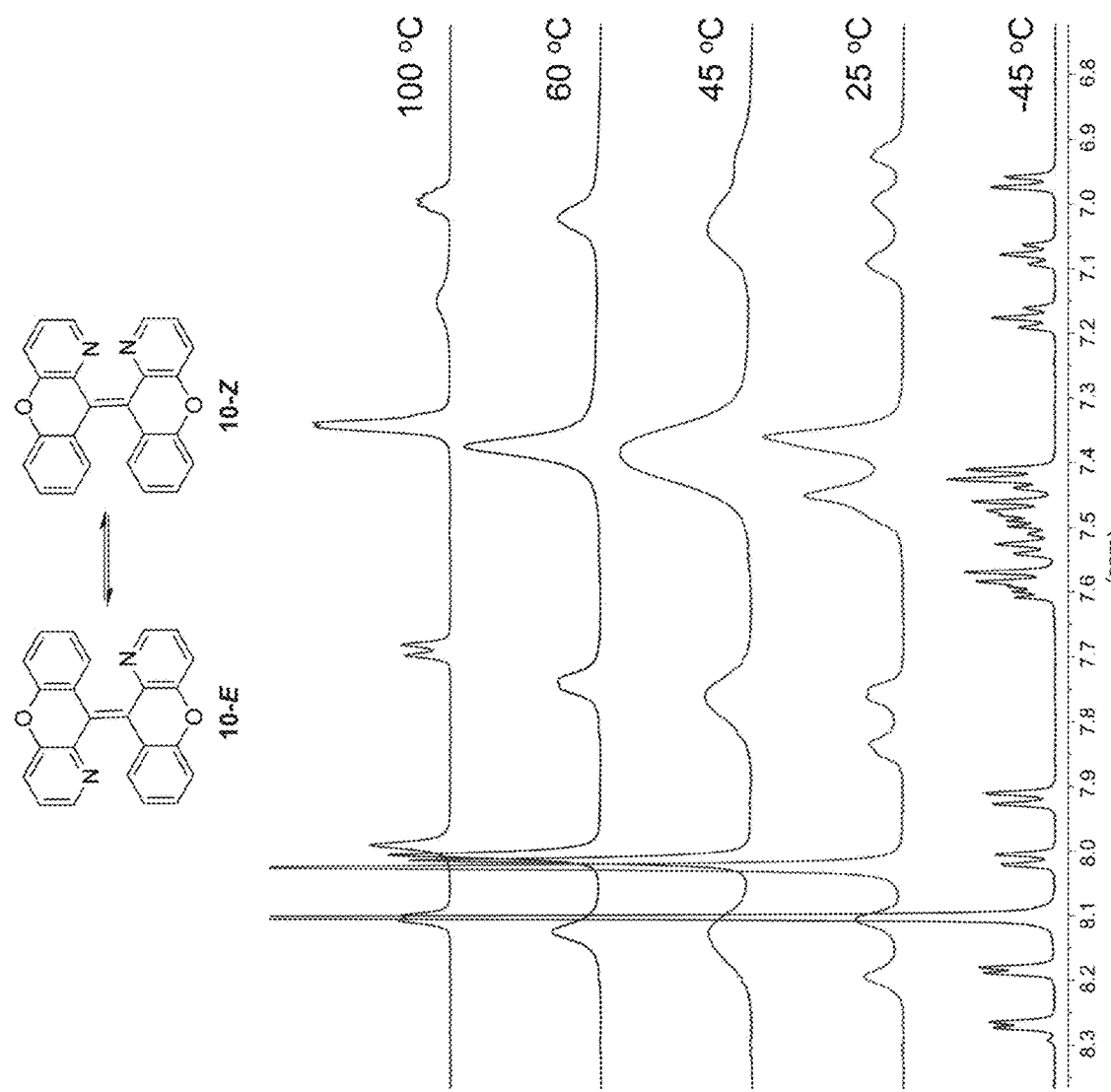
FIG. 53 is a variable temperature $^1$H-NMR of 10-E/10-Z in DMF-d$_7$.

Results:

A rapid and efficient synthesis of the desired photoactivatable probe starting with commercially available 2-cyanopyridine (FIG. 52). 2-cyanopyridine was elaborated to thioketone A using methods similar to those previously reported (Rarig et al., 2013, J. Am. Chem. Soc. 135: 9213-9219, which is incorporated by reference in its entirety for all purposes). Homocoupling of A, using copper powder in toluene under refluxing conditions, yielded 1,1'-diazaxanthilidene 10 as an interconverting mixture of E and Z isomers in 84% yield (FIG. 43). Methylation of 10 with dimethyl sulfate afforded the desired monomethylated product 11-E/11-Z in 96% yield. The overall yield of the probe from commercial starting materials after 6 steps was 24% (FIGS. 43 and 52). Single crystals of 10-E and 11-Z were obtained by slow evaporation from chloroform:methanol (1:1) and water, respectively. Both structures revealed anti-folded conformations despite the increased steric influence of methylation in 11-Z (FIG. 43). Variable temperature $^1$H-NMR (J. Sandström, 1982, Dynamic NMR spectroscopy, Academic Press, London, New York) of 10-E/10-Z in deuterated N,N-dimethylformamide confirmed the dynamic interconversion of the E and Z isomers at room temperature. At low temperature, separate sets of sharp and well-resolved signals were observed for the E and Z isomers of 11. Incremental heating resulted in significant signal broadening followed by sharpening and resolved coupling at high temperature. This result indicated rapid exchange. Coalescence was observed at 45° C., and the activation energy was determined to be $\Delta G^{\ddagger}=15.7$ kcal/mol (FIG. 52).

Figure 44:
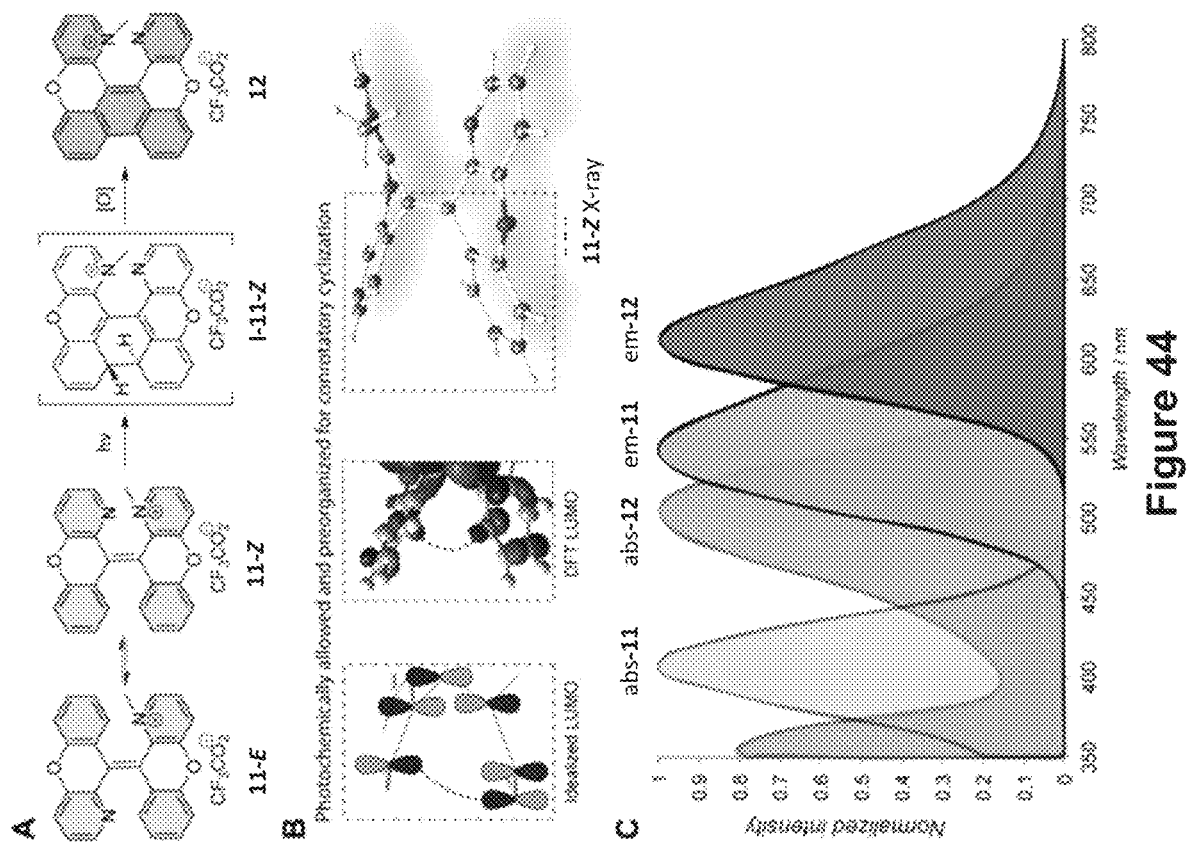
FIG. 44, comprised of FIGS. 44A-44C, depicts synthetic and experimental data of compounds 11-E/11-Z and 12.

Upon irradiation at 365 nm using a Rayonet photoreactor, the 11-E/11-Z mixture was found to undergo photocyclization, followed by oxidation to yield photoproduct 12 (FIG. 44). To promote the photocyclization step of 11-E/11-Z, both the anti-folded conformation and dynamic interconversion are crucial. According to Woodward-Hoffmann rules, electrocyclization of the 1,3,5-hexatriene moiety of 3-Z (4n+2 electron system) is thermally allowed in a disrotatory manner and photochemically allowed in a conrotatory manner (Anslyn and Dogherty, 2006, Modern physical organic chemistry, University Science, Sausalito, Calif.; Fleming, 2009, Molecular Orbitals and Organic Chemical Reactions, John Wiley & Sons Canada). The anti-folded conformation of 11-Z is preorganized for conrotatory cyclization, satisfying the requirement for photochemical reaction. This conclusion was further confirmed by TD-DFT calculation of 11-Z using previously described methods (Frisch et al., 2010, Gaussian 09, Revision B.01 ed., Gaussian, Inc., Wallingford, Conn.). Conrotatory cyclization of the LUMO led to constructive interaction (photochemically favored) (FIG. 44B). The structure of 11-E did not permit such cyclization but E-Z isomerization allowed 11-Z to be produced, promoting photoreaction. As a result, the dihydrophenanthrene intermediate was attained, followed by oxidation to give photoproduct 12. The dihydrophenanthrene intermediate was not isolable from the reaction mixture.

Compound 11-E/11-Z was found to be emissive with a large Stokes shift (135 nm). Photoproduct 12 is red-shifted in both absorbance and emission by approximately 100 nm while retaining a large Stokes shift of 108 nm (FIG. 44C). Live cell imaging studies of 11-E/11-Z were performed in HeLa cells, resulting in remarkably specific subcellular localization, consistent with mitochondrial uptake. An engineered HeLa cell line expressing GFP labeled proteins specifically localized to the outer mitochondria membrane (mito-GFP cell line) (Ballister et al., 2014, Nat. Comm. 5: 5475) was used as controls to confirm mitochondrial localization for 11-E/11-Z in this report. The localization statistics were also compared to that of a commonly used and commercially available MitoTracker dye (Johnson, 2010, Molecular probes handbook: a guide to fluorescent probes and labeling technologies, 11$^{th}$ ed., Life Technologies Corp., USA). The control cell line consisted of a population of HeLa cells expressing a GFP-fusion protein localized specifically to the outer mitochondrial membrane (mito-GFP cell line) in addition to a population of non-GFP expressing HeLa cells, which serve as an internal control for compound localization in the absence of GFP signal. Two channels 405/635 and 488/525 were used to detect 11-E/11-Z and GFP, respectively, with no bleed-though observed. All images were kept at the same brightness and contrast settings.

Figure 45:
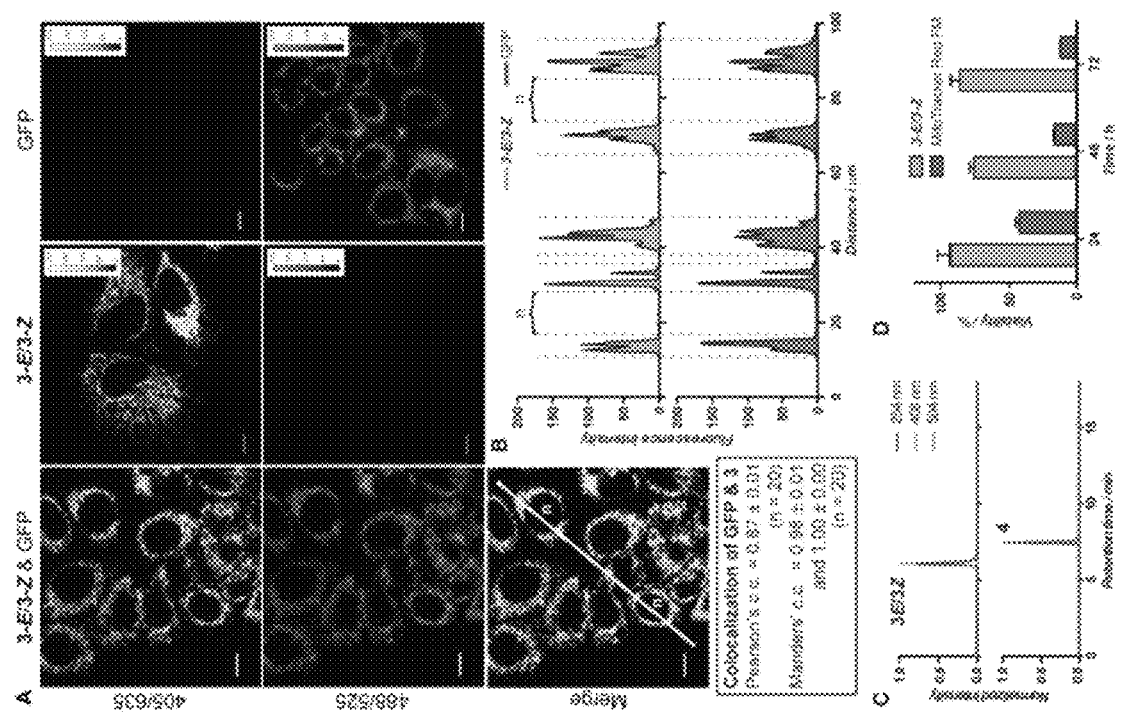
FIG. 45, comprised of FIGS. 45A-45D, depicts experimental imaging data of 11-E/11-Z.
Figure 54:
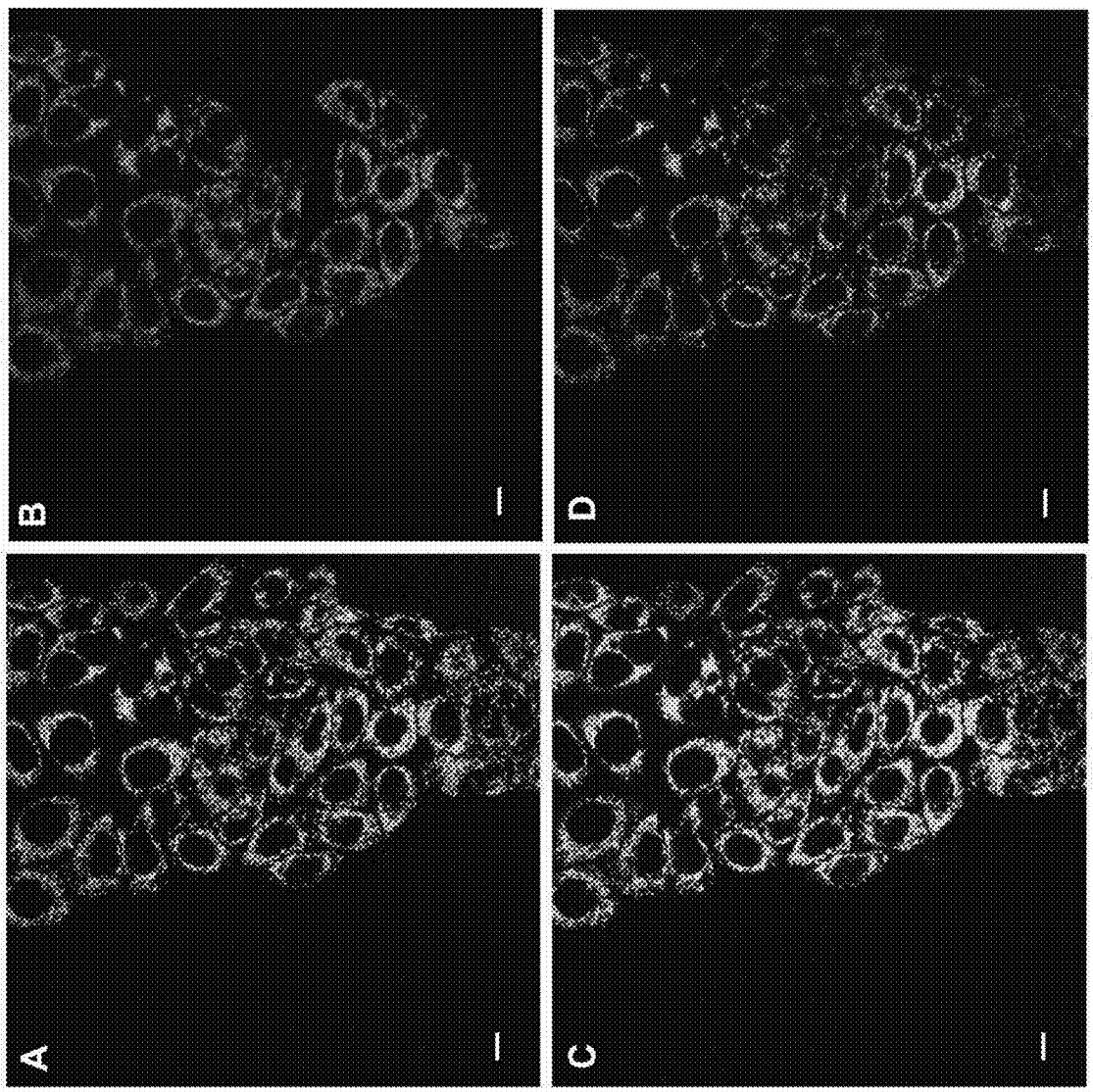
FIG. 54, comprised of FIGS. 54A-54D, depicts a series of confocal images of mixed HeLa and mito-GFP cells stained with 11-E/11-Z.

Incubating mito-GFP cells with 11-E/11-Z allowed colocalization to be assessed (FIGS. 45A and 54). Colocalization statistics were calculated for 80 cells over multiple frames showed significant overlap (Pearson's coefficient: 0.81±0.02; Manders coefficients: 0.98±0.01 and 1.00±0.00; Spearman correlation: 0.88±0.02). High Manders coefficients point to near exclusive mitochondrial localization of 11-E/11-Z in GFP positive cells.

Figure 55:
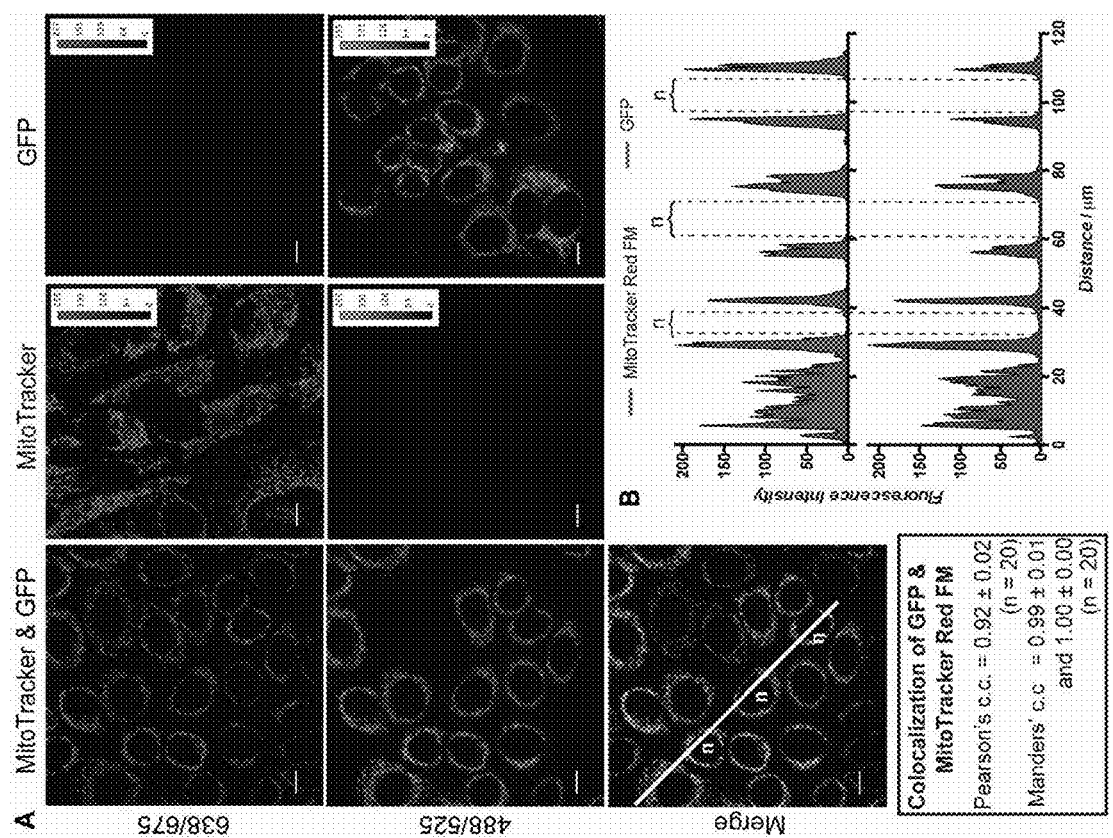
FIG. 55, comprised of FIGS. 55A-55B, depicts experimental data of colocalization studies.
Figure 56:
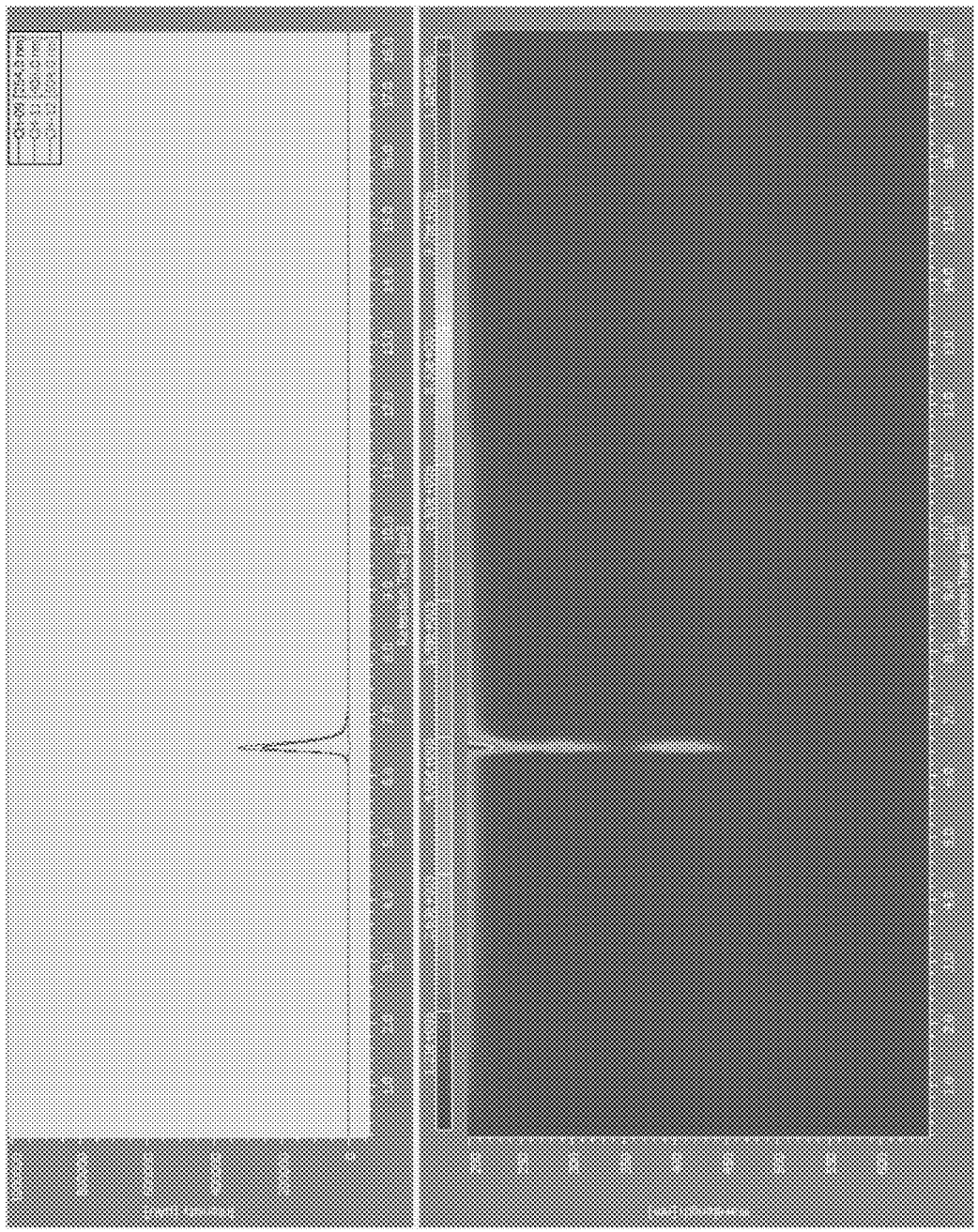
FIG. 56 is an HPLC chromatogram of 11-E/11-Z.

Variation in intensity between localized 11-E/11-Z and GFP resulted in a slightly lower Pearson's coefficient. Although not wishing to be bound by any particular theory, this small deviation may be attributed to the difference between internal mitochondrial localization of 11-E/11-Z versus external mitochondrial membrane localization of GFP. Intensity profiles across multiple cells are shown in FIG. 45A. Additional colocalization studies were carried out using commercially available Mitotracker Red (Johnson, 2010, Molecular probes handbook: a guide to fluorescent probes and labeling technologies, 11$^{th}$ ed., Life Technologies Corp., USA) and similar results were observed when comparing colocalization to GFP labeled mitochondria (FIGS. 55-56). High signal to noise was observed in the intensity line plots for both GFP and 11-E/11-Z (FIG. 45B).

Figure 57:
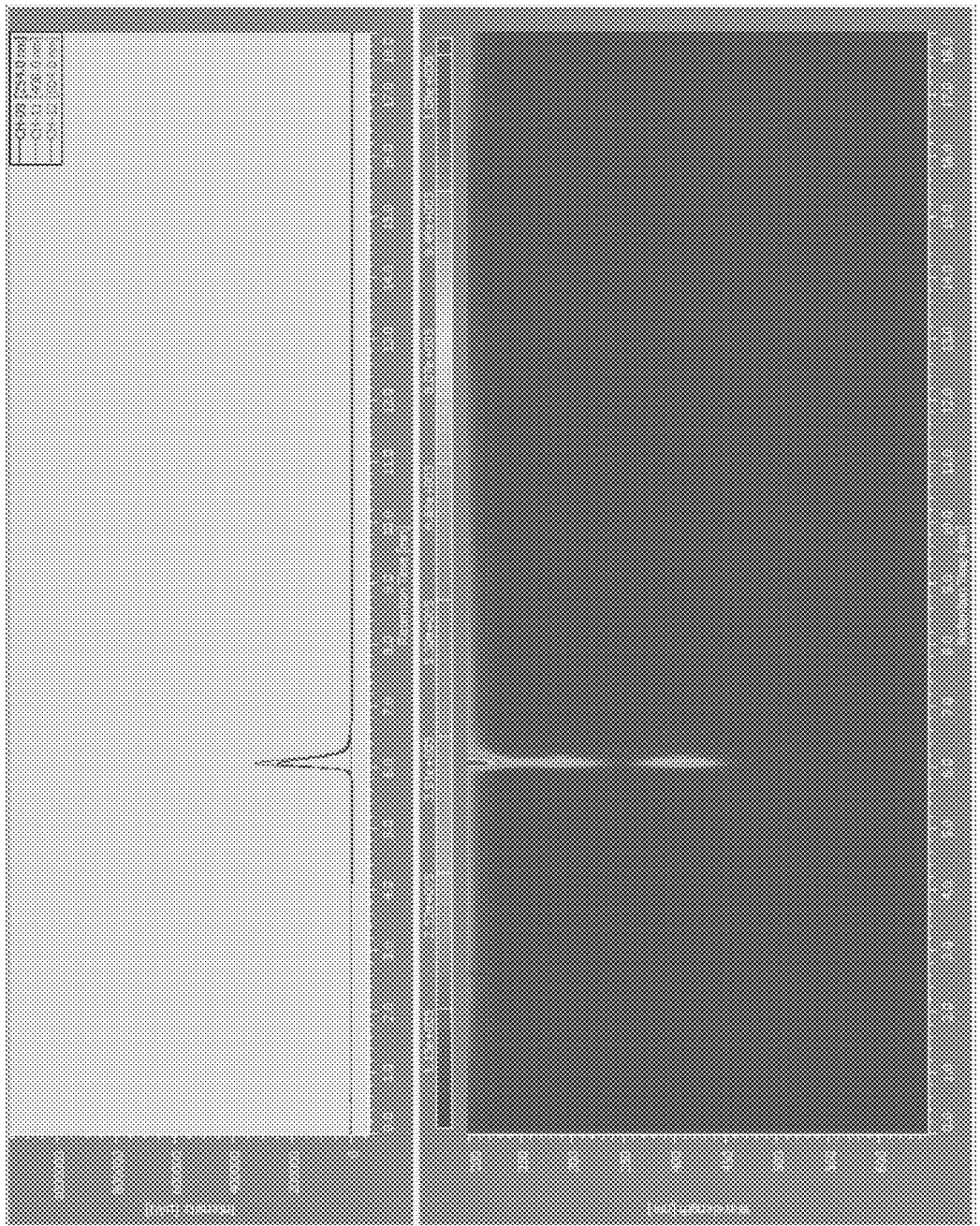
FIG. 57 is an HPLC chromatogram of a 1M aqueous solution of 11-E/11-Z after 10 days under ambient light.
Figure 58:
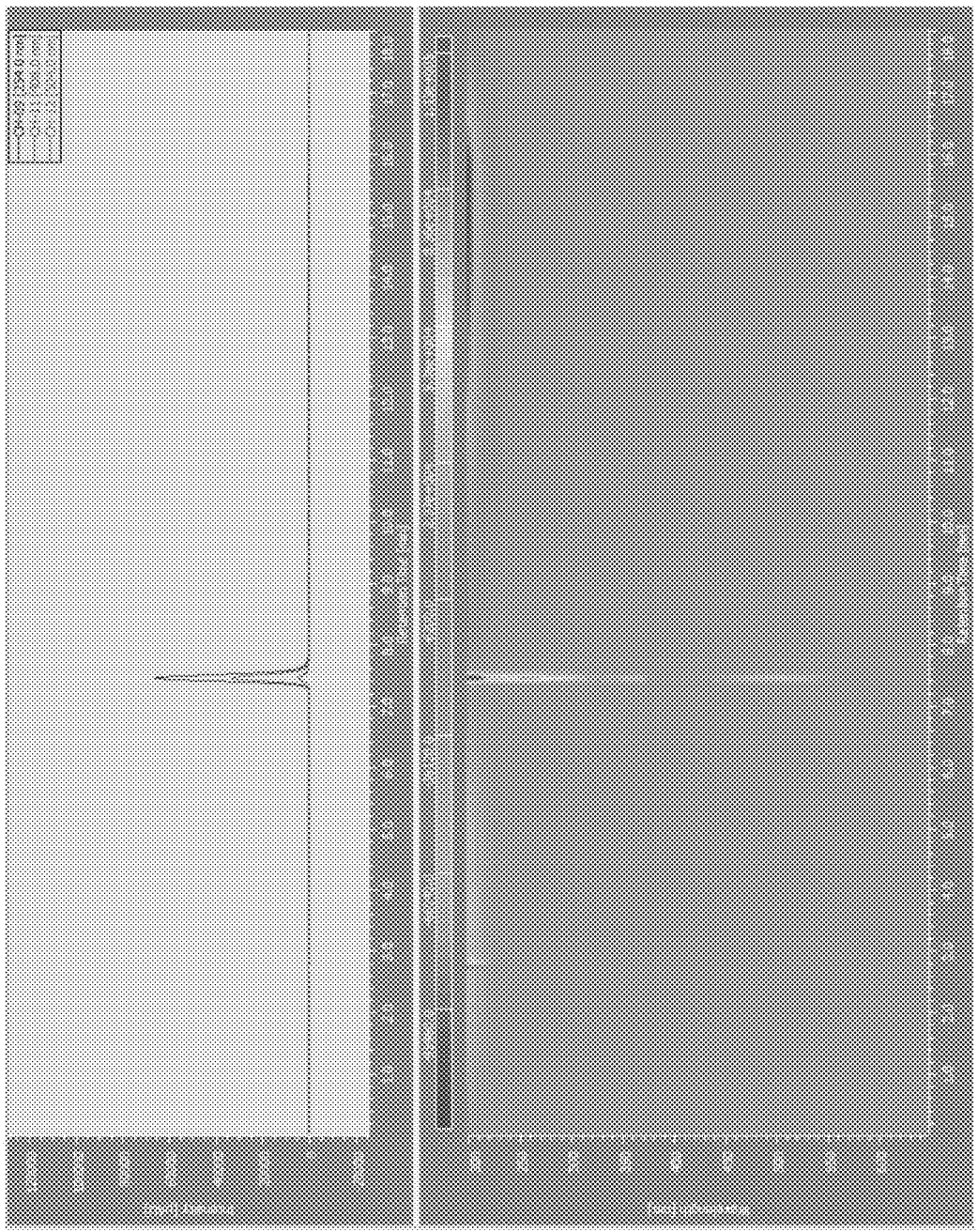
FIG. 58 is an HPLC chromatogram of 12.

The stability of 1 mM aqueous solution of 11-E/11-Z was assessed under ambient light conditions at 25° C. for 10 days. HPLC analysis of the resulting solution revealed no evidence for decomposition or photoconversion compared to a standard sample of photoproduct 12 (FIG. 45C). Cytotoxicity studies on HeLa cells over 24, 48, and 72 hours confirmed that 11-E/11-Z had very low cytotoxicity. For comparison, MitoTracker Red FM, one of the most commonly used mitochondria imaging probes, showed significant cytotoxicity over the same time course with a 5 fold lower concentration (FIG. 45D). HPLC chromatograms of compounds 11-E/11-Z and 12 can be seen in FIGS. 57 and 58.

Figure 46:
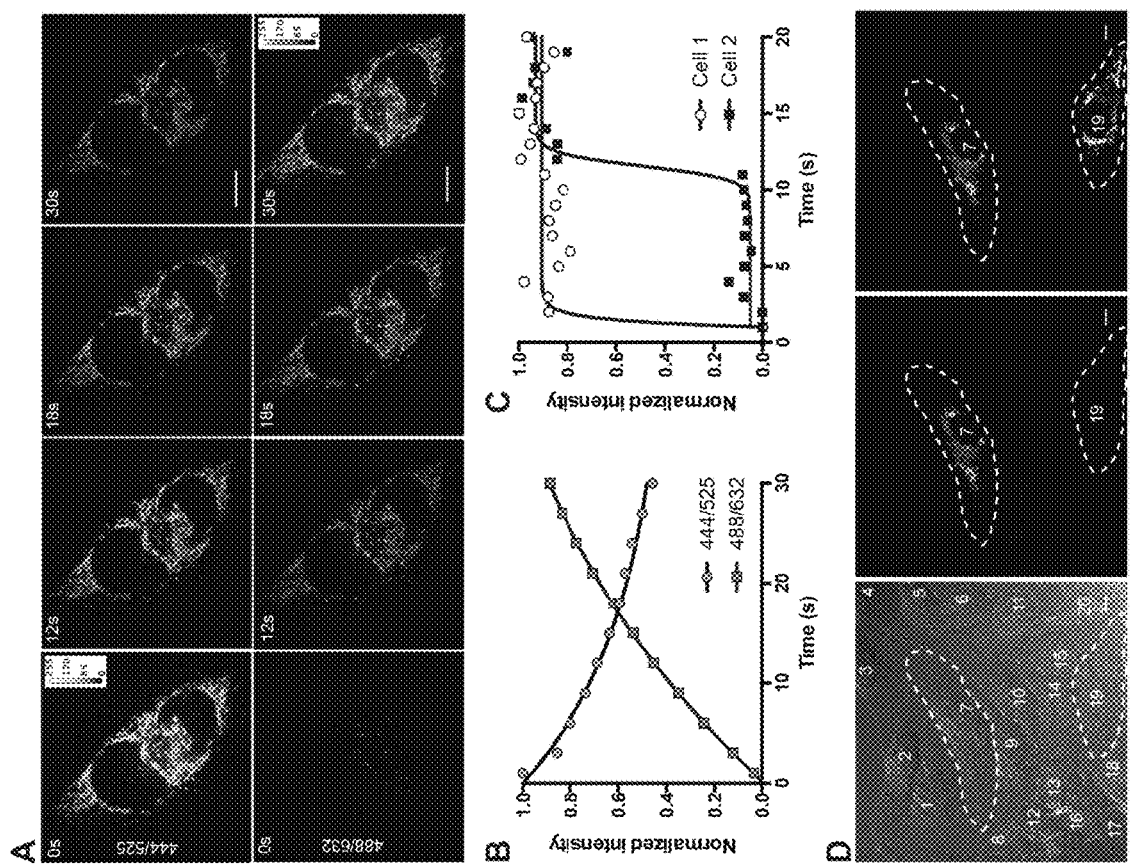
FIG. 46, comprised of FIGS. 46A-46D, depicts experimental imaging data of 11-E/11-Z.

By combining the observed photoreaction (FIG. 44A) and the ability to selectively label mitochondria for live cell imaging (FIG. 45A), intracellular photoactivation of 11-E/11-Z was attempted. The roughly 100 nm red-shifted absorbance and emission spectra of 12 compared to 11-E/11-Z allowed for selective excitation of individual species. Alternating use of the two channels (i.e., 444/525 (for 11-E/11-Z) and 488/632 (for 12)) resulted in photoconversion of 11-E/11-Z to 12 in live cells (FIG. 46). A significant increase in the intensity of 4 was achieved after 30 seconds, using 200 total scans (FIG. 46A, 46B). To investigate the spatial selectivity, a targeted 405 nm laser (CrystaLaser, DL405-050-O) was used to target smaller areas of the cells. Confocal images were captured using a 488 nm excitation laser and a 632 nm emission filter. Immediately after the first activation, a bright signal was detected at the targeted region (box 1). The tubular morphology of the mitochondria was observed. The remaining portions of the mitochondria remained dim for an additional 10 seconds using the 488 nm excitation laser.

These results also demonstrate that individual cells can be photoactivated in extremely crowded environments where cells are confluent. A standard 405 nm FRAP laser was used for sequential activation with excellent spatial control over individual cells in crowded environments (FIG. 46D). Using 50 20-second pulses, the mitochondrial probe 11 was photoconverted to 12. Two individual cells out of 20 cells were activated (cell 7 and cell 19, FIG. 46D).

Example 4

2,2'-Diazaxanthylidene: A Bis-Tricyclic Heteroaromatic Ene Scaffold for Bioimaging Fluorophores The results described herein demonstrate that the bistricyclic aromatic ene (BAE) 2,2'-diazaxanthylidene serves as a useful template for discovering photo-resistant cell-permeable fluorophores with subcellular specificities for mitochondria. Bathochromatic emission and excitation shifts are achieved upon photocyclization/oxidation of aromatic rings due to conformational change. Mitochondria-specific stains with great quantum yield and resistance to photobleaching were also identified.

Figure 48:
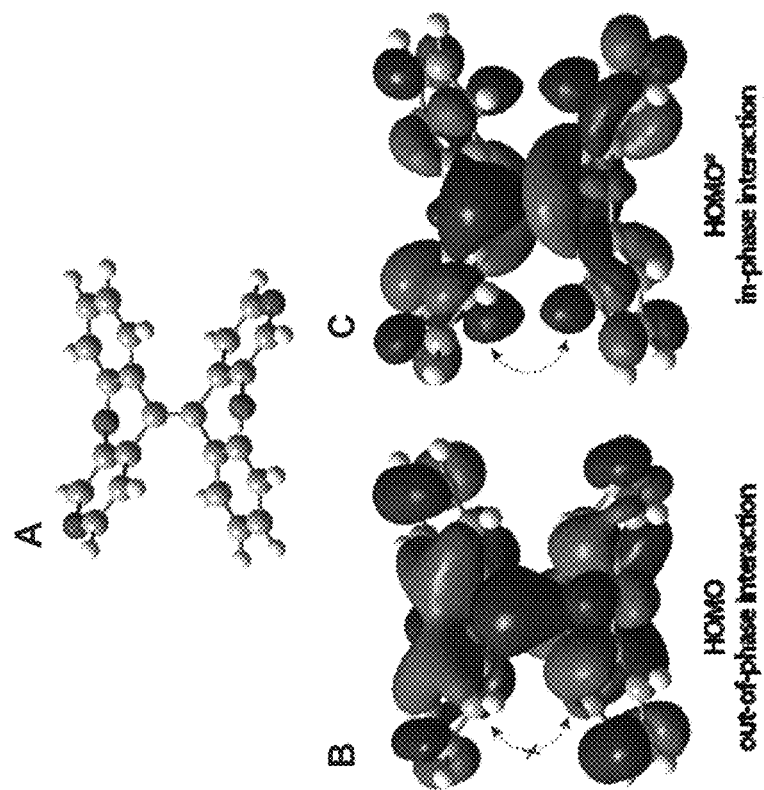
FIG. 48, comprised of FIGS. 48A-48C, depicts modeled structures demonstrating that the electrocyclization of E-1 was facilitated by anti-folded conformation.
Figure 47:
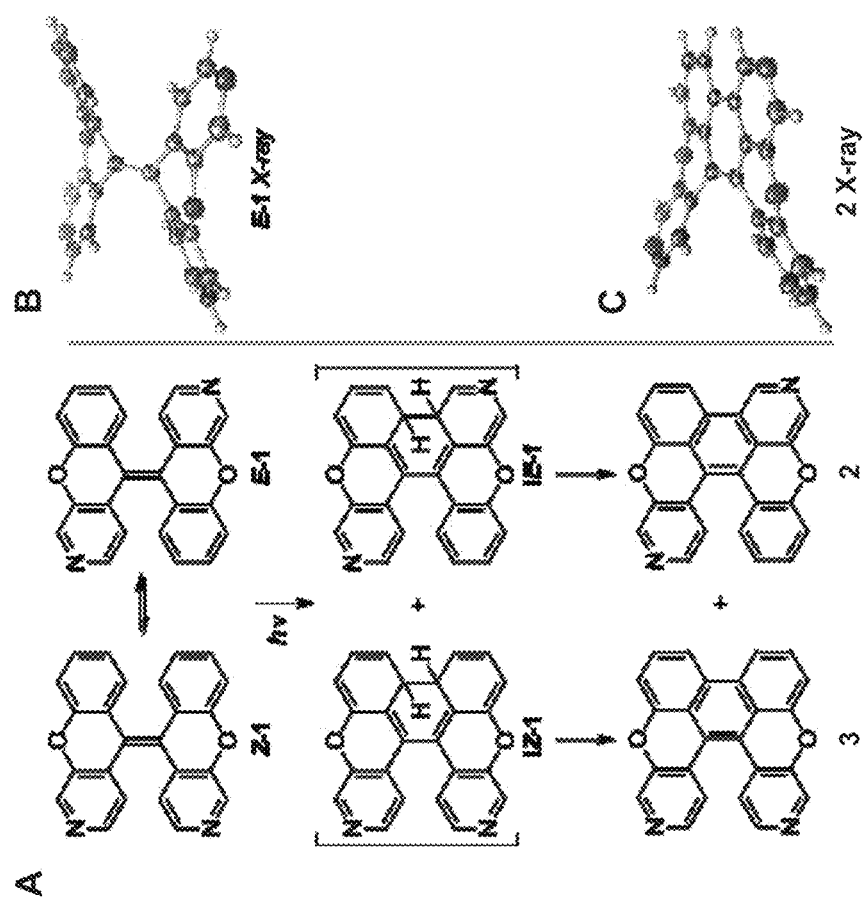
FIG. 47, comprised of FIGS. 47A-47C, depicts synthetic and physical data of compounds 2 and 3.

Upon being exposed to direct sunlight, 2,2'-diazaxanthilidene E-1/Z-1 underwent photoreaction to form photoproducts 2 and 3 (FIG. 47). The yield was significantly improved when the reaction was carried out in a Rayonet photoreactor with the addition of iodine and methyloxirane. A 32:68 mixture of 2:3 was obtained in 74% yield (FIG. 47). Although not wishing to be bound by any particular theory, this result suggests that 2 comes from Z-1 and 3 from E-1 via electrocyclization/oxidation. Neither of the dihydrophenanthrene intermediates IZ-1 nor IE-1 were isolable from the reaction mixture. Photoreaction of E-1/Z-1 was facilitated by the anti-folded conformation, which aligned the reactive moieties nicely for a constructive in-phase interaction of the HOMO* (FIG. 48). Therefore, the electrocyclization was photochemically allowed.

Figure 49:
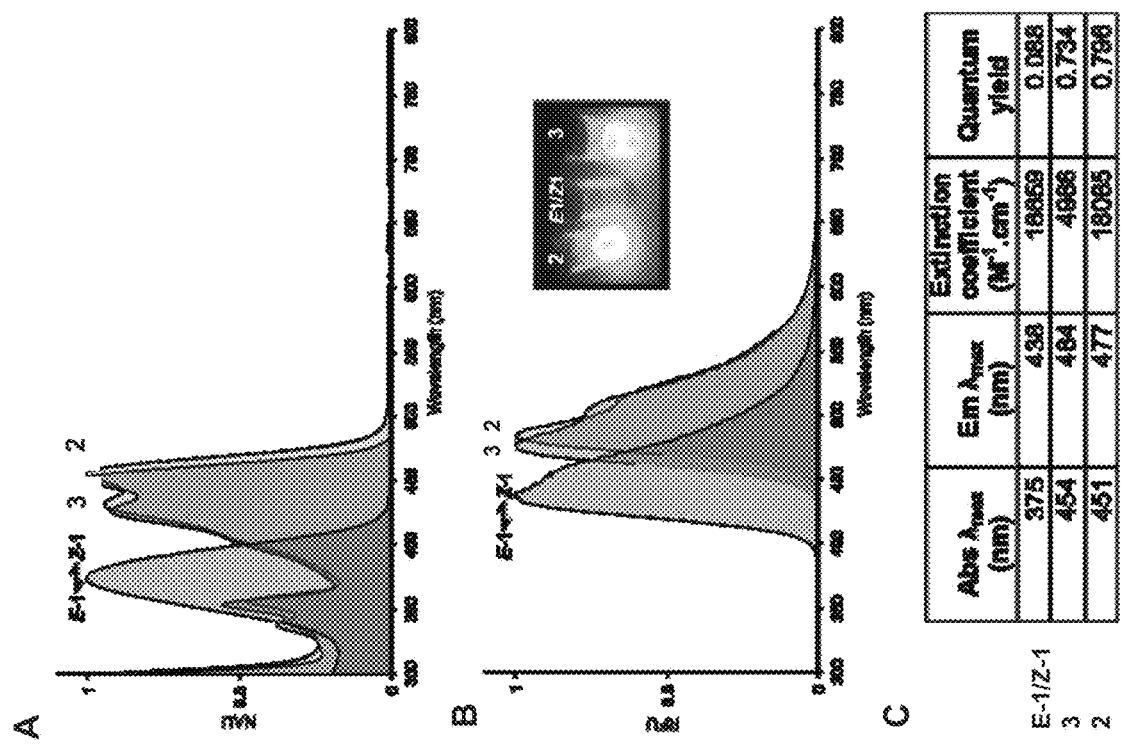
FIG. 49, comprised of FIGS. 49A-49C, depicts experimental data of absorbption and phytophysical properties of compounds E-1/Z-1, 2, and 3.

X-ray crystallography was used to confirm the structure of 2 (FIG. 47). Comparing the crystal structures of 1 and 2, it is clear that the red shifted emission of 2 is the result of increased planarity within the scaffold, allowing for greater electron delocalization through the extended π-system. The higher rigidity also reduces nonradiative bond rotation and remarkably improve quantum yield (FIG. 49). Both photoproducts have higher quantum yield than most of the well-known fluorophores such as quinine, DAPI, Hoechst, Cy3, and Cy5.

Figure 50:
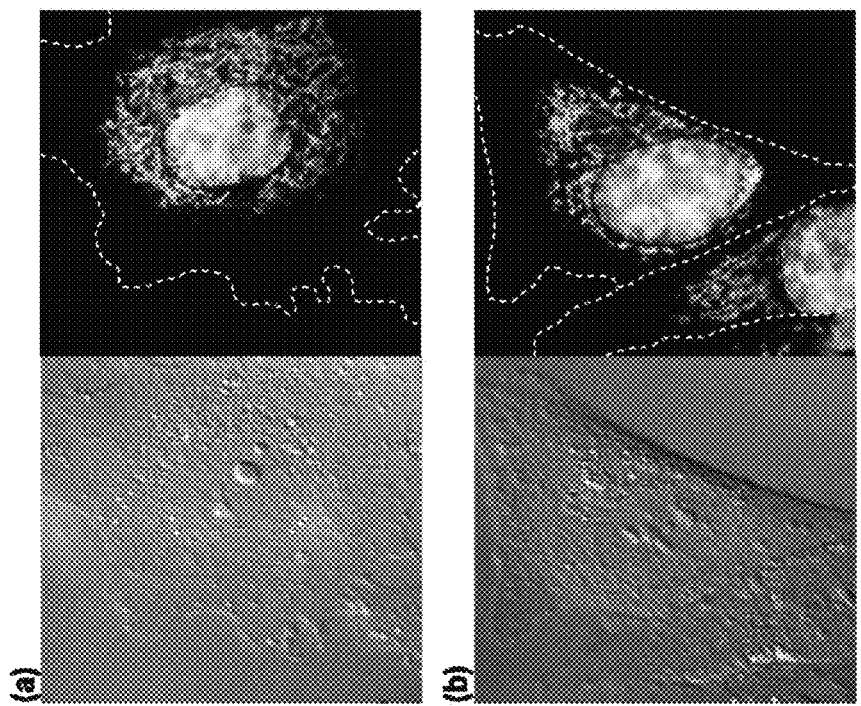
FIG. 50, comprised of FIGS. 50A-50B, depicts a series of confocal microscopy images of compounds 2 and 3.

Using confocal microscopy, both 2 and 3 were shown to be cell-permeable and localize primarily in the mitochondria of HeLa cells (FIG. 50), which was further confirmed by co-staining experiments with Mitotracker Red FM, a well-known commercial mitochondria stain, Compound 3 exhibited a Pearson colocalization correlation of 0.75, indicating significant colocalization.

Figure 51:
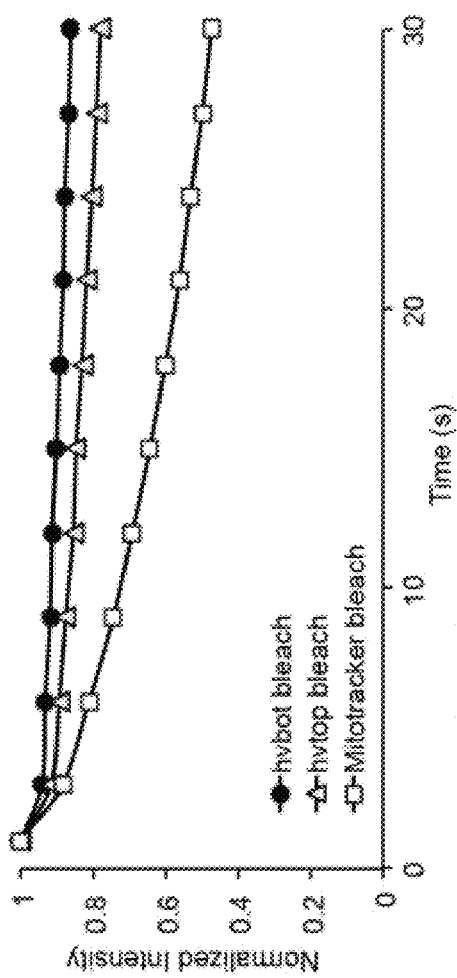
FIG. 51 is a normalized plot of the average intensity of sequential images monitored over 100 laser pulses of 300 ms. HELA cells were treated with 2, 3, and Mitotracker Red FM.

To investigate photostability of 2 and 3, timelapse microscopy experiments were carried out. After 100 scans (300 ms/scan), only a slight decrease in intensity was detected with both 2 and 3, indicating high resistance to photobleaching (FIG. 51).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising at least one compound of formula (I):

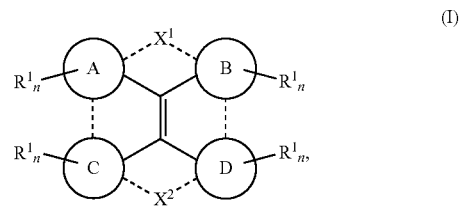

wherein in formula (I):
rings A, B, and C are each independently a monocyclic or bicyclic aryl or a monocyclic or bicyclic heteroaryl ring, ring D is a monocyclic or bicyclic heteroaryl ring, and wherein the aryl or heteroaryl rings are each independently optionally substituted with 0-5 $R^1$ groups;
the bond between rings A and C and between rings B and D is each independently optional;
each occurrence of $R^1$ is independently selected from the group consisting of H, $-C_1-C_{20}$ alkyl, $-C_1-C_6$ fluoroalkyl, $-C_1-C_6$ heteroalkyl, F, $C_1$, Br, I, $-CN$, $-NO_2$, $-OR^2$, $-SR^2$, $-S(=O)R^2$, $-S(=O)_2R^2$, $-NHS(=O)_2R^2$, $-C(=O)R^2$, $-OC(=O)R^2$, $-CO_2R^2$, $-OCO_2R^2$, $-CH(R^2)_2$, $-N(R^2)_2$, $-C(=O)N(R^2)_2$, $-OC(=O)N(R^2)_2$, $-NHC(=O)NH(R^2)$, $-NHC(=O)R^2$, $-NHC(=O)OR^2$, $-C(OH)(R^2)_2$, and $-C(NH_2)(R^2)_2$, wherein the alkyl group is optionally substituted;
each occurrence of $R^2$ is independently selected from the group consisting of H, $C_1-C_6$ alkyl, aryl, $C_1-C_6$ heteroalkyl, and $-C_1-C_3$ alkyl-$(C_3-C_6$ cycloalkyl), wherein the alkyl, heteroalkyl or cycloalkyl group is optionally substituted;
$X^1$ and $X^2$ are each optional and each independently selected from the group consisting of O and S; and
each occurrence of n is independently an integer from 0 to 4; and
a salt, solvate, or N-oxide thereof, and any combinations thereof.

2. The composition of claim 1, wherein the compound of formula (I) is at least one compound of formula (II):

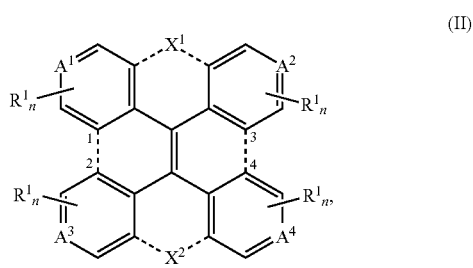

wherein in formula (II):
the bond between carbons 1 and 2 and between carbons 3 and 4 is each independently optional;

each occurrence of $R^1$ is independently selected from the group consisting of H, —$C_1$-$C_6$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$;

each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$A^1$, $A^2$, $A^3$, and $A^4$ are each independently selected from the group consisting of $CR^2$, N, and $\overset{\oplus}{N}R^2$;

$X^1$ and $X^2$ are each optional and each independently selected from the group consisting of O and S;
with the proviso that at least one of $X^1$ and $X^2$ is present; and
each occurrence of n is independently an integer from 0 to 4; and
a salt, solvate, or N-oxide thereof, and any combinations thereof.

3. The composition of claim 1, wherein the compound of formula (I) is at least one compound of formula (III):

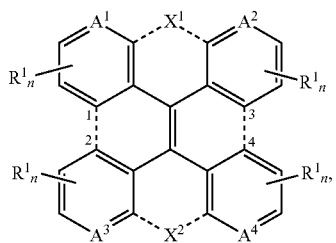

(III)

wherein in formula (III):
the bond between carbons 1 and 2 and between carbons 3 and 4 is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$;

each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$A^1$, $A^2$, $A^3$, and $A^4$ are each independently selected from the group consisting of $CR^2$, N, and $\overset{\oplus}{N}R^2$;

$X^1$ and $X^2$ are each optional and each independently selected from the group consisting of O and S;
with the proviso that at least one of $X^1$ and $X^2$ is present; and
each occurrence of n is independently an integer from 0 to 4; and
a salt, solvate, or N-oxide thereof, and any combinations thereof.

4. The composition of claim 1, wherein the compound of formula (I) is at least one compound of formula (IV):

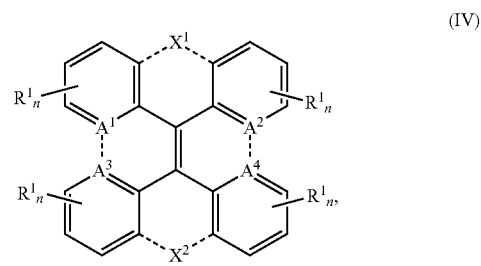

(IV)

wherein in formula (IV):
the bond between $A^1$ and $A^3$ and between $A^2$ and $A^4$ is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)O$R^2$, —C(OH)($R^2$)$_2$, and —C($NH_2$)($R^2$)$_2$;

each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;

$A^1$, $A^2$, and $A^3$ are each independently selected from the group consisting of $CR^2$, N, and $\overset{\oplus}{N}R^2$;

$A^4$ is selected from the group consisting of N and $\overset{\oplus}{N}R^2$;

$X^1$ and $X^2$ are each optional and each independently selected from the group consisting of O and S;
with the proviso that at least one of $X^1$ and $X^2$ is present; and
each occurrence of n is independently an integer from 0 to 4; and
a salt, solvate, or N-oxide thereof, and any combinations thereof.

5. The composition of claim 2, wherein the compound of formula (II) is selected from the group consisting of:

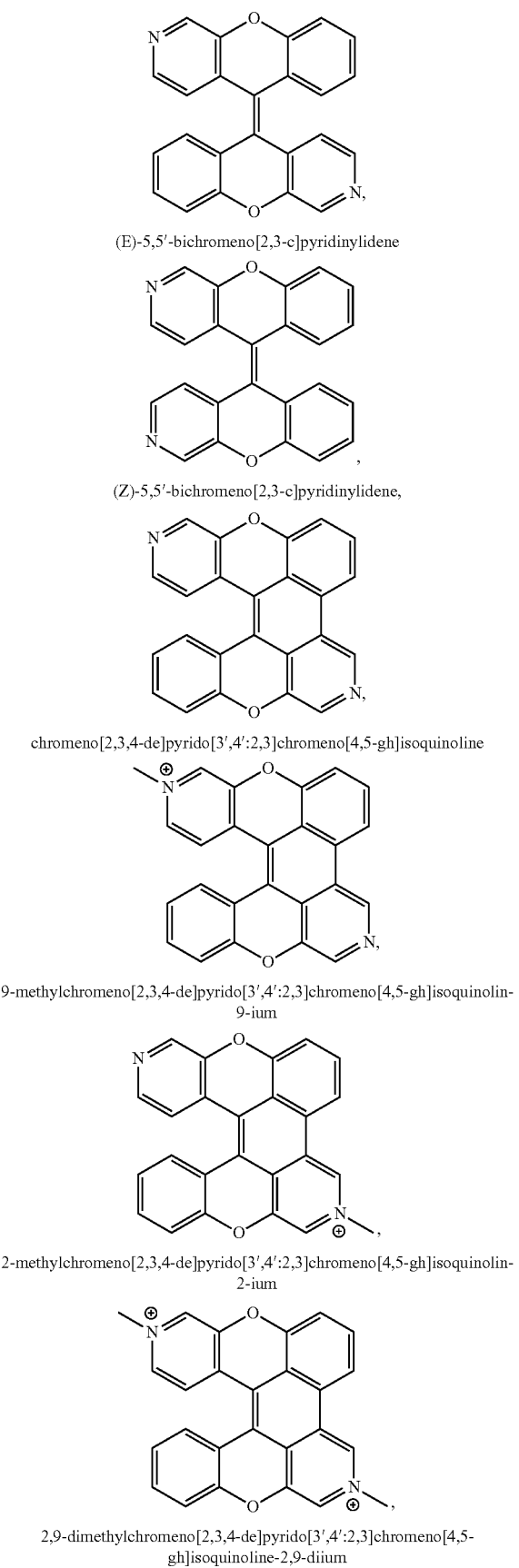
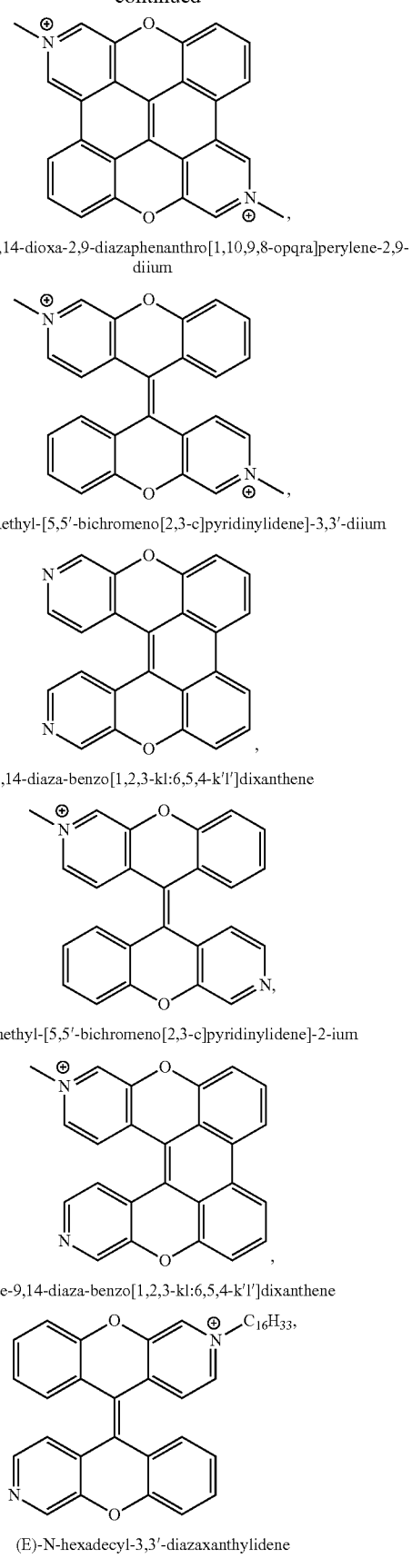

-continued

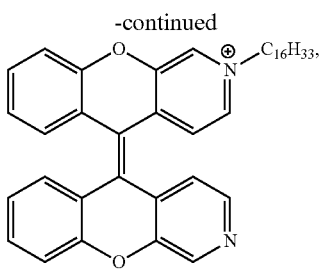
(Z)-N-hexadecyl-3,3'-diazaxanthylidene

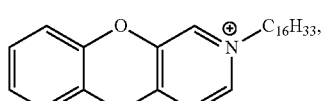
(E)-N,N'-dihexadecyl-3,3'-diazaxanthylidene

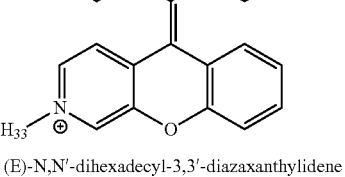
(Z)-N,N'-dihexadecyl-3,3'-diazaxanthylidene

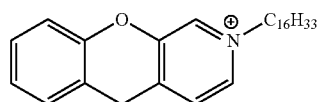
(E)-N-sulfopropyl-N'-hexadecyl-3,3'-diazaxanthylidene

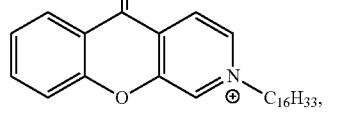
(Z)-N-sulfopropyl-N'-hexadecyl-3,3'-diazaxanthylidene

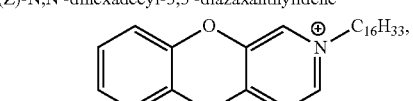, and

-continued

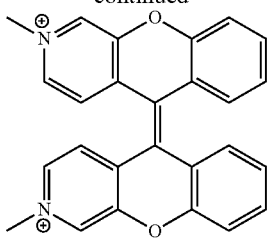

mixtures thereof and salts thereof.

6. The composition of claim 3, wherein the compound of formula (III) is selected from the group consisting of:

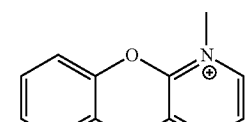, (E)-N'-methyl-4,4'-diazaxanthylidene

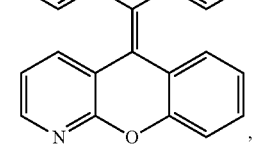, (Z)-N'-methyl-4,4'-diazaxanthylidene

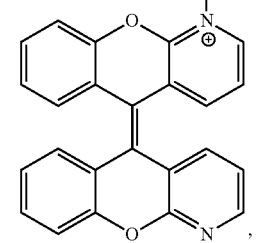, (E)-N,N'-dimethyl-4,4'-diazaxanthylidene

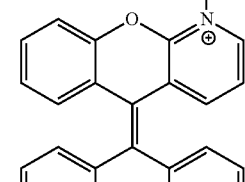, (Z)-N,N'-dimethyl-4,4'-diazaxanthylidene

-continued

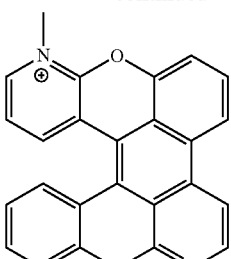

8-methyl-2-aza-7,16-dioxabenzo[o]pyrido[3,2-a]perylene , and

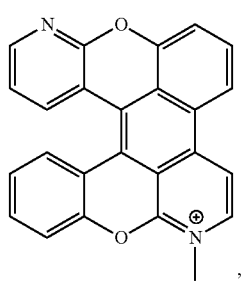

1-methyl-2-aza-7,16-dioxabenzo[o]pyrido[3,2-a]perylene , mixtures thereof and salts thereof.

7. The composition of claim 4, wherein the compound of formula (IV) is selected from the group consisting of:

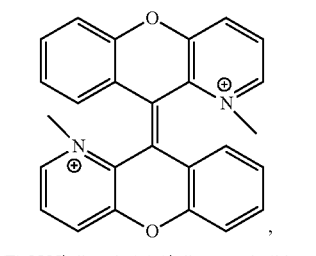

(E)-N,N'-dimethyl-1,1'-diazaxanthylidene ,

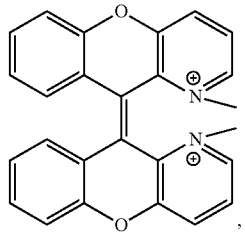

(Z)-N,N'-dimethyl-1,1'-diazaxanthylidene ,

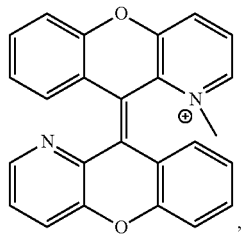

(E)-N-methyl-1,1'-diazaxanthylidene ,

-continued

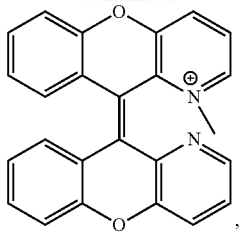

(Z)-N-methyl-1,1'-diazaxanthylidene ,

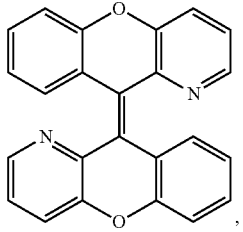

(E)-1,1'-diazaxanthylidene ,

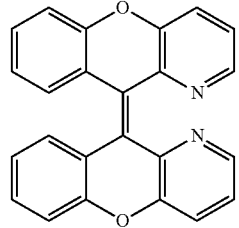

(Z)-1,1'-diazaxanthylidene mixtures thereof and salts thereof.

8. A method for identifying a compound as an imaging agent, comprising the steps of:
providing a DAZAX-based scaffold or derivative thereof;
modifying the scaffold to create a plurality of compounds;
evaluating the plurality of compounds for bioimaging properties; and
identifying a compound selected from the plurality of compounds as an imaging agent.

9. The method of claim 8, further comprising the step of identifying selection criteria.

10. The method of claim 9, further comprising the step of selecting a compound for use as an imaging agent in a bioimaging application based on the evaluation of the compound according to the selection criteria.

11. The method of claim 8, wherein the step of modifying the scaffold comprises at least one modification selected from the group consisting of E-/Z-interconversion, methylation, photocyclization, electrophillic aromatic substitution, sub sequent crosscoupling, nucleophillic aromatic substitution, and combinations thereof.

12. The method of claim 10, wherein the selection criteria comprises the group consisting of fluorescence, water solubility, cell permeability, non-toxicity, red-shifted excitation and emission maxima, stokes shift, resistance to photobleaching, compatibility with laser lines, brightness, size specific location, and photoswitching.

13. The method of claim 10, wherein the bioimaging application is selected from the group consisting of cell staining, fluorescence imaging, and CT scanning.

14. The method of claim 8, wherein the DAZAX-based scaffold is comprised of at least one compound selected from the group consisting of:

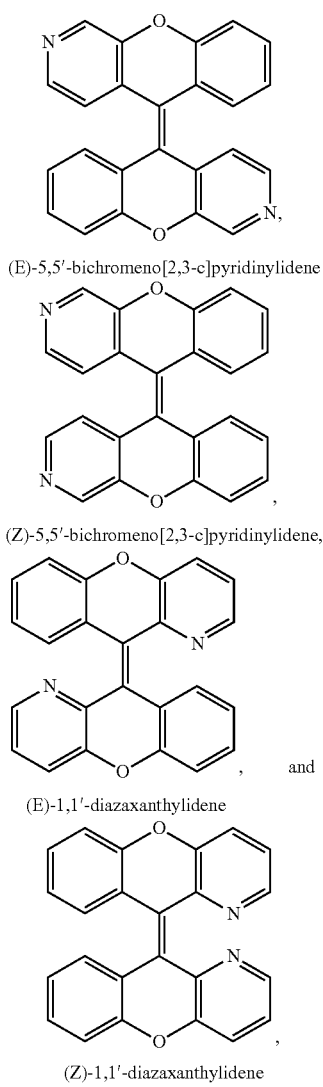

(E)-5,5'-bichromeno[2,3-c]pyridinylidene (Z)-5,5'-bichromeno[2,3-c]pyridinylidene, and (E)-1,1'-diazaxanthylidene (Z)-1,1'-diazaxanthylidene salts thereof, and mixtures thereof.

15. The method of claim 8, wherein the compound is at least one compound of formula (I):

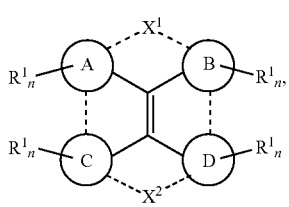

(I)

wherein in formula (I):
rings A, B, C, and D are each independently a monocyclic or bicyclic aryl or a monocyclic or bicyclic heteroaryl ring, and wherein the aryl or heteroaryl rings are each independently optionally substituted with 0-5 $R^1$ groups;
the bond between rings A and C and between rings B and D is each independently optional;
each occurrence of $R^1$ is independently selected from the group consisting of H, —$C_1$-$C_{20}$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —$S(=O)R^2$, —$S(=O)_2R^2$, —$NHS(=O)_2R^2$, —$C(=O)R^2$, —$OC(=O)R^2$, —$CO_2R^2$, —$OCO_2R^2$, —$CH(R^2)_2$, —$N(R^2)_2$, —$C(=O)N(R^2)_2$, —$OC(=O)N(R^2)_2$, —$NHC(=O)NH(R^2)$, —$NHC(=O)R^2$, —$NHC(=O)OR^2$, —$C(OH)(R^2)_2$, and —$C(NH_2)(R^2)_2$, wherein the alkyl group is optionally substituted;
each occurrence of $R^2$ is independently selected from the group consisting of H, $C_1$-$C_6$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;
$X^1$ and $X^2$ are each optional and each independently selected from the group consisting of O and S; and
each occurrence of n is independently an integer from 0 to 4; and
a salt, solvate, or N-oxide thereof, and any combinations thereof.

16. The method of claim 15, wherein the compound of formula (I) is at least one compound of formula (II):

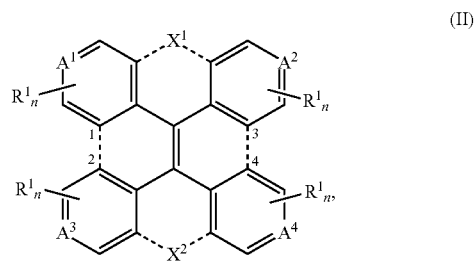

(II)

wherein in formula (II):
the bond between carbons 1 and 2 and between carbons 3 and 4 is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —$S(=O)R^2$, —$S(=O)_2R^2$, —$NHS(=O)_2R^2$, —$C(=O)R^2$, —$OC(=O)R^2$, —$CO_2R^2$, —$OCO_2R^2$, —$CH(R^2)_2$, —$N(R^2)_2$, —$C(=O)N(R^2)_2$, —$OC(=O)N(R^2)_2$, —$NHC(=O)NH(R^2)$, —$NHC(=O)R^2$, —$NHC(=O)OR^2$, —$C(OH)(R^2)_2$, and —$C(NH_2)(R^2)_2$;
each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;
$A^1$, $A^2$, $A^3$, and $A^4$ are each independently selected from the group consisting of $CR^2$, N, and $\overset{\oplus}{N}R^2$;

$X^1$ and $X^2$ are each optional and each independently selected from the group consisting of O and S;
with the proviso that at least one of $X^1$ and $X^2$ is present; and
each occurrence of n is independently an integer from 0 to 4; and
a salt, solvate, or N-oxide thereof, and any combinations thereof.

17. The method of claim 15, wherein the compound of formula (I) is at least one compound of formula (III):

(III)

wherein in formula (III):
the bond between carbons 1 and 2 and between carbons 3 and 4 is each independently optional;
each occurrence of $R^1$ is independently selected from the group consisting of H, —$C_1$-$C_6$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)$OR^2$, —C(OH)($R^2$)$_2$, and —C($NH_2$)($R^2$)$_2$;
each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;
$A^1$, $A^2$, $A^3$, and $A^4$ are each independently selected from the group consisting of $CR^2$, N, and $$\overset{\oplus}{N}R^2;$$

$X^1$ and $X^2$ are each optional and each independently selected from the group consisting of O and S;
with the proviso that at least one of $X^1$ and $X^2$ is present; and
each occurrence of n is independently an integer from 0 to 4; and
a salt, solvate, or N-oxide thereof, and any combinations thereof.

18. The method of claim 15, wherein the compound of formula (I) is at least one compound of formula (IV):
wherein in formula (IV):

(IV)

the bond between $A^1$ and $A^3$ and between $A^2$ and $A^4$ is each independently optional;

each occurrence of $R^1$ is independently selected from the group consisting of H, —$C_1$-$C_6$ alkyl, —$C_1$-$C_6$ fluoroalkyl, —$C_1$-$C_6$ heteroalkyl, F, $C_1$, Br, I, —CN, —$NO_2$, —$OR^2$, —$SR^2$, —S(=O)$R^2$, —S(=O)$_2R^2$, —NHS(=O)$_2R^2$, —C(=O)$R^2$, —OC(=O)$R^2$, —$CO_2R^2$, —$OCO_2R^2$, —CH($R^2$)$_2$, —N($R^2$)$_2$, —C(=O)N($R^2$)$_2$, —OC(=O)N($R^2$)$_2$, —NHC(=O)NH($R^2$), —NHC(=O)$R^2$, —NHC(=O)$OR^2$, —C(OH)($R^2$)$_2$, and —C($NH_2$)($R^2$)$_2$;
each occurrence of $R^2$ is independently selected from the group consisting of H, $C_1$-$C_{20}$ alkyl, aryl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted;
$A^1$, $A^2$, $A^3$, and $A^4$ are each independently selected from the group consisting of $CR^2$, N, and $$\overset{\oplus}{N}R^2;$$

$X^1$ and $X^2$ are each optional and each independently selected from the group consisting of O and S;
with the proviso that at least one of $X^1$ and $X^2$ is present; and
each occurrence of n is independently an integer from 0 to 4; and
a salt, solvate, or N-oxide thereof, and any combinations thereof.

19. The method of claim 16, wherein the compound of formula (II) is selected from the group consisting of:

(E)-5,5'-bichromeno[2,3-c]pyridinylidene (Z)-5,5'-bichromeno[2,3-c]pyridinylidene, chromeno[2,3,4-de]pyrido[3',4':2,3]chromeno[4,5-gh]isoquinoline

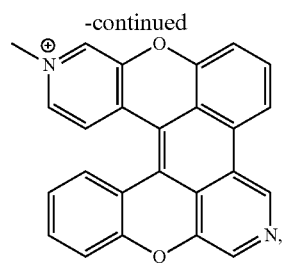

9-methylchromeno[2,3,4-de]pyrido[3',4':2,3]chromeno[4,5-gh]isoquinoline-9-ium

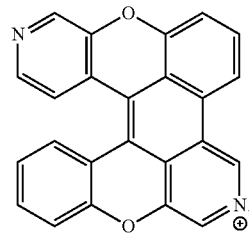

2-methylchromeno[2,3,4-de]pyrido[3',4':2,3]chromeno[4,5-gh]isoquinoline-2-ium

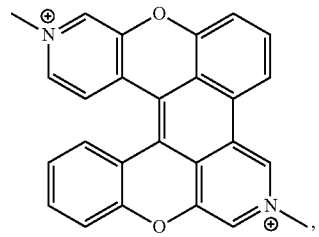

2,9-dimethylchromeno[2,3,4-de]pyrido[3',4':2,3]chromeno[4,5-gh]isoquinoline-2,9-diium

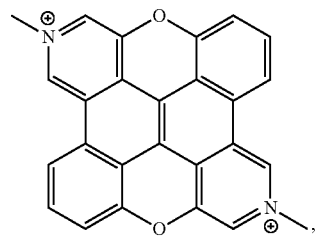

2,9-dimethyl-7,14-dioxa-2,9-diazaphenanthro[1,10,9,8-opqra]perylene-2,9-diium

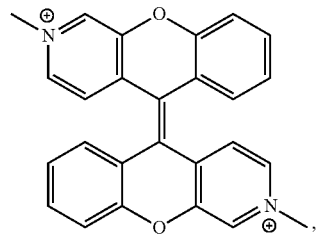

(E)-3,3'-dimethyl-[5,5'-bichromeno[2,3-c]pyridinylidene]-3,3'-diium

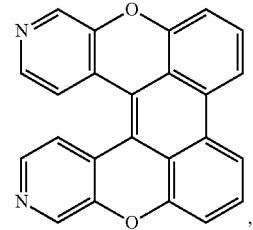

9,14-diaza-benzo[1,2,3-kl:6,5,4-k'l']dixanthene

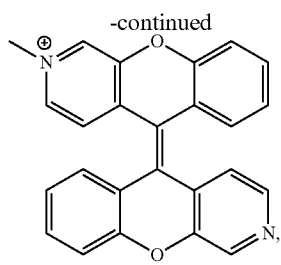

(E)-2-methyl-[5,5'-bichromeno[2,3-c]pyridinylidene]-2-ium

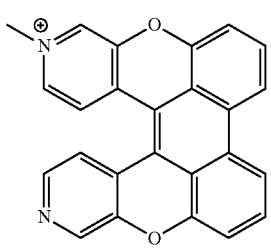

9-Me-9,14-diaza-benzo[1,2,3-kl:6,5,4-k'l']dixanthene

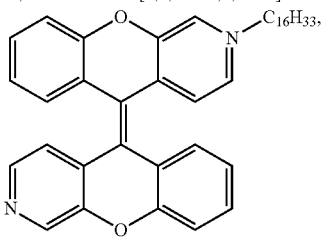

(E)-N-hexadecyl-3,3'-diazaxanthylidene

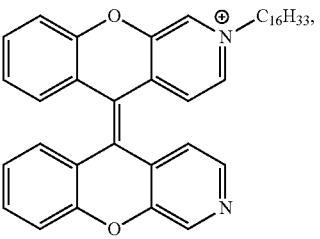

(Z)-N-hexadecyl-3,3'-diazaxanthylidene

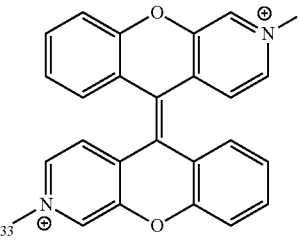

(E)-N,N'-dihexadecyl-3,3'-diazaxanthylidene

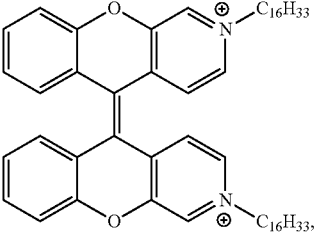

(Z)-N,N'-dihexadecyl-3,3'-diazaxanthylidene

-continued

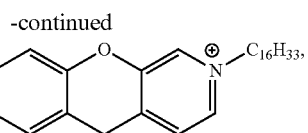

(E)-N-sulfopropyl-N'-hexadecyl-3,3'-diazaxanthylidene

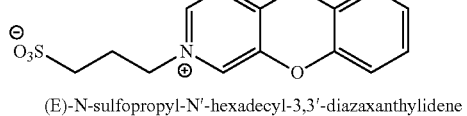

(Z)-N-sulfopropyl-N'-hexadecyl-3,3'-diazaxanthylidene

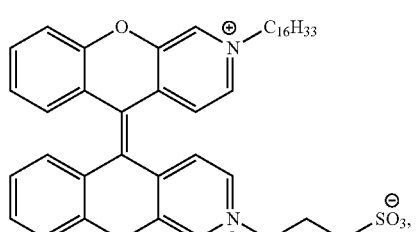, and

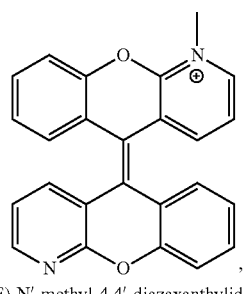

mixtures thereof and salts thereof.

20. The method of claim 17, wherein the compound of formula (III) is selected from the group consisting of:

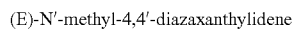

(E)-N'-methyl-4,4'-diazaxanthylidene

-continued

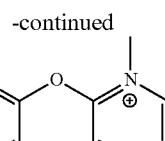

(Z)-N'-methyl-4,4'-diazaxanthylidene

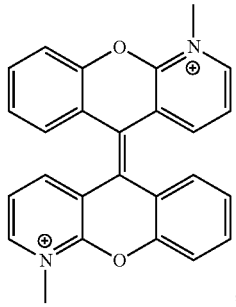

(E)-N,N'-dimethyl-4,4'-diazaxanthylidene

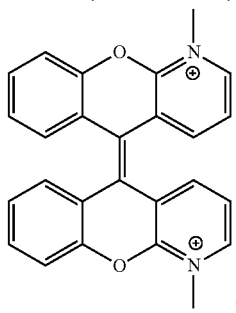

(Z)-N,N'-dimethyl-4,4'-diazaxanthylidene

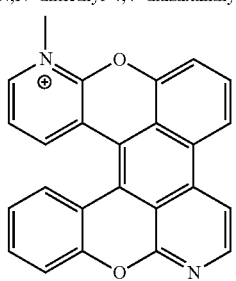

8-methyl-2-aza-7,16-dioxabenzo[o]pyrido[3,2-a]perylene

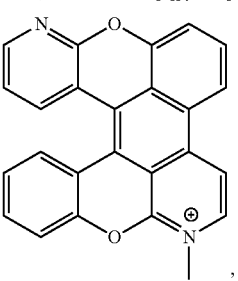

1-methyl-2-aza-7,16-dioxabenzo[o]pyrido[3,2-a]perylene mixtures thereof and salts thereof.

21. The method of claim 18, wherein the compound of formula (IV) is selected from the group consisting of:

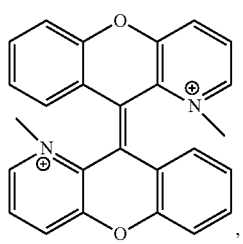

(E)-N,N'-dimethyl-1,1'-diazaxanthylidene

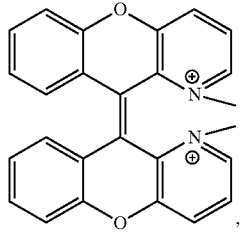

(Z)-N,N'-dimethyl-1,1'-diazaxanthylidene

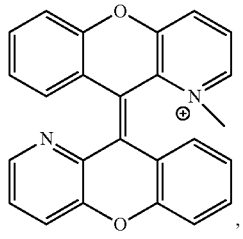

(E)-N-methyl-1,1'-diazaxanthylidene

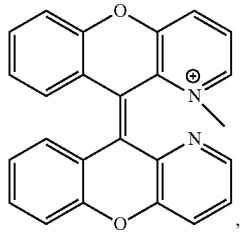

(Z)-N-methyl-1,1'-diazaxanthylidene

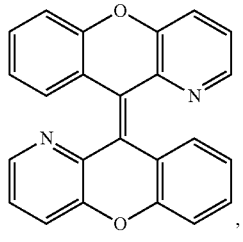

(E)-1,1'-diazaxanthylidene

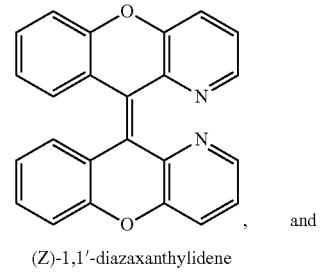, and (Z)-1,1'-diazaxanthylidene

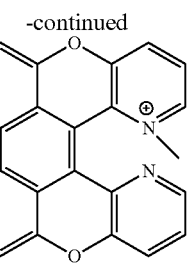

mixtures thereof and salts thereof.

22. A method for imaging a sample, the method comprising:
- providing a sample;
- contacting the sample with an imaging agent;
- irradiating the sample with an excitation wavelength range; and
- detecting fluorescence of the sample, thereby imaging the sample.

23. The method of claim 22, wherein at least a portion of the sample exhibits increased fluorescence after the contacting step compared to before the contacting step.

24. The method of claim 22, wherein the irradiation has an excitation wavelength range of about 375 nm to about 450 nm.

25. The method of claim 22, wherein only a portion of the sample is irradiated.

26. The method of claim 22, wherein the imaging agent is selected from the group consisting of

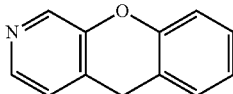 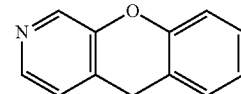

(E)-5,5'-bichromeno[2,3-c]pyridinylidene  (Z)-5,5'-bichromeno[2,3-c]pyridinylidene

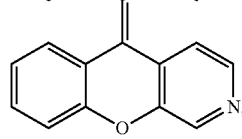 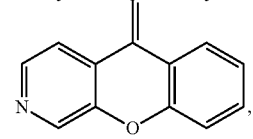

, and (E)-1,1'-diazaxanthylidene  (Z)-1,1'-diazaxanthylidene salts thereof, and mixtures thereof.

27. The method of claim 22, wherein the sample is a cell.

28. The method of claim 27, wherein the cell is a live cell.

* * * * *